US008492358B2

(12) United States Patent
Kandimalla et al.

(10) Patent No.: US 8,492,358 B2
(45) Date of Patent: Jul. 23, 2013

(54) AGONISTS OF TOLL-LIKE RECEPTOR 3 AND METHODS OF THEIR USE

(75) Inventors: Ekambar Kandimalla, Southborough, MA (US); Tao Lan, Winchester, MA (US); Victoria Jane Philbin, Boston, MA (US); Sudhir Agrawal, Shrewsbury, MA (US)

(73) Assignee: Idera Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 13/168,494

(22) Filed: Jun. 24, 2011

(65) Prior Publication Data
US 2012/0034248 A1 Feb. 9, 2012

Related U.S. Application Data

(60) Provisional application No. 61/435,434, filed on Jan. 24, 2011, provisional application No. 61/419,488, filed on Dec. 3, 2010, provisional application No. 61/358,543, filed on Jun. 25, 2010.

(51) Int. Cl.
*C12N 15/11* (2006.01)
*A61K 49/00* (2006.01)

(52) U.S. Cl.
USPC .......................................... 514/44 A; 424/9.1

(58) Field of Classification Search
None
See application file for complete search history.

(56) References Cited

U.S. PATENT DOCUMENTS

| | | | |
|---|---|---|---|
| 2008/0171712 A1* | 7/2008 | Kandimalla et al. ............ | 514/44 |
| 2010/0215642 A1 | 8/2010 | Lan et al. | |

FOREIGN PATENT DOCUMENTS

| | | |
|---|---|---|
| WO | WO2009105260 | 8/2009 |
| WO | WO2008109083 | 12/2009 |

OTHER PUBLICATIONS

Adams et al, The rationale for combined chemo/immunotherapy using a Toll-like receptor 3 (TLR3) agonist and tumour-derived exosomes in advanced ovarian cancer, Mar. 18, 2005, Vaccine, 23:17-18, pp. 2374-2378.*
Gross et al, Investigations of the Metastable Decay of DNA under Ultraviolet Matrix-Assisted Laser Desorption/Ionization Conditions with Post-Source-Decay Analysis and Hydrogen/Deuterium Exchange, 1998, J Am Soc Mass Spectrom, 9: 866-878.*
Matsuda et al, Induction of Interferon and Host Resistance in vivo by Double-Stranded Complexes of Copolyribonucleotide of Inosinic and Guanylic Acids with Polyribocytidylic Acid, Archiv fur die gesamte Virusforschung, 1971, vol. 34, 105-118.*
Hornung et al., "Quantitative Expression of Toll-like Receptor 1-10 mRNA in Cellular Subsets of Human Peripheral Blood Mononuclear . . . " J. Immunol. 168:4531-4537 (2002).

Akira et al., "Toll-like receptors: critical proteins linking innate and acquired immunity" Nature Immunol. 2:675-680 (2001).
Medzhitov, "Toll-like receptors and innate immunity" Nature Rev. Immunol. 1:135-145 (2001).
Diebold et al., "Innate Antiviral Reponses by Means of TLR7-Mediated Recognition of Single-Stranded RNA" Science 303:1529-1531 (2004).
Liew et al., "Negative regulation of toll-like receptor-mediated immune responses" Nature 5:446-458 (2005).
Hemmi et al., "Small anti-viral compounds activate immunne cells via the TLR7 myD88-dependent signaling pathway" Nat. Immunol 3:196-200 (2002).
Jurk et al., "Human TLR7 or TLR8 independently confer responsiveness to the antiviral compound R0848" Nat. Immunol 3:499 (2002).
Lee et al., "Molecular basis for the immunostim. activity of guanine nucleoside analogs: Activation of Toll-like receptor 7" Proc. Natl. Acad. Sci. USA 100:6646-6651 (2003).
Alexopoulou, "Recognition of double-stranded RNA and activation of NF-KB by Toll-like receptor 3" Nature 413:732-738 (2001).
Akira, "Toll-like receptor signaling" J. Biol. Chem. 278:38105 (2003).
Hong-Geller et al., "Targeting Toll-Like Receptor Signaling Pathways for Design of Novel Immune Therapeutics" Curr. Drug Disc. Tech, 5:29-38 (2008).
Miggin et al., "New Insights into the Regulation of TLR Signaling" J. Leukoc. Biol. 80:220-226 (2006).
Papadimitraki et al., "Toll like receptors and autoimmunity: A critical appraisal" J. Autoimmun. 29:310-318 (2007).
Sun et al., TLR7/9 "Antagonists as Therapeutics for Immune-Mediated Inflammatory Disorders" Inflam. Allergy Drug Targets 6:223-235 (2007).
Diebold, "Recognition of viral single-stranded RNA by Toll-like receptors" Adv. Drug Delivery Rev. 60:813-823 (2008).
Cook et al., "Toll-like receptors in the pathogenesis of human disease" Nature Immunol. 5:975-979 (2004).
Tse et al., "Defining a role for ambient TLR ligand exposures in the genesis and prevention of allergic disease" Semin. Immunopathol. 30:53-62 (2008).
Tobias et al., "TLR2 in murine atherosclerosis" Semin. Immunopathol. 30:23-27 (2008).
Ropert et al., "Role of TLRs/MyD88 in host resistance and pathogenesis during protozoan infection: lessons from malaria" Semin. Immunopathol. 30:41-51 (2008).
Lee et al., "The 'polarizing-tolerizing' mechanism of intestinal epithelium: its relevance to colonic hemeostasis" Semin. Immunopathol. 30:3-9 (2008).
Gao et al., "Severe sepsis and toll-like receptors" Semin. Immunopathol. 30:29-40 (2008).
Vijay-Kumar et al., "Toll like receptor-5: protecting the gut from enteric microbes" Semin. Immunopathol. 30:11-21 (2008).
Dekker et al., "Joining of long double-stranded RNA molecules through controlled overhangs" Nucleic Acid Res. 32(18) e140 (2004).

(Continued)

*Primary Examiner* — Tracy Vivlemore
*Assistant Examiner* — Kate Poliakova
(74) *Attorney, Agent, or Firm* — Wood, Phillips, Katz, Clark & Mortimer

(57) ABSTRACT

TLR3 agonist compounds, compositions and methods are provided for stimulating the activity of TLR3. The compositions comprise oligonucleotide-based compounds that bind to and activate TLR3. The compositions may also comprise oligonucleotide-based compounds that bind to and activate TLR3 in combination with other therapeutic and/or prophylactic compounds and/or compositions. Methods of using these compounds and compositions for stimulation of TLR3 activity and for prevention or treatment of diseases wherein modulation of TLR3 activity would be beneficial are provided.

14 Claims, 15 Drawing Sheets

OTHER PUBLICATIONS

Field et al., "Inducers of interferon and Host Resistence, v. In vitro studies" Proc. Natl. Acad. Sci. USA 61:340 (1968).

Okahira et al., "Interferon-β induction through Toll-like receptor 3 depends on double-stranded RNA structure" DNA Cell Biol. 24:614-623 (2005).

Iyer et al., "A novel nucleoside phosphoramidite synthon derived from 1R, 2S-ephedrine" Tetrahedron: Asymmetry 6:1051-1054 (1995).

Absher et al., "Toxic Properties of a Synthetic Double-Stranded RNA: Endotoxin-like properties of Poly I.Poly C, an Interferon Stimulator" Nature 223:715-717 (1969).

Lindsay et al., "Toxic Properties of a Synthetic Double-stranded RNA: Progenicity of PolyI.Poly C in Rabbits" Nature 223:717 (1969).

Adamson et al., "Toxic Properties of a Synthetic Double-stranded RNA: Embryotoxic Effect of Poly I.Poly C" Nature 223:718 (1969).

Leonard et al., "Toxicity of Interferon Inducers of the Double Stranded RNA Type" (1969) Nature 224:1023-1024 (1969).

Trinchieri et al., "Cooperation of Toll-like receptor signals in innate immune defence" Nat. Rev. Immunol. 7:179-190 (2007).

Kleinman et al., "Sequence- and target-independent angiogenesis suppression by siRNA via TLR3" Nature 452:591-597 (2008).

Tadayoshi et al., "Helix-with-Loops Structure of Polynucleotide. I. Poly(C + IC) and Poly(C + GU)" Bulletin of the Chemical Society of Japan, 40:2272-2277 (1967).

Matsumoto et al., "TL3R: Interferon induction by double-stranded RNA including poly(I:C)" Adv. Drug Deliv. Rev. (2008).

Miller et al., "Roll of toll-like receptors in activation of porcine alveolar macrophages by porcine reproductive and respiratory syndrome virus", Clin Vaccine Immunol., 2009, 16(3), p. 360.

Yarilina et al., "Suppression of the effector phase of inflammatory arthritis by double-stranded RNA is mediated by type I IFNs", J. Immunol., 2007, 178(4), pp. 2204-2211.

* cited by examiner

```
                        SEQUENCE LISTING

<160> NUMBER OF SEQ ID NOS: 248

<210> SEQ ID NO 1
<211> LENGTH: 40
<212> TYPE: RNA
<213> ORGANISM: Artificial Sequence
<220> FEATURE:
<223> OTHER INFORMATION: Synthetic oligonucleotide

<400> SEQUENCE: 1
gcaguugaca cccccccccc cccccccccc cccccccccc                          40

<210> SEQ ID NO 2
<211> LENGTH: 40
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (11)..(40)
<223> OTHER INFORMATION: n represents inosine

<400> SEQUENCE: 2
ugucaacugc nnnnnnnnnn nnnnnnnnnn nnnnnnnnnn                          40

<210> SEQ ID NO 3
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 3
cacuggcagu ugacacccccc cccccccccc cccccccccc cccccccccc              50

<210> SEQ ID NO 4
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 4
ugucaacugc cagugnnnnn nnnnnnnnnn nnnnnnnnnn nnnnnnnnnn                50

<210> SEQ ID NO 5
<211> LENGTH: 50
<212> TYPE: RNA
<213> ORGANISM: Artificial Sequence
<220> FEATURE:
<223> OTHER INFORMATION: Synthetic oligonucleotide
```

```
-continued

<400> SEQUENCE: 5
cacuggcagu ugacacaggu cccccccccc cccccccccc cccccccccc            50

<210> SEQ ID NO 6
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (21)..(50)
<223> OTHER INFORMATION: n represents inosine

<400> SEQUENCE: 6
accuguguca acugccagug nnnnnnnnnn nnnnnnnnnn nnnnnnnnnn            50

<210> SEQ ID NO 7
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 7
cacuggcagu ugacacccccc cccccccccc cccccccccc cccccccccc           50

<210> SEQ ID NO 8
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(25)
<223> OTHER INFORMATION: n represents inosine
<220> FEATURE:
<221> NAME/KEY: misc_feature
<222> LOCATION: (27)..(35)
<223> OTHER INFORMATION: n represents inosine
<220> FEATURE:
<221> NAME/KEY: misc_feature
<222> LOCATION: (37)..(45)
<223> OTHER INFORMATION: n represents inosine
<220> FEATURE:
<221> NAME/KEY: misc_feature
<222> LOCATION: (47)..(50)
<223> OTHER INFORMATION: n represents inosine

<400> SEQUENCE: 8
ugucaacugc cagugnnnnn nnnnngnnnn nnnnngnnnn nnnnngnnnn            50

<210> SEQ ID NO 9
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 9
cacuggcagu ugacacccccc cccccccccc cccccccccc cccccccccc           50

<210> SEQ ID NO 10
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
```

```
<221> NAME/KEY: misc_feature
<222> LOCATION: (16)..(50)
<223> OTHER INFORMATION: n represents inosine

<400> SEQUENCE: 10
ugucaacugc cagugnnnnn nnnnnnnnnn nnnnnnnnnn nnnnnnnnnn              50

<210> SEQ ID NO 11
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(15)
<223> OTHER INFORMATION: 2'-OMe

<400> SEQUENCE: 11
cacuggcagu ugacaccccc cccccccccc cccccccccc cccccccccc              50

<210> SEQ ID NO 12
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 12
ugucaacugc cagugnnnnn nnnnnnnnnn nnnnnnnnnn nnnnnnnnnn              50

<210> SEQ ID NO 13
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 13
cacuggcagu ugacaccccc cccccccccc cccccccccc cccccccccc              50

<210> SEQ ID NO 14
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 14
ugucaacugc cagugnnnnn nnnnnnnnnn nnnnnnnnnn nnnnnnnnnn              50

<210> SEQ ID NO 15
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 15
cccccccccc cccccccccc cccccccccc cccccacug gcaguugaca              50
```

```
<210> SEQ ID NO 16
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 16
ugucaacugc cagugnnnnn nnnnnnnnnn nnnnnnnnnn nnnnnnnnnn         50

<210> SEQ ID NO 17
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 17
cacuggcagu ugacacccccc cccccccccc cccccccccc cccccccccc         50

<210> SEQ ID NO 18
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(19)
<223> OTHER INFORMATION: n represents inosine
<220> FEATURE:
<221> NAME/KEY: misc_feature
<222> LOCATION: (21)..(25)
<223> OTHER INFORMATION: n represents inosine
<220> FEATURE:
<221> NAME/KEY: misc_feature
<222> LOCATION: (27)..(30)
<223> OTHER INFORMATION: n represents inosine
<220> FEATURE:
<221> NAME/KEY: misc_feature
<222> LOCATION: (32)..(35)
<223> OTHER INFORMATION: n represents inosine
<220> FEATURE:
<221> NAME/KEY: misc_feature
<222> LOCATION: (37)..(40)
<223> OTHER INFORMATION: n represents inosine
<220> FEATURE:
<221> NAME/KEY: misc_feature
<222> LOCATION: (42)..(45)
<223> OTHER INFORMATION: n represents inosine
<220> FEATURE:
<221> NAME/KEY: misc_feature
<222> LOCATION: (47)..(50)
<223> OTHER INFORMATION: n represents inosine

<400> SEQUENCE: 18
ugucaacugc cagugnnnng nnnngnnnnn gnnnngnnnn gnnnngnnnn         50

<210> SEQ ID NO 19
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 19
cacuggcagu ugacacccccc cccccccccc cccccccccc cccccccccc         50
```

```
<210> SEQ ID NO 20
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(17)
<223> OTHER INFORMATION: n represents inosine
<220> FEATURE:
<221> NAME/KEY: misc_feature
<222> LOCATION: (19)..(20)
<223> OTHER INFORMATION: n represents inosine
<220> FEATURE:
<221> NAME/KEY: misc_feature
<222> LOCATION: (22)..(25)
<223> OTHER INFORMATION: n represents inosine
<220> FEATURE:
<221> NAME/KEY: misc_feature
<222> LOCATION: (27)..(28)
<223> OTHER INFORMATION: n represents inosine
<220> FEATURE:
<221> NAME/KEY: misc_feature
<222> LOCATION: (30)..(31)
<223> OTHER INFORMATION: n represents inosine
<220> FEATURE:
<221> NAME/KEY: misc_feature
<222> LOCATION: (33)..(35)
<223> OTHER INFORMATION: n represents inosine
<220> FEATURE:
<221> NAME/KEY: misc_feature
<222> LOCATION: (37)..(38)
<223> OTHER INFORMATION: n represents inosine
<220> FEATURE:
<221> NAME/KEY: misc_feature
<222> LOCATION: (40)..(41)
<223> OTHER INFORMATION: n represents inosine
<220> FEATURE:
<221> NAME/KEY: misc_feature
<222> LOCATION: (43)..(45)
<223> OTHER INFORMATION: n represents inosine
<220> FEATURE:
<221> NAME/KEY: misc_feature
<222> LOCATION: (47)..(50)
<223> OTHER INFORMATION: n represents inosine

<400> SEQUENCE: 20
ugucaacugc cagugnngnn gnnnngnngn ngnnngnngn ngnnngnnnn             50

<210> SEQ ID NO 21
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 21
ccuccagccu uacagccaag uaugagagcu                                   30

<210> SEQ ID NO 22
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 22
agcucucaua cuuggcugua aggcuggagg                                   30

<210> SEQ ID NO 23
<211> LENGTH: 40
<212> TYPE: RNA
```

```
<213> ORGANISM: Artificial Sequence
<220> FEATURE:
<223> OTHER INFORMATION: Synthetic oligonucleotide

<400> SEQUENCE: 23
gggagacagg ccuguuccau ggccaacacg uuugucuccc                              40

<210> SEQ ID NO 24
<211> LENGTH: 40
<212> TYPE: RNA
<213> ORGANISM: Artificial Sequence
<220> FEATURE:
<223> OTHER INFORMATION: Synthetic oligonucleotide

<400> SEQUENCE: 24
gggagacaaa cguguuggcc auggaacagg ccugucuccc                              40

<210> SEQ ID NO 25
<211> LENGTH: 40
<212> TYPE: RNA
<213> ORGANISM: Artificial Sequence
<220> FEATURE:
<223> OTHER INFORMATION: Synthetic oligonucleotide

<400> SEQUENCE: 25
cugaacaucu gcggacggac cuagauacgg aaccuuuguu                              40

<210> SEQ ID NO 26
<211> LENGTH: 40
<212> TYPE: RNA
<213> ORGANISM: Artificial Sequence
<220> FEATURE:
<223> OTHER INFORMATION: Synthetic oligonucleotide

<400> SEQUENCE: 26
aacaaagguu ccguaucuag guccguccgc agauguucag                              40

<210> SEQ ID NO 27
<211> LENGTH: 40
<212> TYPE: RNA
<213> ORGANISM: Artificial Sequence
<220> FEATURE:
<223> OTHER INFORMATION: Synthetic oligonucleotide

<400> SEQUENCE: 27
acaucugcgg acggaccuag auacggaacc uuuguuguug                              40

<210> SEQ ID NO 28
<211> LENGTH: 40
<212> TYPE: RNA
<213> ORGANISM: Artificial Sequence
<220> FEATURE:
<223> OTHER INFORMATION: Synthetic oligonucleotide

<400> SEQUENCE: 28
caacaacaaa gguuccguau cuagguccgu ccgcagaugu                              40

<210> SEQ ID NO 29
<211> LENGTH: 24
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n represents glycerol
<220> FEATURE:
```

```
<221> NAME/KEY: misc_feature
<222> LOCATION: (24)..(24)
<223> OTHER INFORMATION: n represents glycerol

<400> SEQUENCE: 29
nccccccccc cccccccccc cccn                                              24

<210> SEQ ID NO 30
<211> LENGTH: 24
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n represents glycerol
<220> FEATURE:
<221> NAME/KEY: misc_feature
<222> LOCATION: (2)..(23)
<223> OTHER INFORMATION: n represents inosine
<220> FEATURE:
<221> NAME/KEY: misc_feature
<222> LOCATION: (24)..(24)
<223> OTHER INFORMATION: n represents glycerol

<400> SEQUENCE: 30
nnnnnnnnnn nnnnnnnnnn nnnn                                              24

<210> SEQ ID NO 31
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 31
cccccccccc cccccccccc cccccccccc                                        30

<210> SEQ ID NO 32
<211> LENGTH: 30
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(30)
<223> OTHER INFORMATION: n represents inosine

<400> SEQUENCE: 32
nnnnnnnnnn nnnnnnnnnn nnnnnnnnnn                                        30

<210> SEQ ID NO 33
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 33
cccccccccc cccccccccc cccccccccc                                        30

<210> SEQ ID NO 34
<211> LENGTH: 30
<212> TYPE: RNA
<213> ORGANISM: Artificial Sequence
<220> FEATURE:
<223> OTHER INFORMATION: Synthetic oligonucleotide
<220> FEATURE:
```

```
<221> NAME/KEY: misc_feature
<222> LOCATION: (1)..(30)
<223> OTHER INFORMATION: n represents inosine

<400> SEQUENCE: 34
nnnnnnnnnn nnnnnnnnnn nnnnnnnnnn                                    30

<210> SEQ ID NO 35
<211> LENGTH: 45
<212> TYPE: RNA
<213> ORGANISM: Artificial Sequence
<220> FEATURE:
<223> OTHER INFORMATION: Synthetic oligonucleotide

<400> SEQUENCE: 35
cccccccccc cccccccccc cccccccccc cccccccccc ccccc                   45

<210> SEQ ID NO 36
<211> LENGTH: 45
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(45)
<223> OTHER INFORMATION: n represents inosine

<400> SEQUENCE: 36
nnnnnnnnnn nnnnnnnnnn nnnnnnnnnn nnnnnnnnnn nnnnn                   45

<210> SEQ ID NO 37
<211> LENGTH: 55
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (26)..(30)
<223> OTHER INFORMATION: n represents 1,3-propanediol

<400> SEQUENCE: 37
ccuccagccu uacagccaag uaugannnnn ccuccagccu uacagccaag uauga         55

<210> SEQ ID NO 38
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 38
ucauacuugg cuguaaggcu ggagg                                         25

<210> SEQ ID NO 39
<211> LENGTH: 60
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (26)..(35)
<223> OTHER INFORMATION: n represents 1,2-propanediol

<400> SEQUENCE: 39
ccuccagccu uacagccaag uaugannnnn nnnnnccucc agccuuacag ccaaguauga    60
```

```
<210> SEQ ID NO 40
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 40
ucauacuugg cguuaaggcu ggagg                                          25

<210> SEQ ID NO 41
<211> LENGTH: 65
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (26)..(40)
<223> OTHER INFORMATION: n represents 1,3-propanediol

<400> SEQUENCE: 41
ccuccagccu acagccaag uaugannnnn nnnnnnnnnn ccuccagccu uacagccaag     60
uauga                                                                65

<210> SEQ ID NO 42
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 42
ucauacuugg cguuaaggcu ggagg                                          25

<210> SEQ ID NO 43
<211> LENGTH: 40
<212> TYPE: RNA
<213> ORGANISM: Artificial Sequence
<220> FEATURE:
<223> OTHER INFORMATION: Synthetic oligonucleotide

<400> SEQUENCE: 43
gggagacaaa cguguuggcc auggaacagg ccugucuccc                          40

<210> SEQ ID NO 44
<211> LENGTH: 40
<212> TYPE: RNA
<213> ORGANISM: Artificial Sequence
<220> FEATURE:
<223> OTHER INFORMATION: Synthetic oligonucleotide

<400> SEQUENCE: 44
gggagacagg ccuguuccau ggccaacacg uuugucuccc                          40

<210> SEQ ID NO 45
<211> LENGTH: 40
<212> TYPE: RNA
<213> ORGANISM: Artificial Sequence
<220> FEATURE:
<223> OTHER INFORMATION: Synthetic oligonucleotide

<400> SEQUENCE: 45
gggagacaaa cguguuggcc auggaacagg ccugucuccc                          40

<210> SEQ ID NO 46
```

```
<211> LENGTH: 40
<212> TYPE: RNA
<213> ORGANISM: Artificial Sequence
<220> FEATURE:
<223> OTHER INFORMATION: Synthetic oligonucleotide

<400> SEQUENCE: 46
gggagacagg ccuguuccau ggccaacacg uuugucuccc                                40

<210> SEQ ID NO 47
<211> LENGTH: 11
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(6)
<223> OTHER INFORMATION: n represents inosine
<220> FEATURE:
<221> NAME/KEY: misc_feature
<222> LOCATION: (10)..(11)
<223> OTHER INFORMATION: n represents inosine

<400> SEQUENCE: 47
cccnnncccn n                                                              11

<210> SEQ ID NO 48
<211> LENGTH: 11
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(4)
<223> OTHER INFORMATION: n represents inosine
<220> FEATURE:
<221> NAME/KEY: misc_feature
<222> LOCATION: (7)..(8)
<223> OTHER INFORMATION: n represents inosine

<400> SEQUENCE: 48
ccnnccnncc c                                                              11

<210> SEQ ID NO 49
<211> LENGTH: 21
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(4)
<223> OTHER INFORMATION: n represents inosine
<220> FEATURE:
<221> NAME/KEY: misc_feature
<222> LOCATION: (7)..(8)
<223> OTHER INFORMATION: n represents inosine
<220> FEATURE:
<221> NAME/KEY: misc_feature
<222> LOCATION: (11)..(11)
<223> OTHER INFORMATION: n represents 1,3-propandediol
<220> FEATURE:
<221> NAME/KEY: misc_feature
<222> LOCATION: (14)..(15)
<223> OTHER INFORMATION: n represents inosine
<220> FEATURE:
<221> NAME/KEY: misc_feature
<222> LOCATION: (18)..(19)
<223> OTHER INFORMATION: n represents inosine

<400> SEQUENCE: 49
```

```
ccnnccnncc nccnnccnnc c                                           21
```

```
<210> SEQ ID NO 50
<211> LENGTH: 12
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n represents glycerol

<400> SEQUENCE: 50
nccccccccc cc                                                     12
```

```
<210> SEQ ID NO 51
<211> LENGTH: 24
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n represents glycerol
<220> FEATURE:
<221> NAME/KEY: misc_feature
<222> LOCATION: (2)..(23)
<223> OTHER INFORMATION: n represents inosine
<220> FEATURE:
<221> NAME/KEY: misc_feature
<222> LOCATION: (24)..(24)
<223> OTHER INFORMATION: n represents glycerol

<400> SEQUENCE: 51
nnnnnnnnnn nnnnnnnnnn nnnn                                        24
```

```
<210> SEQ ID NO 52
<211> LENGTH: 13
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(13)
<223> OTHER INFORMATION: n represents inosine

<400> SEQUENCE: 52
nnnnnnnnnn nnn                                                    13
```

```
<210> SEQ ID NO 53
<211> LENGTH: 15
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n represents inosine
<220> FEATURE:
<221> NAME/KEY: misc_feature
<222> LOCATION: (3)..(3)
<223> OTHER INFORMATION: n represents inosine
<220> FEATURE:
<221> NAME/KEY: misc_feature
<222> LOCATION: (5)..(5)
<223> OTHER INFORMATION: n represents inosine
<220> FEATURE:
<221> NAME/KEY: misc_feature
<222> LOCATION: (7)..(7)
```

```
<223> OTHER INFORMATION: n represents inosine
<220> FEATURE:
<221> NAME/KEY: misc_feature
<222> LOCATION: (9)..(9)
<223> OTHER INFORMATION: n represents inosine
<220> FEATURE:
<221> NAME/KEY: misc_feature
<222> LOCATION: (11)..(11)
<223> OTHER INFORMATION: n represents inosine
<220> FEATURE:
<221> NAME/KEY: misc_feature
<222> LOCATION: (13)..(13)
<223> OTHER INFORMATION: n represents inosine
<220> FEATURE:
<221> NAME/KEY: misc_feature
<222> LOCATION: (15)..(15)
<223> OTHER INFORMATION: n represents inosine

<400> SEQUENCE: 53
ncncncncnc ncncn                                                      15

<210> SEQ ID NO 54
<211> LENGTH: 9
<212> TYPE: RNA
<213> ORGANISM: Artificial Sequence
<220> FEATURE:
<223> OTHER INFORMATION: Synthetic oligonucleotide

<400> SEQUENCE: 54 cccacaccc                                                              9

<210> SEQ ID NO 55
<211> LENGTH: 9
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(9)
<223> OTHER INFORMATION: n represents inosine

<400> SEQUENCE: 55 ugunnnnnn                                                              9

<210> SEQ ID NO 56
<211> LENGTH: 15
<212> TYPE: RNA
<213> ORGANISM: Artificial Sequence
<220> FEATURE:
<223> OTHER INFORMATION: Synthetic oligonucleotide

<400> SEQUENCE: 56 cccccacac ccccc                                                       15

<210> SEQ ID NO 57
<211> LENGTH: 15
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(15)
<223> OTHER INFORMATION: n represents inosine

<400> SEQUENCE: 57
ugunnnnnnn nnnnn                                                      15

<210> SEQ ID NO 58
```

-continued

```
<211> LENGTH: 20
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(15)
<223> OTHER INFORMATION: n represents inosine
<220> FEATURE:
<221> NAME/KEY: modified_base
<222> LOCATION: (16)..(16)
<223> OTHER INFORMATION: 5-methyl-cytidine

<400> SEQUENCE: 58
nnnnnnnnnn nnnnncgugc                                              20

<210> SEQ ID NO 59
<211> LENGTH: 20
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (17)..(17)
<223> OTHER INFORMATION: 5-methyl-cytidine
<220> FEATURE:
<221> NAME/KEY: modified_base
<222> LOCATION: (19)..(19)
<223> OTHER INFORMATION: 5-methyl-cytidine

<400> SEQUENCE: 59
cccccccccc cccccgcacg                                              20

<210> SEQ ID NO 60
<211> LENGTH: 23
<212> TYPE: RNA
<213> ORGANISM: Artificial Sequence
<220> FEATURE:
<223> OTHER INFORMATION: Synthetic oligonucleotide

<400> SEQUENCE: 60
cccccccccc acacccccccc ccc                                         23

<210> SEQ ID NO 61
<211> LENGTH: 23
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(23)
<223> OTHER INFORMATION: n represents inosine

<400> SEQUENCE: 61
ugunnnnnnn nnnnnnnnnn nnn                                          23

<210> SEQ ID NO 62
<211> LENGTH: 34
<212> TYPE: RNA
<213> ORGANISM: Artificial Sequence
<220> FEATURE:
<223> OTHER INFORMATION: Synthetic oligonucleotide

<400> SEQUENCE: 62 gacaccccccc cccccccccc cccccccccc cccc                             34

<210> SEQ ID NO 63
```

```
<211> LENGTH: 34
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(34)
<223> OTHER INFORMATION: n represents inosine

<400> SEQUENCE: 63 ugucnnnnn nnnnnnnnnn nnnnnnnnnn nnnn                               34

<210> SEQ ID NO 64
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 64
cacuggcagu ugacacaggu uccucacuuc acaaaucguu cccccccccc             50

<210> SEQ ID NO 65
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (41)..(50)
<223> OTHER INFORMATION: n represents inosine

<400> SEQUENCE: 65
aacgauuugu gaagugagga accuguguca acugccagug nnnnnnnnnn             50

<210> SEQ ID NO 66
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 66
cacuggcagu ugacacaggu uccucacuuc acaaaucguu caucgccccc             50

<210> SEQ ID NO 67
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (46)..(50)
<223> OTHER INFORMATION: n represents inosine

<400> SEQUENCE: 67
cgaugaacga uuugugaagu gaggaaccug ugucaacugc cagugnnnnn             50

<210> SEQ ID NO 68
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 68
```

```
cacuggcagu ugacacaggu uccucacuuc cccccccccc cccccccccc         50
```

<210> SEQ ID NO 69
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (31)..(50)
<223> OTHER INFORMATION: n represents inosine

<400> SEQUENCE: 69

```
gaagugagga accuguguca acugccagug nnnnnnnnnn nnnnnnnnnn         50
```

<210> SEQ ID NO 70
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 70

```
cacugcucau ucacacccccc cccccccccc cccccccccc cccccccccc        50
```

<210> SEQ ID NO 71
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 71

```
ugugaaugag cagugnnnnn nnnnnnnnnn nnnnnnnnnn nnnnnnnnnn          50
```

<210> SEQ ID NO 72
<211> LENGTH: 49
<212> TYPE: RNA
<213> ORGANISM: Artificial Sequence
<220> FEATURE:
<223> OTHER INFORMATION: Synthetic oligonucleotide

<400> SEQUENCE: 72

```
gucacaguca aguucccccc cccccccccc cccccccccc ccccccccc          49
```

<210> SEQ ID NO 73
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 73

```
gaacuugacu gugacnnnnn nnnnnnnnnn nnnnnnnnnn nnnnnnnnnn          50
```

<210> SEQ ID NO 74
<211> LENGTH: 49
<212> TYPE: RNA
<213> ORGANISM: Artificial Sequence
<220> FEATURE:

```
<223> OTHER INFORMATION: Synthetic oligonucleotide

<400> SEQUENCE: 74
cgugaacuga cacugccccc cccccccccc cccccccccc ccccccccc                49

<210> SEQ ID NO 75
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 75
cagugucagu ucacgnnnnn nnnnnnnnnn nnnnnnnnnn nnnnnnnnnn                50

<210> SEQ ID NO 76
<211> LENGTH: 60
<212> TYPE: RNA
<213> ORGANISM: Artificial Sequence
<220> FEATURE:
<223> OTHER INFORMATION: Synthetic oligonucleotide

<400> SEQUENCE: 76
cacuggcagu ugacacaggu cccccccccc cccccccccc cccccccccc cccccccccc    60

<210> SEQ ID NO 77
<211> LENGTH: 60
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (21)..(60)
<223> OTHER INFORMATION: n represents inosine

<400> SEQUENCE: 77
accuguguca acugccagug nnnnnnnnnn nnnnnnnnnn nnnnnnnnnn nnnnnnnnnn    60

<210> SEQ ID NO 78
<211> LENGTH: 60
<212> TYPE: RNA
<213> ORGANISM: Artificial Sequence
<220> FEATURE:
<223> OTHER INFORMATION: Synthetic oligonucleotide

<400> SEQUENCE: 78
cacuggcagu ugacaccccc cccccccccc cccccccccc cccccccccc cccccccccc    60

<210> SEQ ID NO 79
<211> LENGTH: 60
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(60)
<223> OTHER INFORMATION: n represents inosine

<400> SEQUENCE: 79
ugucaacugc cagugnnnnn nnnnnnnnnn nnnnnnnnnn nnnnnnnnnn nnnnnnnnnn    60

<210> SEQ ID NO 80
```

```
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 80
cacuggcagu ugacacaccc ccccccccc ccccccccc ccccccccc            50

<210> SEQ ID NO 81
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(20)
<223> OTHER INFORMATION: n represents inosine
<220> FEATURE:
<221> NAME/KEY: misc_feature
<222> LOCATION: (22)..(25)
<223> OTHER INFORMATION: n represents inosine
<220> FEATURE:
<221> NAME/KEY: misc_feature
<222> LOCATION: (27)..(30)
<223> OTHER INFORMATION: n represents inosine
<220> FEATURE:
<221> NAME/KEY: misc_feature
<222> LOCATION: (32)..(35)
<223> OTHER INFORMATION: n represents inosine
<220> FEATURE:
<221> NAME/KEY: misc_feature
<222> LOCATION: (37)..(40)
<223> OTHER INFORMATION: n represents inosine
<220> FEATURE:
<221> NAME/KEY: misc_feature
<222> LOCATION: (42)..(45)
<223> OTHER INFORMATION: n represents inosine
<220> FEATURE:
<221> NAME/KEY: misc_feature
<222> LOCATION: (47)..(50)
<223> OTHER INFORMATION: n represents inosine

<400> SEQUENCE: 81
ugucaacugc cagugnnnnn gnnnngnnnn gnnnngnnnn gnnnngnnnn            50

<210> SEQ ID NO 82
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 82
cacuggcagu ugacacaccc ccccccccc ccccccccc ccccccccc            50

<210> SEQ ID NO 83
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(17)
<223> OTHER INFORMATION: n represents inosine
<220> FEATURE:
<221> NAME/KEY: misc_feature
<222> LOCATION: (19)..(20)
<223> OTHER INFORMATION: n represents inosine
<220> FEATURE:
<221> NAME/KEY: misc_feature
<222> LOCATION: (22)..(23)
```

```
<223> OTHER INFORMATION: n represents inosine
<220> FEATURE:
<221> NAME/KEY: misc_feature
<222> LOCATION: (25)..(26)
<223> OTHER INFORMATION: n represents inosine
<220> FEATURE:
<221> NAME/KEY: misc_feature
<222> LOCATION: (28)..(29)
<223> OTHER INFORMATION: n represents inosine
<220> FEATURE:
<221> NAME/KEY: misc_feature
<222> LOCATION: (31)..(32)
<223> OTHER INFORMATION: n represents inosine
<220> FEATURE:
<221> NAME/KEY: misc_feature
<222> LOCATION: (34)..(35)
<223> OTHER INFORMATION: n represents inosine
<220> FEATURE:
<221> NAME/KEY: misc_feature
<222> LOCATION: (37)..(38)
<223> OTHER INFORMATION: n represents inosine
<220> FEATURE:
<221> NAME/KEY: misc_feature
<222> LOCATION: (40)..(41)
<223> OTHER INFORMATION: n represents inosine
<220> FEATURE:
<221> NAME/KEY: misc_feature
<222> LOCATION: (43)..(44)
<223> OTHER INFORMATION: n represents inosine
<220> FEATURE:
<221> NAME/KEY: misc_feature
<222> LOCATION: (46)..(47)
<223> OTHER INFORMATION: n represents inosine
<220> FEATURE:
<221> NAME/KEY: misc_feature
<222> LOCATION: (49)..(50)
<223> OTHER INFORMATION: n represents inosine

<400> SEQUENCE: 83
ugucaacugc cagugnngnn gnngnngnng nngnngnngn ngnngnngnn        50

<210> SEQ ID NO 84
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 84
cacuggcagu ugacaccccu cccccccccu cccccccccu ccccccccccc       50

<210> SEQ ID NO 85
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(25)
<223> OTHER INFORMATION: n represents inosine
<220> FEATURE:
<221> NAME/KEY: misc_feature
<222> LOCATION: (27)..(35)
<223> OTHER INFORMATION: n represents inosine
<220> FEATURE:
<221> NAME/KEY: misc_feature
<222> LOCATION: (37)..(45)
<223> OTHER INFORMATION: n represents inosine
<220> FEATURE:
<221> NAME/KEY: misc_feature
<222> LOCATION: (47)..(50)
<223> OTHER INFORMATION: n represents inosine

<400> SEQUENCE: 85
```
ugucaacugc cagugnnnnn nnnnnannnn nnnnnannnn nnnnnannnn         50

<210> SEQ ID NO 86
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 86
cacuggcagu ugacaccccc cccccccccc cccccccccc cccccccccc         50

<210> SEQ ID NO 87
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(25)
<223> OTHER INFORMATION: n represents inosine
<220> FEATURE:
<221> NAME/KEY: modified_base
<222> LOCATION: (26)..(26)
<223> OTHER INFORMATION: 7-deaza-G
<220> FEATURE:
<221> NAME/KEY: misc_feature
<222> LOCATION: (27)..(35)
<223> OTHER INFORMATION: n represents inosine
<220> FEATURE:
<221> NAME/KEY: modified_base
<222> LOCATION: (36)..(36)
<223> OTHER INFORMATION: 7-deaza-G
<220> FEATURE:
<221> NAME/KEY: misc_feature
<222> LOCATION: (37)..(45)
<223> OTHER INFORMATION: n represents inosine
<220> FEATURE:
<221> NAME/KEY: modified_base
<222> LOCATION: (46)..(46)
<223> OTHER INFORMATION: 7-deaza-G
<220> FEATURE:
<221> NAME/KEY: misc_feature
<222> LOCATION: (47)..(50)
<223> OTHER INFORMATION: n represents inosine

<400> SEQUENCE: 87
ugucaacugc cagugnnnnn nnnnngnnnn nnnnngnnnn nnnnngnnnn         50

<210> SEQ ID NO 88
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (20)..(20)
<223> OTHER INFORMATION: ara-C
<220> FEATURE:
<221> NAME/KEY: modified_base
<222> LOCATION: (30)..(30)
<223> OTHER INFORMATION: ara-C
<220> FEATURE:
<221> NAME/KEY: modified_base
<222> LOCATION: (40)..(40)
<223> OTHER INFORMATION: ara-C

<400> SEQUENCE: 88
cacuggcagu ugacaccccc cccccccccc cccccccccc cccccccccc         50

<210> SEQ ID NO 89

```
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(25)
<223> OTHER INFORMATION: n represents inosine
<220> FEATURE:
<221> NAME/KEY: misc_feature
<222> LOCATION: (27)..(35)
<223> OTHER INFORMATION: n represents inosine
<220> FEATURE:
<221> NAME/KEY: misc_feature
<222> LOCATION: (37)..(45)
<223> OTHER INFORMATION: n represents inosine
<220> FEATURE:
<221> NAME/KEY: misc_feature
<222> LOCATION: (47)..(50)
<223> OTHER INFORMATION: n represents inosine

<400> SEQUENCE: 89
ugucaacugc cagugnnnnn nnnnngnnnn nnnnngnnnn nnnnngnnnn         50

<210> SEQ ID NO 90
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 90
cacuggcagu ugacaccccc cccccccccc cccccccccc cccccccccc         50

<210> SEQ ID NO 91
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(25)
<223> OTHER INFORMATION: n represents inosine
<220> FEATURE:
<221> NAME/KEY: modified_base
<222> LOCATION: (26)..(26)
<223> OTHER INFORMATION: ara-G
<220> FEATURE:
<221> NAME/KEY: misc_feature
<222> LOCATION: (27)..(35)
<223> OTHER INFORMATION: n represents inosine
<220> FEATURE:
<221> NAME/KEY: modified_base
<222> LOCATION: (36)..(36)
<223> OTHER INFORMATION: ara-G
<220> FEATURE:
<221> NAME/KEY: misc_feature
<222> LOCATION: (37)..(45)
<223> OTHER INFORMATION: n represents inosine
<220> FEATURE:
<221> NAME/KEY: modified_base
<222> LOCATION: (46)..(46)
<223> OTHER INFORMATION: ara-G
<220> FEATURE:
<221> NAME/KEY: misc_feature
<222> LOCATION: (47)..(50)
<223> OTHER INFORMATION: n represents inosine

<400> SEQUENCE: 91
ugucaacugc cagugnnnnn nnnnngnnnn nnnnngnnnn nnnnngnnnn         50

<210> SEQ ID NO 92
```

```
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (20)..(20)
<223> OTHER INFORMATION: ara-C
<220> FEATURE:
<221> NAME/KEY: modified_base
<222> LOCATION: (30)..(30)
<223> OTHER INFORMATION: ara-C
<220> FEATURE:
<221> NAME/KEY: modified_base
<222> LOCATION: (40)..(40)
<223> OTHER INFORMATION: ara-C

<400> SEQUENCE: 92
cacuggcagu ugacaccccc cccccccccc cccccccccc cccccccccc          50

<210> SEQ ID NO 93
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(25)
<223> OTHER INFORMATION: n represents inosine
<220> FEATURE:
<221> NAME/KEY: modified_base
<222> LOCATION: (26)..(26)
<223> OTHER INFORMATION: ara-G
<220> FEATURE:
<221> NAME/KEY: misc_feature
<222> LOCATION: (27)..(35)
<223> OTHER INFORMATION: n represents inosine
<220> FEATURE:
<221> NAME/KEY: modified_base
<222> LOCATION: (36)..(36)
<223> OTHER INFORMATION: ara-G
<220> FEATURE:
<221> NAME/KEY: misc_feature
<222> LOCATION: (37)..(45)
<223> OTHER INFORMATION: n represents inosine
<220> FEATURE:
<221> NAME/KEY: modified_base
<222> LOCATION: (46)..(46)
<223> OTHER INFORMATION: ara-G
<220> FEATURE:
<221> NAME/KEY: misc_feature
<222> LOCATION: (47)..(50)
<223> OTHER INFORMATION: n represents inosine

<400> SEQUENCE: 93
ugucaacugc cagugnnnnn nnnnngnnnn nnnnngnnnn nnnnngnnnn          50

<210> SEQ ID NO 94
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (20)..(20)
<223> OTHER INFORMATION: 5-Me-C
<220> FEATURE:
<221> NAME/KEY: modified_base
<222> LOCATION: (30)..(30)
<223> OTHER INFORMATION: 5-Me-C
<220> FEATURE:
<221> NAME/KEY: modified_base
<222> LOCATION: (40)..(40)
```

<223> OTHER INFORMATION: 5-Me-C

<400> SEQUENCE: 94
cacuggcagu ugacacccccc cccccccccc cccccccccc cccccccccc          50

<210> SEQ ID NO 95
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 95
ugucaacugc cagugnnnnn nnnnnnnnnn nnnnnnnnnn nnnnnnnnnn          50

<210> SEQ ID NO 96
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(15)
<223> OTHER INFORMATION: 2'-OMe

<400> SEQUENCE: 96
cacuggcagu ugacacccccc cccccccccc cccccccccc cccccccccc          50

<210> SEQ ID NO 97
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 97
ugucaacugc cagugnnnnn nnnnnnnnnn nnnnnnnnnn nnnnnnnnnn          50

<210> SEQ ID NO 98
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(20)
<223> OTHER INFORMATION: 2'-OMe

<400> SEQUENCE: 98
cacuggcagu ugacacccccc cccccccccc cccccccccc cccccccccc          50

<210> SEQ ID NO 99
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)

<223> OTHER INFORMATION: n represents inosine

<400> SEQUENCE: 99
ugucaacugc cagugnnnnn nnnnnnnnnn nnnnnnnnnn nnnnnnnnnn            50

<210> SEQ ID NO 100
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (16)..(25)
<223> OTHER INFORMATION: 2'-OMe

<400> SEQUENCE: 100
cacuggcagu ugacaccccc cccccccccc cccccccccc cccccccccc            50

<210> SEQ ID NO 101
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 101
ugucaacugc cagugnnnnn nnnnnnnnnn nnnnnnnnnn nnnnnnnnnn            50

<210> SEQ ID NO 102
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (16)..(35)
<223> OTHER INFORMATION: 2'-OMe

<400> SEQUENCE: 102
cacuggcagu ugacaccccc cccccccccc cccccccccc cccccccccc            50

<210> SEQ ID NO 103
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 103
ugucaacugc cagugnnnnn nnnnnnnnnn nnnnnnnnnn nnnnnnnnnn            50

<210> SEQ ID NO 104
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (16)..(45)

<223> OTHER INFORMATION: 2'-OMe

<400> SEQUENCE: 104
cacuggcagu ugacacccccc cccccccccc cccccccccc cccccccccc    50

<210> SEQ ID NO 105
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 105
ugucaacugc cagugnnnnn nnnnnnnnnn nnnnnnnnnn nnnnnnnnnn    50

<210> SEQ ID NO 106
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 106
cacuggcagu ugacacccccc cccccccccc cccccccccc cccccccccc    50

<210> SEQ ID NO 107
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(15)
<223> OTHER INFORMATION: 2'-OMe
<220> FEATURE:
<221> NAME/KEY: misc_feature
<222> LOCATION: (16)..(50)
<223> OTHER INFORMATION: n represents inosine

<400> SEQUENCE: 107
ugucaacugc cagugnnnnn nnnnnnnnnn nnnnnnnnnn nnnnnnnnnn    50

<210> SEQ ID NO 108
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(15)
<223> OTHER INFORMATION: 2'-OMe

<400> SEQUENCE: 108
cacuggcagu ugacacccccc cccccccccc cccccccccc cccccccccc    50

<210> SEQ ID NO 109
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(15)

```
<223> OTHER INFORMATION: 2'-OMe
<220> FEATURE:
<221> NAME/KEY: misc_feature
<222> LOCATION: (16)..(50)
<223> OTHER INFORMATION: n represents inosine

<400> SEQUENCE: 109
ugucaacugc cagugnnnnn nnnnnnnnnn nnnnnnnnnn nnnnnnnnnn         50

<210> SEQ ID NO 110
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 110
cacuggcagu ugacacccccc ccccccccc ccccccccc cccccccccc         50

<210> SEQ ID NO 111
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 111
ugucaacugc cagugnnnnn nnnnnnnnnn nnnnnnnnnn nnnnnnnnnn         50

<210> SEQ ID NO 112
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 112
cacuggcagu ugacaccccu ccccccccu ccccccccu cccccccccc         50

<210> SEQ ID NO 113
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 113
ugucaacugc cagugnnnnn nnnnnnnnnn nnnnnnnnnn nnnnnnnnnn         50

<210> SEQ ID NO 114
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 114
cacuggcagu ugacacccccc ccccccccc ccccccccc cccccccccc         50

<210> SEQ ID NO 115
```

```
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(25)
<223> OTHER INFORMATION: n represents inosine
<220> FEATURE:
<221> NAME/KEY: misc_feature
<222> LOCATION: (27)..(35)
<223> OTHER INFORMATION: n represents inosine
<220> FEATURE:
<221> NAME/KEY: misc_feature
<222> LOCATION: (37)..(45)
<223> OTHER INFORMATION: n represents inosine
<220> FEATURE:
<221> NAME/KEY: misc_feature
<222> LOCATION: (47)..(50)
<223> OTHER INFORMATION: n represents inosine

<400> SEQUENCE: 115
ugucaacugc cagugnnnnn nnnnnannnn nnnnnannnn nnnnnannnn          50

<210> SEQ ID NO 116
<211> LENGTH: 15
<212> TYPE: RNA
<213> ORGANISM: Artificial Sequence
<220> FEATURE:
<223> OTHER INFORMATION: Synthetic oligonucleotide

<400> SEQUENCE: 116
cacuggcagu ugaca                                                15

<210> SEQ ID NO 117
<211> LENGTH: 15
<212> TYPE: RNA
<213> ORGANISM: Artificial Sequence
<220> FEATURE:
<223> OTHER INFORMATION: Synthetic oligonucleotide

<400> SEQUENCE: 117
ugucaacugc cagug                                                15

<210> SEQ ID NO 118
<211> LENGTH: 15
<212> TYPE: RNA
<213> ORGANISM: Artificial Sequence
<220> FEATURE:
<223> OTHER INFORMATION: Synthetic oligonucleotide

<400> SEQUENCE: 118
cacuggcagu ugaca                                                15

<210> SEQ ID NO 119
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 119
ugucaacugc cagugnnnnn nnnnnnnnnn nnnnnnnnnn nnnnnnnnnn          50

<210> SEQ ID NO 120
```

```
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 120
cacuggcagu ugacaccccc cccccccccc cccccccccc cccccccccc          50

<210> SEQ ID NO 121
<211> LENGTH: 15
<212> TYPE: RNA
<213> ORGANISM: Artificial Sequence
<220> FEATURE:
<223> OTHER INFORMATION: Synthetic oligonucleotide

<400> SEQUENCE: 121
ugucaacugc cagug                                                15

<210> SEQ ID NO 122
<211> LENGTH: 15
<212> TYPE: RNA
<213> ORGANISM: Artificial Sequence
<220> FEATURE:
<223> OTHER INFORMATION: Synthetic oligonucleotide

<400> SEQUENCE: 122
cacuggcagu ugaca                                                15

<210> SEQ ID NO 123
<211> LENGTH: 15
<212> TYPE: RNA
<213> ORGANISM: Artificial Sequence
<220> FEATURE:
<223> OTHER INFORMATION: Synthetic oligonucleotide

<400> SEQUENCE: 123
ugucaacugc cagug                                                15

<210> SEQ ID NO 124
<211> LENGTH: 45
<212> TYPE: RNA
<213> ORGANISM: Artificial Sequence
<220> FEATURE:
<223> OTHER INFORMATION: Synthetic oligonucleotide

<400> SEQUENCE: 124
cacuggcagu ugacacacug gcaguugaca cacuggcagu ugaca               45

<210> SEQ ID NO 125
<211> LENGTH: 45
<212> TYPE: RNA
<213> ORGANISM: Artificial Sequence
<220> FEATURE:
<223> OTHER INFORMATION: Synthetic oligonucleotide

<400> SEQUENCE: 125
ugucaacugc caguguguca acugccagug ugucaacugc cagug               45

<210> SEQ ID NO 126
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 126
```

```
cccccccccc cccccccccc cccccccccc ccccccacug gcaguugaca          50
```

<210> SEQ ID NO 127
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 127

```
ugucaacugc cagugnnnnn nnnnnnnnnn nnnnnnnnnn nnnnnnnnnn          50
```

<210> SEQ ID NO 128
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 128

```
ugucaacugc cagugccccc cccccccccc cccccccccc cccccccccc          50
```

<210> SEQ ID NO 129
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 129

```
cacuggcagu ugacaccccc cccccccccc cccccccccc cccccccccc          50
```

<210> SEQ ID NO 130
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 130

```
cacuggcagu ugacannnnn nnnnnnnnnn nnnnnnnnnn nnnnnnnnnn          50
```

<210> SEQ ID NO 131
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 131

```
ugucaacugc cagugnnnnn nnnnnnnnnn nnnnnnnnnn nnnnnnnnnn          50
```

<210> SEQ ID NO 132
<211> LENGTH: 50
<212> TYPE: RNA
<213> ORGANISM: Artificial Sequence
<220> FEATURE:

<223> OTHER INFORMATION: Synthetic oligonucleotide

<400> SEQUENCE: 132
caaggcaagc auucgccccc cccccccccc cccccccccc          50

<210> SEQ ID NO 133
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 133
cgaaugcuug ccuugnnnnn nnnnnnnnnn nnnnnnnnnn          50

<210> SEQ ID NO 134
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 134
gcuacuguuc gucgucccccc cccccccccc cccccccccc          50

<210> SEQ ID NO 135
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(35)
<223> OTHER INFORMATION: n represents inosine

<400> SEQUENCE: 135
nnnnnnnnnn nnnnnnnnnn nnnnnnnnnn nnnnncgaug acaagcagca          50

<210> SEQ ID NO 136
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 136
gaagucagua gucucccccc cccccccccc cccccccccc          50

<210> SEQ ID NO 137
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 137
gagacuacug acuucnnnnn nnnnnnnnnn nnnnnnnnnn          50

<210> SEQ ID NO 138

```
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 138
cacugagacu gaugcccccc cccccccccc cccccccccc cccccccccc        50

<210> SEQ ID NO 139
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 139
gcaucagucu cagugnnnnn nnnnnnnnnn nnnnnnnnnn nnnnnnnnnn        50

<210> SEQ ID NO 140
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 140
uacagcaguc agucccccc cccccccccc cccccccccc cccccccccc         50

<210> SEQ ID NO 141
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 141
agacugacug cuguannnnn nnnnnnnnnn nnnnnnnnnn nnnnnnnnnn        50

<210> SEQ ID NO 142
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 142
cgaugacuga cuacccccc cccccccccc cccccccccc cccccccccc         50

<210> SEQ ID NO 143
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(35)
<223> OTHER INFORMATION: n represents inosine

<400> SEQUENCE: 143
```

```
nnnnnnnnnn nnnnnnnnnn nnnnnnnnnn nnnnngcuac ugacugaugc          50

<210> SEQ ID NO 144
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 144
ccccggccgc cgcccccccc cccccccccc cccccccccc cccccccccc          50

<210> SEQ ID NO 145
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n represents inosine
<220> FEATURE:
<221> NAME/KEY: misc_feature
<222> LOCATION: (3)..(3)
<223> OTHER INFORMATION: n represents inosine
<220> FEATURE:
<221> NAME/KEY: misc_feature
<222> LOCATION: (5)..(6)
<223> OTHER INFORMATION: n represents inosine
<220> FEATURE:
<221> NAME/KEY: misc_feature
<222> LOCATION: (8)..(8)
<223> OTHER INFORMATION: n represents inosine
<220> FEATURE:
<221> NAME/KEY: misc_feature
<222> LOCATION: (12)..(12)
<223> OTHER INFORMATION: n represents inosine
<220> FEATURE:
<221> NAME/KEY: misc_feature
<222> LOCATION: (14)..(14)
<223> OTHER INFORMATION: n represents inosine
<220> FEATURE:
<221> NAME/KEY: misc_feature
<222> LOCATION: (16)..(50)
<223> OTHER INFORMATION: n represents inosine

<400> SEQUENCE: 145
ngncnncngc cngngnnnnn nnnnnnnnnn nnnnnnnnnn nnnnnnnnnn          50

<210> SEQ ID NO 146
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 146
gccccgcccc gccccccccc cccccccccc cccccccccc cccccccccc          50

<210> SEQ ID NO 147
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: n represents inosine
<220> FEATURE:
<221> NAME/KEY: misc_feature
<222> LOCATION: (4)..(4)
```

```
<223> OTHER INFORMATION: n represents inosine
<220> FEATURE:
<221> NAME/KEY: misc_feature
<222> LOCATION: (7)..(7)
<223> OTHER INFORMATION: n represents inosine
<220> FEATURE:
<221> NAME/KEY: misc_feature
<222> LOCATION: (9)..(9)
<223> OTHER INFORMATION: n represents inosine
<220> FEATURE:
<221> NAME/KEY: misc_feature
<222> LOCATION: (12)..(12)
<223> OTHER INFORMATION: n represents inosine
<220> FEATURE:
<221> NAME/KEY: misc_feature
<222> LOCATION: (14)..(14)
<223> OTHER INFORMATION: n represents inosine
<220> FEATURE:
<221> NAME/KEY: misc_feature
<222> LOCATION: (16)..(50)
<223> OTHER INFORMATION: n represents inosine

<400> SEQUENCE: 147
nngncgngnc gngncnnnnn nnnnnnnnnn nnnnnnnnnn nnnnnnnnnn          50

<210> SEQ ID NO 148
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 148
cacugcucau ucacaccccc ccccccccccc ccccccccc cccccccccc           50

<210> SEQ ID NO 149
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(20)
<223> OTHER INFORMATION: n represents inosine
<220> FEATURE:
<221> NAME/KEY: modified_base
<222> LOCATION: (21)..(21)
<223> OTHER INFORMATION: 7-deaza-G
<220> FEATURE:
<221> NAME/KEY: misc_feature
<222> LOCATION: (22)..(30)
<223> OTHER INFORMATION: n represents inosine
<220> FEATURE:
<221> NAME/KEY: modified_base
<222> LOCATION: (31)..(31)
<223> OTHER INFORMATION: 7-deaza-G
<220> FEATURE:
<221> NAME/KEY: misc_feature
<222> LOCATION: (32)..(40)
<223> OTHER INFORMATION: n represents inosine
<220> FEATURE:
<221> NAME/KEY: modified_base
<222> LOCATION: (41)..(41)
<223> OTHER INFORMATION: 7-deaza-G
<220> FEATURE:
<221> NAME/KEY: misc_feature
<222> LOCATION: (42)..(50)
<223> OTHER INFORMATION: n represents inosine

<400> SEQUENCE: 149
ugugaaugag cagugnnnnn gnnnnnnnnn gnnnnnnnnn gnnnnnnnnn           50

<210> SEQ ID NO 150
```

```
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 150
uacagcaguc agucccccc cccccccccc cccccccccc cccccccccc         50

<210> SEQ ID NO 151
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(5)
<223> OTHER INFORMATION: n represents inosine
<220> FEATURE:
<221> NAME/KEY: modified_base
<222> LOCATION: (6)..(6)
<223> OTHER INFORMATION: 7-deaza-G
<220> FEATURE:
<221> NAME/KEY: misc_feature
<222> LOCATION: (7)..(15)
<223> OTHER INFORMATION: n represents inosine
<220> FEATURE:
<221> NAME/KEY: modified_base
<222> LOCATION: (16)..(16)
<223> OTHER INFORMATION: 7-deaza-G
<220> FEATURE:
<221> NAME/KEY: misc_feature
<222> LOCATION: (17)..(25)
<223> OTHER INFORMATION: n represents inosine
<220> FEATURE:
<221> NAME/KEY: modified_base
<222> LOCATION: (26)..(26)
<223> OTHER INFORMATION: 7-deaza-G
<220> FEATURE:
<221> NAME/KEY: misc_feature
<222> LOCATION: (27)..(35)
<223> OTHER INFORMATION: n represents inosine

<400> SEQUENCE: 151
nnnnngnnnn nnnnngnnnn nnnnngnnnn nnnnnauguc gucagucaga         50

<210> SEQ ID NO 152
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 152
cgaugacuga cuacgccccc cccccccccc cccccccccc cccccccccc         50

<210> SEQ ID NO 153
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: n represents inosine
<220> FEATURE:
<221> NAME/KEY: modified_base
<222> LOCATION: (9)..(9)
<223> OTHER INFORMATION: 7-deaza-G
<220> FEATURE:
<221> NAME/KEY: misc_feature
<222> LOCATION: (10)..(17)
```

```
<223> OTHER INFORMATION: n represents inosine
<220> FEATURE:
<221> NAME/KEY: modified_base
<222> LOCATION: (18)..(18)
<223> OTHER INFORMATION: 7-deaza-G
<220> FEATURE:
<221> NAME/KEY: misc_feature
<222> LOCATION: (19)..(26)
<223> OTHER INFORMATION: n represents inosine
<220> FEATURE:
<221> NAME/KEY: modified_base
<222> LOCATION: (27)..(27)
<223> OTHER INFORMATION: 7-deaza-G
<220> FEATURE:
<221> NAME/KEY: misc_feature
<222> LOCATION: (28)..(35)
<223> OTHER INFORMATION: n represents inosine

<400> SEQUENCE: 153
nnnnnnnngn nnnnnnngnn nnnnnngnnn nnnnngcuac ugacugaugc         50

<210> SEQ ID NO 154
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 154
cacugagacu gaugcccccc cccccccccc cccccccccc cccccccccc         50

<210> SEQ ID NO 155
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(5)
<223> OTHER INFORMATION: n represents inosine
<220> FEATURE:
<221> NAME/KEY: modified_base
<222> LOCATION: (6)..(6)
<223> OTHER INFORMATION: 7-deaza-G
<220> FEATURE:
<221> NAME/KEY: misc_feature
<222> LOCATION: (7)..(15)
<223> OTHER INFORMATION: n represents inosine
<220> FEATURE:
<221> NAME/KEY: modified_base
<222> LOCATION: (16)..(16)
<223> OTHER INFORMATION: 7-deaza-G
<220> FEATURE:
<221> NAME/KEY: misc_feature
<222> LOCATION: (17)..(25)
<223> OTHER INFORMATION: n represents inosine
<220> FEATURE:
<221> NAME/KEY: modified_base
<222> LOCATION: (26)..(26)
<223> OTHER INFORMATION: 7-deaza-G
<220> FEATURE:
<221> NAME/KEY: misc_feature
<222> LOCATION: (27)..(35)
<223> OTHER INFORMATION: n represents inosine

<400> SEQUENCE: 155
nnnnngnnnn nnnnngnnnn nnnnngnnnn nnnnngugac ucugacuacg         50

<210> SEQ ID NO 156
<211> LENGTH: 50
<212> TYPE: RNA
<213> ORGANISM: Artificial Sequence
<220> FEATURE:
```

<223> OTHER INFORMATION: Synthetic oligonucleotide

<400> SEQUENCE: 156
caaggcaagc auucgccccc cccccccccc cccccccccc          50

<210> SEQ ID NO 157
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: n represents inosine
<220> FEATURE:
<221> NAME/KEY: modified_base
<222> LOCATION: (9)..(9)
<223> OTHER INFORMATION: 7-deaza-G
<220> FEATURE:
<221> NAME/KEY: misc_feature
<222> LOCATION: (10)..(17)
<223> OTHER INFORMATION: n represents inosine
<220> FEATURE:
<221> NAME/KEY: modified_base
<222> LOCATION: (18)..(18)
<223> OTHER INFORMATION: 7-deaza-G
<220> FEATURE:
<221> NAME/KEY: misc_feature
<222> LOCATION: (19)..(26)
<223> OTHER INFORMATION: n represents inosine
<220> FEATURE:
<221> NAME/KEY: modified_base
<222> LOCATION: (27)..(27)
<223> OTHER INFORMATION: 7-deaza-G
<220> FEATURE:
<221> NAME/KEY: misc_feature
<222> LOCATION: (28)..(35)
<223> OTHER INFORMATION: n represents inosine

<400> SEQUENCE: 157
nnnnnnnngn nnnnnnngnn nnnnnngnnn nnnnnguucc guucguaagc          50

<210> SEQ ID NO 158
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (25)..(25)
<223> OTHER INFORMATION: 5-methyl-cytidine
<220> FEATURE:
<221> NAME/KEY: modified_base
<222> LOCATION: (35)..(35)
<223> OTHER INFORMATION: 5-methyl-cytidine
<220> FEATURE:
<221> NAME/KEY: modified_base
<222> LOCATION: (45)..(45)
<223> OTHER INFORMATION: 5-methyl-cytidine

<400> SEQUENCE: 158
cacugcucau ucacacccccc cccccccccc cccccccccc          50

<210> SEQ ID NO 159
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(20)

```
<223> OTHER INFORMATION: n represents inosine
<220> FEATURE:
<221> NAME/KEY: misc_feature
<222> LOCATION: (22)..(30)
<223> OTHER INFORMATION: n represents inosine
<220> FEATURE:
<221> NAME/KEY: misc_feature
<222> LOCATION: (32)..(40)
<223> OTHER INFORMATION: n represents inosine
<220> FEATURE:
<221> NAME/KEY: misc_feature
<222> LOCATION: (42)..(50)
<223> OTHER INFORMATION: n represents inosine

<400> SEQUENCE: 159
ugugaaugag cagugnnnnn gnnnnnnnnn gnnnnnnnnn gnnnnnnnnn          50

<210> SEQ ID NO 160
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (21)..(21)
<223> OTHER INFORMATION: 5-methyl-cytidine
<220> FEATURE:
<221> NAME/KEY: modified_base
<222> LOCATION: (31)..(31)
<223> OTHER INFORMATION: 5-methyl-cytidine
<220> FEATURE:
<221> NAME/KEY: modified_base
<222> LOCATION: (41)..(41)
<223> OTHER INFORMATION: 5-methyl-cytidine

<400> SEQUENCE: 160
uacagcaguc agucccccc cccccccccc cccccccccc cccccccccc          50

<210> SEQ ID NO 161
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 161
agacugacug cguannnnn nnnnnnnnnn nnnnnnnnnn nnnnnnnnnn          50

<210> SEQ ID NO 162
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (24)..(24)
<223> OTHER INFORMATION: 5-methyl-cytidine
<220> FEATURE:
<221> NAME/KEY: modified_base
<222> LOCATION: (33)..(33)
<223> OTHER INFORMATION: 5-methyl-cytidine
<220> FEATURE:
<221> NAME/KEY: modified_base
<222> LOCATION: (42)..(42)
<223> OTHER INFORMATION: 5-methyl-cytidine

<400> SEQUENCE: 162
```
cgaugacuga cuacgccccc cccccccccc cccccccccc cccccccccc    50

<210> SEQ ID NO 163
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(35)
<223> OTHER INFORMATION: n represents inosine

<400> SEQUENCE: 163
nnnnnnnnnn nnnnnnnnnn nnnnnnnnnn nnnnngcuac ugacugaugc    50

<210> SEQ ID NO 164
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (21)..(21)
<223> OTHER INFORMATION: 5-methyl-cytidine
<220> FEATURE:
<221> NAME/KEY: modified_base
<222> LOCATION: (31)..(31)
<223> OTHER INFORMATION: 5-methyl-cytidine
<220> FEATURE:
<221> NAME/KEY: modified_base
<222> LOCATION: (41)..(41)
<223> OTHER INFORMATION: 5-methyl-cytidine

<400> SEQUENCE: 164
cacugagacu gaugccccccc cccccccccc cccccccccc cccccccccc    50

<210> SEQ ID NO 165
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 165
gcaucagucu cagugnnnnn nnnnnnnnnn nnnnnnnnnn nnnnnnnnnn    50

<210> SEQ ID NO 166
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (24)..(24)
<223> OTHER INFORMATION: 5-methyl-cytidine
<220> FEATURE:
<221> NAME/KEY: modified_base
<222> LOCATION: (33)..(33)
<223> OTHER INFORMATION: 5-methyl-cytidine
<220> FEATURE:
<221> NAME/KEY: modified_base
<222> LOCATION: (42)..(42)
<223> OTHER INFORMATION: 5-methyl-cytidine

<400> SEQUENCE: 166
caaggcaagc auucgccccc cccccccccc cccccccccc cccccccccc                    50

<210> SEQ ID NO 167
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 167
cgaaugcuug ccuugnnnnn nnnnnnnnnn nnnnnnnnnn nnnnnnnnnn                    50

<210> SEQ ID NO 168
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (21)..(21)
<223> OTHER INFORMATION: 5-methyl-cytidine
<220> FEATURE:
<221> NAME/KEY: modified_base
<222> LOCATION: (27)..(27)
<223> OTHER INFORMATION: 5-methyl-cytidine
<220> FEATURE:
<221> NAME/KEY: modified_base
<222> LOCATION: (33)..(33)
<223> OTHER INFORMATION: 5-methyl-cytidine
<220> FEATURE:
<221> NAME/KEY: modified_base
<222> LOCATION: (39)..(39)
<223> OTHER INFORMATION: 5-methyl-cytidine
<220> FEATURE:
<221> NAME/KEY: modified_base
<222> LOCATION: (45)..(45)
<223> OTHER INFORMATION: 5-methyl-cytidine

<400> SEQUENCE: 168
cacuggcagu ugacaccccc cccccccccc cccccccccc cccccccccc                    50

<210> SEQ ID NO 169
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 169
ugucaacugc cagugnnnnn nnnnnnnnnn nnnnnnnnnn nnnnnnnnnn                    50

<210> SEQ ID NO 170
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (25)..(25)
<223> OTHER INFORMATION: 2'-OMe
<220> FEATURE:
<221> NAME/KEY: modified_base
<222> LOCATION: (35)..(35)

```
<223> OTHER INFORMATION: 2'-OMe
<220> FEATURE:
<221> NAME/KEY: modified_base
<222> LOCATION: (45)..(45)
<223> OTHER INFORMATION: 2'-OMe

<400> SEQUENCE: 170
cacuggcagu ugacaccccc cccccccccc cccccccccc cccccccccc         50

<210> SEQ ID NO 171
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 171
ugucaacugc cagugnnnnn nnnnnnnnnn nnnnnnnnnn nnnnnnnnnn         50

<210> SEQ ID NO 172
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(1)
<223> OTHER INFORMATION: 2'-OMe
<220> FEATURE:
<221> NAME/KEY: modified_base
<222> LOCATION: (7)..(7)
<223> OTHER INFORMATION: 2'-OMe
<220> FEATURE:
<221> NAME/KEY: modified_base
<222> LOCATION: (14)..(14)
<223> OTHER INFORMATION: 2'-OMe

<400> SEQUENCE: 172
cacuggcagu ugacaccccc cccccccccc cccccccccc cccccccccc         50

<210> SEQ ID NO 173
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 173
ugucaacugc cagugnnnnn nnnnnnnnnn nnnnnnnnnn nnnnnnnnnn         50

<210> SEQ ID NO 174
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 174
guccucagcg auagccccccc cccccccccc cccccccccc cccccccccc        50

<210> SEQ ID NO 175
```

```
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 175
gcuaucgcug aggacnnnnn nnnnnnnnnn nnnnnnnnnn nnnnnnnnnn          50

<210> SEQ ID NO 176
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 176
caucgcuccu cuccaccccc ccccccccc ccccccccc ccccccccc              50

<210> SEQ ID NO 177
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(35)
<223> OTHER INFORMATION: n represents inosine

<400> SEQUENCE: 177
nnnnnnnnnn nnnnnnnnnn nnnnnnnnnn nnnnnguagc gaggagaggu          50

<210> SEQ ID NO 178
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 178
cucuaccguu cgcuccccccc ccccccccc ccccccccc ccccccccc             50

<210> SEQ ID NO 179
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(35)
<223> OTHER INFORMATION: n represents inosine

<400> SEQUENCE: 179
nnnnnnnnnn nnnnnnnnnn nnnnnnnnnn nnnnngagau ggcaagcgag          50

<210> SEQ ID NO 180
<211> LENGTH: 48
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(16)
```

```
<223> OTHER INFORMATION: n represents hexaethylene glycol

<400> SEQUENCE: 180
cacuggcagu ugacancccc cccccccccc cccccccccc ccccccc              48

<210> SEQ ID NO 181
<211> LENGTH: 48
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(33)
<223> OTHER INFORMATION: n represents inosine
<220> FEATURE:
<221> NAME/KEY: misc_feature
<222> LOCATION: (34)..(34)
<223> OTHER INFORMATION: n represents hexaethylene glycol

<400> SEQUENCE: 181
nnnnnnnnnn nnnnnnnnnn nnnnnnnnnn nnngugaccg ucaacugu              48

<210> SEQ ID NO 182
<211> LENGTH: 53
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(16)
<223> OTHER INFORMATION: n represents hexaethylene glycol
<220> FEATURE:
<221> NAME/KEY: misc_feature
<222> LOCATION: (27)..(27)
<223> OTHER INFORMATION: n represents hexaethylene glycol
<220> FEATURE:
<221> NAME/KEY: misc_feature
<222> LOCATION: (38)..(38)
<223> OTHER INFORMATION: n represents hexaethylene glycol

<400> SEQUENCE: 182
cacuggcagu ugacancccc cccccncccc cccccccncc cccccccccc ccc              53

<210> SEQ ID NO 183
<211> LENGTH: 52
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(10)
<223> OTHER INFORMATION: n represents inosine
<220> FEATURE:
<221> NAME/KEY: misc_feature
<222> LOCATION: (11)..(11)
<223> OTHER INFORMATION: n represents hexaethylene glycol
<220> FEATURE:
<221> NAME/KEY: misc_feature
<222> LOCATION: (12)..(21)
<223> OTHER INFORMATION: n represents inosine
<220> FEATURE:
<221> NAME/KEY: misc_feature
<222> LOCATION: (22)..(22)
<223> OTHER INFORMATION: n represents hexaethylene glycol
<220> FEATURE:
<221> NAME/KEY: misc_feature
<222> LOCATION: (23)..(37)
<223> OTHER INFORMATION: n represents inosine

<400> SEQUENCE: 183
```

```
nnnnnnnnnn nnnnnnnnnn nnnnnnnnnn nnnnnnngug accgucaacu gu        52
```

<210> SEQ ID NO 184
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(3)
<223> OTHER INFORMATION: 2'-OMe

<400> SEQUENCE: 184

```
cacuggcagu ugacaccccc cccccccccc cccccccccc cccccccccc          50
```

<210> SEQ ID NO 185
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 185

```
ugucaacugc cagugnnnnn nnnnnnnnnn nnnnnnnnnn nnnnnnnnnn          50
```

<210> SEQ ID NO 186
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (5)..(8)
<223> OTHER INFORMATION: 2'-OMe

<400> SEQUENCE: 186

```
cacuggcagu ugacaccccc cccccccccc cccccccccc cccccccccc          50
```

<210> SEQ ID NO 187
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 187

```
ugucaacugc cagugnnnnn nnnnnnnnnn nnnnnnnnnn nnnnnnnnnn          50
```

<210> SEQ ID NO 188
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (12)..(15)
<223> OTHER INFORMATION: 2'-OMe

<400> SEQUENCE: 188

-continued cacuggcagu ugacacccccc ccccccccc ccccccccc    50

<210> SEQ ID NO 189
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 189
ugucaacugc cagugnnnnn nnnnnnnnnn nnnnnnnnn nnnnnnnnn    50

<210> SEQ ID NO 190
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (13)..(18)
<223> OTHER INFORMATION: 2'-OMe

<400> SEQUENCE: 190
cacuggcagu ugacacccccc ccccccccc ccccccccc    50

<210> SEQ ID NO 191
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 191
ugucaacugc cagugnnnnn nnnnnnnnnn nnnnnnnnn nnnnnnnnn    50

<210> SEQ ID NO 192
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (16)..(19)
<223> OTHER INFORMATION: 2'-OMe

<400> SEQUENCE: 192
cacuggcagu ugacacccccc ccccccccc ccccccccc    50

<210> SEQ ID NO 193
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 193
ugucaacugc cagugnnnnn nnnnnnnnnn nnnnnnnnnn nnnnnnnnnn                50

<210> SEQ ID NO 194
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (22)..(25)
<223> OTHER INFORMATION: 2'-OMe

<400> SEQUENCE: 194
cacuggcagu ugacacccccc cccccccccc cccccccccc cccccccccc                50

<210> SEQ ID NO 195
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 195
ugucaacugc cagugnnnnn nnnnnnnnnn nnnnnnnnnn nnnnnnnnnn                50

<210> SEQ ID NO 196
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (26)..(30)
<223> OTHER INFORMATION: 2'-OMe

<400> SEQUENCE: 196
cacuggcagu ugacacccccc cccccccccc cccccccccc cccccccccc                50

<210> SEQ ID NO 197
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 197
ugucaacugc cagugnnnnn nnnnnnnnnn nnnnnnnnnn nnnnnnnnnn                50

<210> SEQ ID NO 198
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (29)..(33)
<223> OTHER INFORMATION: 2'-OMe

<400> SEQUENCE: 198
cacuggcagu ugacacccccc ccccccccccc ccccccccc cccccccccc         50

<210> SEQ ID NO 199
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 199
ugucaacugc cagugnnnnn nnnnnnnnnn nnnnnnnnnn nnnnnnnnnn         50

<210> SEQ ID NO 200
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (38)..(41)
<223> OTHER INFORMATION: 2'-OMe

<400> SEQUENCE: 200
cacuggcagu ugacacccccc ccccccccccc ccccccccc cccccccccc         50

<210> SEQ ID NO 201
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 201
ugucaacugc cagugnnnnn nnnnnnnnnn nnnnnnnnnn nnnnnnnnnn         50

<210> SEQ ID NO 202
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (41)..(45)
<223> OTHER INFORMATION: 2'-OMe

<400> SEQUENCE: 202
cacuggcagu ugacacccccc ccccccccccc ccccccccc cccccccccc         50

<210> SEQ ID NO 203
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 203
ugucaacugc cagugnnnnn nnnnnnnnnn nnnnnnnnnn nnnnnnnnnn          50

<210> SEQ ID NO 204
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (47)..(50)
<223> OTHER INFORMATION: 2'-OMe

<400> SEQUENCE: 204
cacuggcagu ugacacccccc ccccccccccc ccccccccc ccccccccc          50

<210> SEQ ID NO 205
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 205
ugucaacugc cagugnnnnn nnnnnnnnnn nnnnnnnnnn nnnnnnnnnn          50

<210> SEQ ID NO 206
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 206
cacuggcagu ugacacccccc ccccccccccc ccccccccc ccccccccc          50

<210> SEQ ID NO 207
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 207
ugucaacugc cagugnnnnn nnnnnnnnnn nnnnnnnnnn nnnnnnnnnn          50

<210> SEQ ID NO 208
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 208
cacuggcagu ugacacccccc ccccccccccc ccccccccc ccccccccc          50

<210> SEQ ID NO 209
<211> LENGTH: 50
<212> TYPE: RNA
<213> ORGANISM: Artificial Sequence
<220> FEATURE:

-continued

```
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 209
ugucaacugc cagugnnnnn nnnnnnnnnn nnnnnnnnnn nnnnnnnnnn          50

<210> SEQ ID NO 210
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 210
cacuggcagu ugacacccccc cccccccccc cccccccccc cccccccccc          50

<210> SEQ ID NO 211
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 211
ugucaacugc cagugnnnnn nnnnnnnnnn nnnnnnnnnn nnnnnnnnnn          50

<210> SEQ ID NO 212
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 212
cacuggcagu ugacacccccc cccccccccc cccccccccc cccccccccc          50

<210> SEQ ID NO 213
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 213
ugucaacugc cagugnnnnn nnnnnnnnnn nnnnnnnnnn nnnnnnnnnn          50

<210> SEQ ID NO 214
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 214
cacuggcagu ugacacccccc cccccccccc cccccccccc cccccccccc          50

<210> SEQ ID NO 215
```

```
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 215
ugucaacugc cagugnnnnn nnnnnnnnnn nnnnnnnnnn nnnnnnnnnn        50

<210> SEQ ID NO 216
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 216
cacuggcagu ugacacccccc cccccccccc cccccccccc cccccccccc        50

<210> SEQ ID NO 217
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 217
ugucaacugc cagugnnnnn nnnnnnnnnn nnnnnnnnnn nnnnnnnnnn        50

<210> SEQ ID NO 218
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 218
cacuggcagu ugacaccccc cccccccccc cccccccccc cccccccccc        50

<210> SEQ ID NO 219
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 219
ugucaacugc cagugnnnnn nnnnnnnnnn nnnnnnnnnn nnnnnnnnnn        50

<210> SEQ ID NO 220
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 220
```
cacuggcagu ugacaccccc ccccccccc ccccccccc ccccccccc        50

<210> SEQ ID NO 221
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 221
ugucaacugc cagugnnnnn nnnnnnnnnn nnnnnnnnnn nnnnnnnnnn        50

<210> SEQ ID NO 222
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 222
cacuggcagu ugacaccccc ccccccccc ccccccccc ccccccccc        50

<210> SEQ ID NO 223
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 223
ugucaacugc cagugnnnnn nnnnnnnnnn nnnnnnnnnn nnnnnnnnnn        50

<210> SEQ ID NO 224
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 224 ccccccccc ccccccccc ccccccccc ccccccacug gcaguugaca        50

<210> SEQ ID NO 225
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(35)
<223> OTHER INFORMATION: n represents inosine

<400> SEQUENCE: 225
nnnnnnnnnn nnnnnnnnnn nnnnnnnnnn nnnnnuguca acugccagug        50

<210> SEQ ID NO 226
<211> LENGTH: 50
<212> TYPE: RNA
<213> ORGANISM: Artificial Sequence
<220> FEATURE:

```
<223> OTHER INFORMATION: Synthetic oligonucleotide

<400> SEQUENCE: 226
cccccccccc cccccccac uggcaguuga cacccccccc cccccccccc          50

<210> SEQ ID NO 227
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 227
ugucaacugc cagugnnnnn nnnnnnnnnn nnnnnnnnnn nnnnnnnnnn          50

<210> SEQ ID NO 228
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 228
cacuggcagu ugacauuuuu uuuuuuuuuu uuuuuuuuuu uuuuuuuuuu          50

<210> SEQ ID NO 229
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 229
ugucaacugc cagugnnnnn nnnnnnnnnn nnnnnnnnnn nnnnnnnnnn          50

<210> SEQ ID NO 230
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 230
cacuggcagu ugacaaaaaa aaaaaaaaaa aaaaaaaaaa aaaaaaaaaa          50

<210> SEQ ID NO 231
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 231
ugucaacugc cagugnnnnn nnnnnnnnnn nnnnnnnnnn nnnnnnnnnn          50

<210> SEQ ID NO 232
```

```
<211> LENGTH: 10
<212> TYPE: RNA
<213> ORGANISM: Artificial Sequence
<220> FEATURE:
<223> OTHER INFORMATION: Synthetic oligonucleotide

<400> SEQUENCE: 232
acacccccc                                                                 10

<210> SEQ ID NO 233
<211> LENGTH: 10
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(10)
<223> OTHER INFORMATION: n represents inosine

<400> SEQUENCE: 233 ugunnnnnnn                                                                10

<210> SEQ ID NO 234
<211> LENGTH: 20
<212> TYPE: RNA
<213> ORGANISM: Artificial Sequence
<220> FEATURE:
<223> OTHER INFORMATION: Synthetic oligonucleotide

<400> SEQUENCE: 234 acacccccc ccccccccc                                                       20

<210> SEQ ID NO 235
<211> LENGTH: 20
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(20)
<223> OTHER INFORMATION: n represents inosine

<400> SEQUENCE: 235
ugunnnnnnn nnnnnnnnnn                                                     20

<210> SEQ ID NO 236
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 236 ccccccccc ccccccccc ccccccccc ccccccccc ccccccccc                         50

<210> SEQ ID NO 237
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(50)
<223> OTHER INFORMATION: n represents inosine

<400> SEQUENCE: 237
```

```
nnnnnnnnnn nnnnnnnnnn nnnnnnnnnn nnnnnnnnnn nnnnnnnnnn          50

<210> SEQ ID NO 238
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 238
cacugccccc cccccccccc cccccccccc cccccccccc cccccccccc          50

<210> SEQ ID NO 239
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (6)..(50)
<223> OTHER INFORMATION: n represents inosine

<400> SEQUENCE: 239
cagugnnnnn nnnnnnnnnn nnnnnnnnnn nnnnnnnnnn nnnnnnnnnn          50

<210> SEQ ID NO 240
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 240
cacuggcagu cccccccccc cccccccccc cccccccccc cccccccccc          50

<210> SEQ ID NO 241
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (11)..(50)
<223> OTHER INFORMATION: n represents inosine

<400> SEQUENCE: 241
acugccagug nnnnnnnnnn nnnnnnnnnn nnnnnnnnnn nnnnnnnnnn          50

<210> SEQ ID NO 242
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 242
cacuggcagu ugacacaggu uccucacuuc acaaaucguu caucguucac          50

<210> SEQ ID NO 243
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 243
```
gugaacgaug aacgauuugu gaagugagga accuguguca acugccagug               50

<210> SEQ ID NO 244
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 244
caauggcacu uaacccccc cccccccccc cccccccccc cccccccccc               50

<210> SEQ ID NO 245
<211> LENGTH: 50
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(50)
<223> OTHER INFORMATION: n represents inosine

<400> SEQUENCE: 245
ugucaacugc cagugnnnnn nnnnnnnnnn nnnnnnnnnn nnnnnnnnnn               50

<210> SEQ ID NO 246
<211> LENGTH: 13
<212> TYPE: RNA
<213> ORGANISM: Artificial Sequence
<220> FEATURE:
<223> OTHER INFORMATION: Synthetic oligonucleotide

<400> SEQUENCE: 246
cccccccccc ccc                                                       13

<210> SEQ ID NO 247
<211> LENGTH: 35
<212> TYPE: RNA
<213> ORGANISM: Artificial Sequence
<220> FEATURE:
<223> OTHER INFORMATION: Synthetic oligonucleotide

<400> SEQUENCE: 247
cccccccccc cccccccccc cccccccccc ccccc                               35

<210> SEQ ID NO 248
<211> LENGTH: 35
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(35)
<223> OTHER INFORMATION: n represents inosine

<400> SEQUENCE: 248
nnnnnnnnnn nnnnnnnnnn nnnnnnnnnn nnnnn                               35

AGONISTS OF TOLL-LIKE RECEPTOR 3 AND METHODS OF THEIR USE

RELATED APPLICATIONS

This application claims the benefit of U.S. Provisional Application Ser. No. 61/358,543, filed on Jun. 25, 2010; U.S. Provisional Application Ser. No. 61/419,488, filed on Dec. 3, 2010; and U.S. Provisional Application Ser. No. 61/435,434, filed on Jan. 24, 2011, the contents of which are incorporated herein by reference in their entirety.

BACKGROUND OF THE INVENTION

1. Field of the Invention

The present invention relates to modulating the immune system. In particular, the invention relates to oligonucleotide-based compounds that selectively stimulate an immune response through binding to and activating Toll-Like Receptor 3 (TLR3), and their use, alone or in combination with other agents, for treating or preventing diseases wherein modulation of TLR3 activity would be beneficial.

2. Summary of the Related Art

Toll-like receptors (TLRs) are present on many cells of the immune system and have been shown to be involved in the innate immune response (Hornung, V. et al., (2002) J. Immunol. 168:4531-4537). TLRs are a key means by which mammals recognize and mount an immune response to foreign molecules and also provide a means by which the innate and adaptive immune responses are linked (Akira, S. et al. (2001) Nature Immunol. 2:675-680; Medzhitov, R. (2001) Nature Rev. Immunol. 1:135-145). In vertebrates, this family consists of at least 11 proteins called TLR1 to TLR11, which are known to recognize pathogen associated molecular patterns (PAMP) from bacteria, fungi, parasites, and viruses and induce an immune response mediated by a number of transcription factors.

Some TLRs are located on the cell surface to detect and initiate a response to extracellular pathogens and other TLRs are located inside the cell to detect and initiate a response to intracellular pathogens. Table 1 provides a representation of TLRs, the known agonists therefore and the cell types known to contain the TLR (Diebold, S. S. et al. (2004) Science 303:1529-1531; Liew, F. et al. (2005) Nature 5:446-458; Hemmi H et al. (2002) Nat Immunol 3:196-200; Jurk M et al., (2002) Nat Immunol 3:499; Lee J et al. (2003) Proc. Natl. Acad. Sci. USA 100:6646-6651); (Alexopoulou, L. (2001) Nature 413:732-738).

TABLE 1

| TLR Molecule | Agonist | Cell Types Containing Receptor |
|---|---|---|
| Cell Surface TLRs: | | |
| TLR2 | bacterial lipopeptides | Monocytes/macrophages Myeloid dendritic cells Mast cells |
| TLR4 | gram negative bacteria | Monocytes/macrophages Myeloid dendritic cells Mast cells Intestinal epithelium |
| TLR5 | motile bacteria | Monocyte/macrophages Dendritic cells Intestinal epithelium |
| TLR6 | gram positive bacteria | Monocytes/macrophages Mast cells B lymphocytes |

TABLE 1-continued

| TLR Molecule | Agonist | Cell Types Containing Receptor |
|---|---|---|
| Endosomal TLRs: | | |
| TLR3 | double stranded RNA viruses | Dendritic cells B lymphocytes |
| TLR7 | single stranded RNA viruses; RNA-immunoglobulin complexes | Monocytes/macrophages Plasmacytoid dendritic cells B lymphocytes |
| TLR8 | single stranded RNA viruses; RNA-immunoglobulin complexes | Monocytes/macrophages Dendritic cells Mast cells |
| TLR9 | DNA containing unmethylated "CpG" motifs; DNA-immunoglobulin complexes | Monocytes/macrophages Plasmacytoid dendritic cells B lymphocytes |

The signal transduction pathway mediated by the interaction between a ligand and a TLR is shared among most members of the TLR family and involves a toll/IL-1 receptor (TIR domain), the myeloid differentiation marker 88 (MyD88), IL-1R-associated kinase (IRAK), interferon regulating factor (IRF), TNF-receptor-associated factor (TRAF), TGFβ-activated kinase1, IκB kinases, IκB, and NF-κB (see for example: Akira, S. (2003) J. Biol. Chem. 278:38105 and Geller at al. (2008) Curr. Drug Dev. Tech. 5:29-38). More specifically, for TLRs 1, 2, 4, 5, 6, 7, 8, 9 and 11, this signaling cascade begins with a PAMP ligand interacting with and activating the membrane-bound TLR, which exists as a homo-dimer in the endosomal membrane or the cell surface. Following activation, the receptor undergoes a conformational change to allow recruitment of the TIR domain containing protein MyD88, which is an adapter protein that is common to all TLR signaling pathways except TLR3. MyD88 recruits IRAK4, which phosphorylates and activates IRAK1. The activated IRAK1 binds with TRAF6, which catalyzes the addition of polyubiquitin onto TRAF6. The addition of ubiquitin activates the TAK/TAB complex, which in turn phosphorylates IRFs, resulting in NF-kB release and transport to the nucleus. NF-kB in the nucleus induces the expression of proinflammatory genes (see for example, Trinchieri and Sher (2007) Nat. Rev. Immunol. 7:179-190).

TLR3 signaling occurs through a MyD88 independent pathway that begins with the TLR3 ligand interacting with and activating TLR3, which exists as a homo-dimer. Following activation, TLR3 undergoes a conformational change, allowing recruitment of a TIR-domain-containing adapter-inducing interferon-β (TRIF), which activates TANK-binding Kinase 1 (TBK1). TBK1 phosphorylates and activates IRF-3, resulting in the activation of interferons α and β and ultimately the generation of an inflammatory immune response (see for example: Miggin and O'Neill (2006) J. Leukoc. Biol. 80:220-226).

As a result of their involvement in regulating an inflammatory response, TLRs have been shown to play a role in the pathogenesis of many diseases, including autoimmunity, infectious disease and inflammation (Papadimitraki et al. (2007) J. Autoimmun. 29: 310-318; Sun et al. (2007) Inflam. Allergy Drug Targets 6:223-235; Diebold (2008) Adv. Drug Deliv. Rev. 60:813-823; Cook, D. N. et al. (2004) Nature Immunol. 5:975-979; Tse and Horner (2008) Semin. Immunopathol. 30:53-62; Tobias & Curtiss (2008) Semin. Immunopathol. 30:23-27; Ropert et al. (2008) Semin. Immunopathol. 30:41-51; Lee et al. (2008) Semin. Immunopathol.

30:3-9; Gao et al. (2008) Semin. Immunopathol. 30:29-40; Vijay-Kumar et al. (2008) Semin. Immunopathol. 30:11-21).

The selective localization of TLRs and the signaling generated therefrom, provides some insight into their role in the immune response. The immune response involves both an innate and an adaptive response based upon the subset of cells involved in the response. For example, the T helper (Th) cells involved in classical cell-mediated functions such as delayed-type hypersensitivity and activation of cytotoxic T lymphocytes (CTLs) are Th1 cells. This response is the body's innate response to antigen (e.g. viral infections, intracellular pathogens, and tumor cells), and results in a secretion of IFN-gamma and a concomitant activation of CTLs.

TLR3 is known to localize in endosomes inside the cell and recognizes nucleic acids (DNA and RNA) and small molecules such as nucleosides and nucleic acid metabolites. TLR3 has been shown to recognize and respond to double stranded RNA (dsRNA) viruses (Diebold, S. S., et al., (2004) Science 303:1529-1531). In addition, it has been shown that small interfering RNA (siRNA) molecules and non-targeted dsRNA molecules can non-specifically activate TLR3 (Alexopoulou et al. (2008) Nature 413:732-738). However, this non-specific activation of TLR3 was determined to be dependent on a MyD88 pathway, indicating that such dsRNA molecules have the potential to generate immune responses that are not specific to TLR3.

In addition to naturally existing and synthetic dsRNA ligands for TLR3, other synthetic oligonucleotide analogs have been shown to activate TLR3. The poly-inosinic acid poly-cytidylic acid complex (poly(I:C)), a synthetic double stranded RNA molecule that is designed to mimic viral dsRNA, is composed of a long strand of poly(I) annealed to a long strand of poly(C). Due to the need for long strands, poly(I:C) compounds are routinely synthesized using enzymatic processes. As a result of the enzymatic synthesis, the size of poly(I:C) compounds and preparations is known to vary between 0.2 kb and 8 kb. Poly(I:C) has been shown to induce interferon (Field et al. (1968) Proc. Natl. Acad. Sci. U.S.A. 61:340). Subsequent to this discovery, it was determined that poly(I:C) induces interferon through activation of TLR3 and, as compared to dsRNA molecules, poly(I:C) is preferentially recognized by TLR3 (Alexopoulou et al. (2001) Nature 413:732-738; Okahira et al. (2005) DNA Cell Biol. 24:614-623). The interferon inducing properties of poly (I:C) as well as its preferential binding to TLR3 make poly (I:C) a desirable molecule for use at inducing interferon in vivo. However, poly(I:C) exists as long strands of nucleic acids that have been shown to form undesirable helix-with-loop structures (Ichikawa et al. (1967) Bul. Chem. Soc. Japan 40:2272-2277) and to have toxic properties when administered in vivo (Absher and Stinebring (1969) Nature 223:1023; Lindsay et al. (1969) Nature 223:717; Adamson and Fabro (1969) Nature 223:718; Leonard et al. (1969) Nature 224: 1023). Thus, the medical, therapeutic, and prophylactic use of poly(I:C) is limited.

Attempts have been made to modify the structure of poly (I:C) to retain its immune stimulatory properties while reducing its toxicity (WO2008109083). These compounds insert mismatches into the poly(I:C) strand by replacing cytosine with uracil at defined positions throughout the double stranded molecule. The compounds are referred to as poly(I: $C_{12}U$). However, these compounds have had limited therapeutic success because their in vivo efficacy has been questioned and they have been rejected by the U.S.A. Food and Drug Administration.

Thus, it would be desirable to have a selective TLR3 agonist that retains the immune stimulatory activity and therapeutic activity of a poly(I:C) oligonucleotide without the undesired enzymatic synthesis, helix-with-loop structures, toxicity, and lack of efficacy of the currently available poly (I:C), poly(I:$C_{12}U$), and dsRNA compounds.

BRIEF SUMMARY OF THE INVENTION

The present invention relates to TLR3 agonist compounds, compositions comprising such compounds, and their use for stimulating a TLR3-mediated immune response.

In a first aspect, the invention provides novel, synthetic TLR3 agonists compromising a first oligoribonucleotide having a first complementary domain and a poly-inosinic acid domain and a second oligoribonucleotide having a second complementary domain and a poly-cytidylic acid domain, wherein the complementary domain of the first oligoribonucleotide is complementary to the complementary domain of the second oligoribonucleotide and wherein the hybridization of the first and second oligonucleotides to each other is in such a manner that either the complementary domains or the poly-inosinic acid and poly-cytidylic acid domains are free, such that further first oligoribonucleotides and further second oligoribonucleotides can hybridize to the free poly-inosinic acid or free poly-cytidylic acid or free complementary domains.

In a second aspect, the invention provides a composition comprising a TLR3 agonist according to the invention and a physiologically acceptable carrier.

In a third aspect, the invention provides a method of stimulating TLR3 activity. In this method, a TLR3 agonist according to the invention is specifically contacted with or bound by TLR3 in vitro, in vivo, ex vivo or in a cell.

In a fourth aspect, the invention provides methods for stimulating the activity of TLR3 in a mammal, particularly a human, such methods comprising administering to the mammal a TLR3 agonist according to the invention.

In a fifth aspect, the invention provides a method for stimulating a TLR3-mediated immune response in a mammal, the method comprising administering to the mammal a TLR3 agonist according to the invention in a pharmaceutically effective amount.

In a sixth aspect, the invention provides a method for therapeutically treating a mammal having a disease treatable by TLR3 activation or TLR3-mediated immune stimulation, such method comprising administering to the mammal, particularly a human, a TLR3 agonist according to the invention, or a composition thereof, in a pharmaceutically effective amount. The invention also relates to the TLR3 agonist and compositions thereof, which are disclosed herein in methods of treating diseases and illnesses, for use in treating diseases and illnesses and for use as vaccine adjuvants.

In a seventh aspect, the invention provides methods for preventing a disease or disorder or for use as vaccine adjuvants in a mammal, particularly a human, at risk of contracting or developing a disease or disorder preventable by TLR3 activation or TLR3-mediated stimulation of an immune response. The method according to this aspect of the invention comprises administering to the mammal a TLR3 agonist according to the invention, or a composition thereof, in a prophylactically effective amount.

In an eighth aspect, the TLR3 agonists and compositions thereof according to the invention are also useful for examining the function of the TLR3 in a cell or in a control mammal or in a mammal afflicted with a disease associated with TLR3 or immune stimulation or immune suppression. The cell or mammal is administered the TLR3 agonist according to the first or second aspects of the invention, and the activity of TLR3 is examined.

Figure 1A:
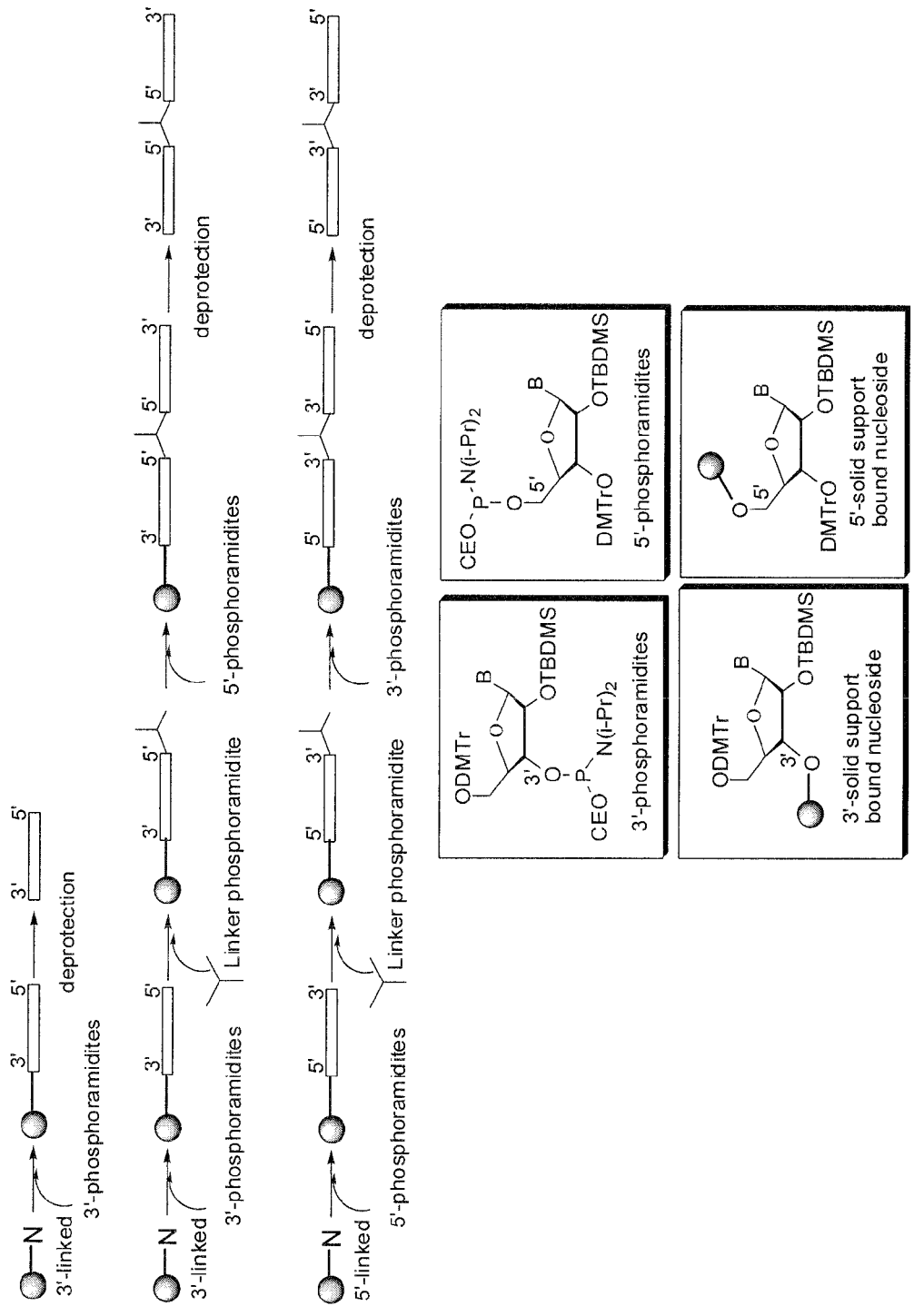
FIG. 1A is a synthetic scheme for the linear synthesis of TLR3 agonist of the invention. DMTr=4,4'-dimethoxytrityl; CE=cyanoethyl.
Figure 1B:
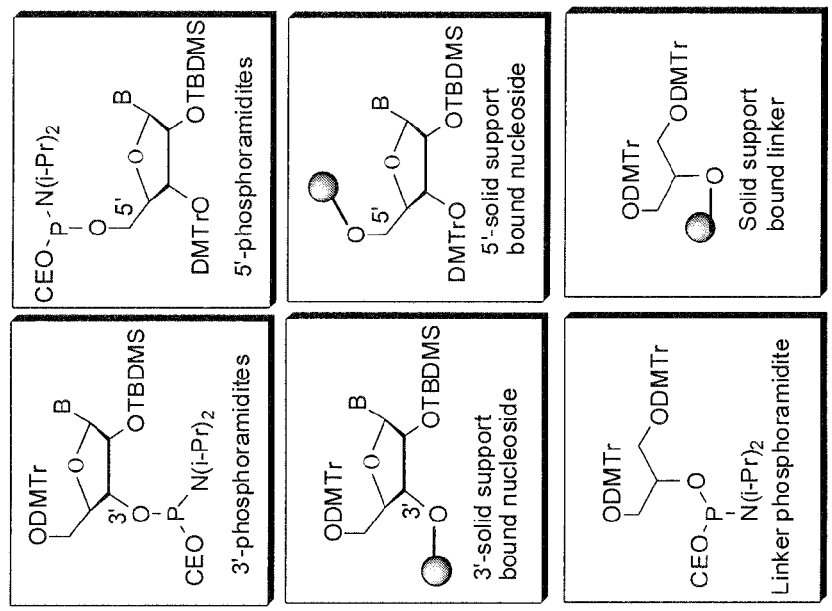
FIG. 1B is a synthetic scheme for the parallel synthesis of TLR3 agonists of the invention. DMTr=4,4'-dimethoxytrityl; CE=cyanoethyl.
Figure 1B:
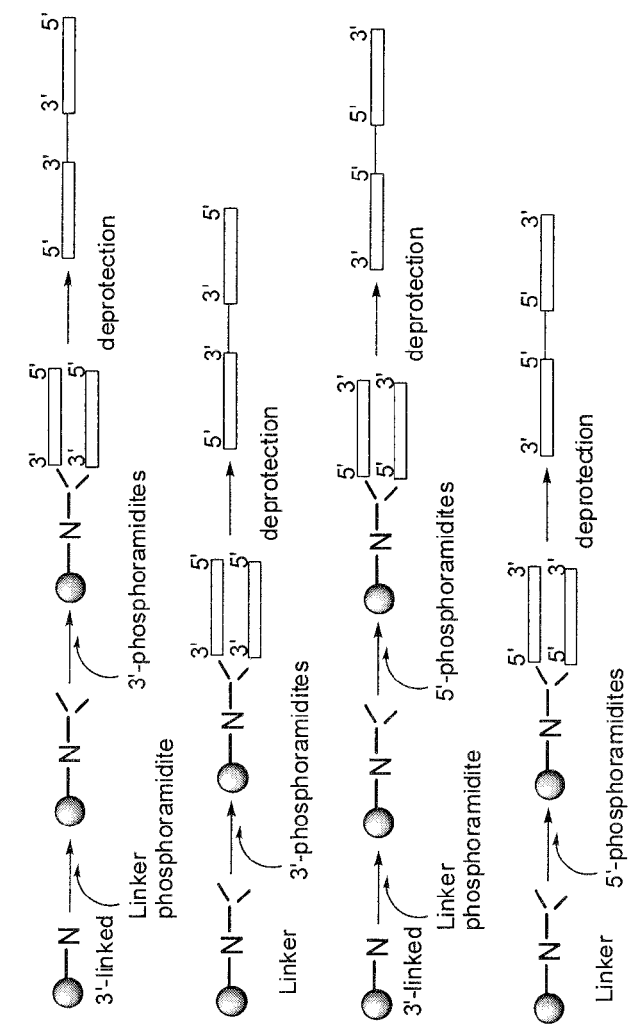
Figure 2A:
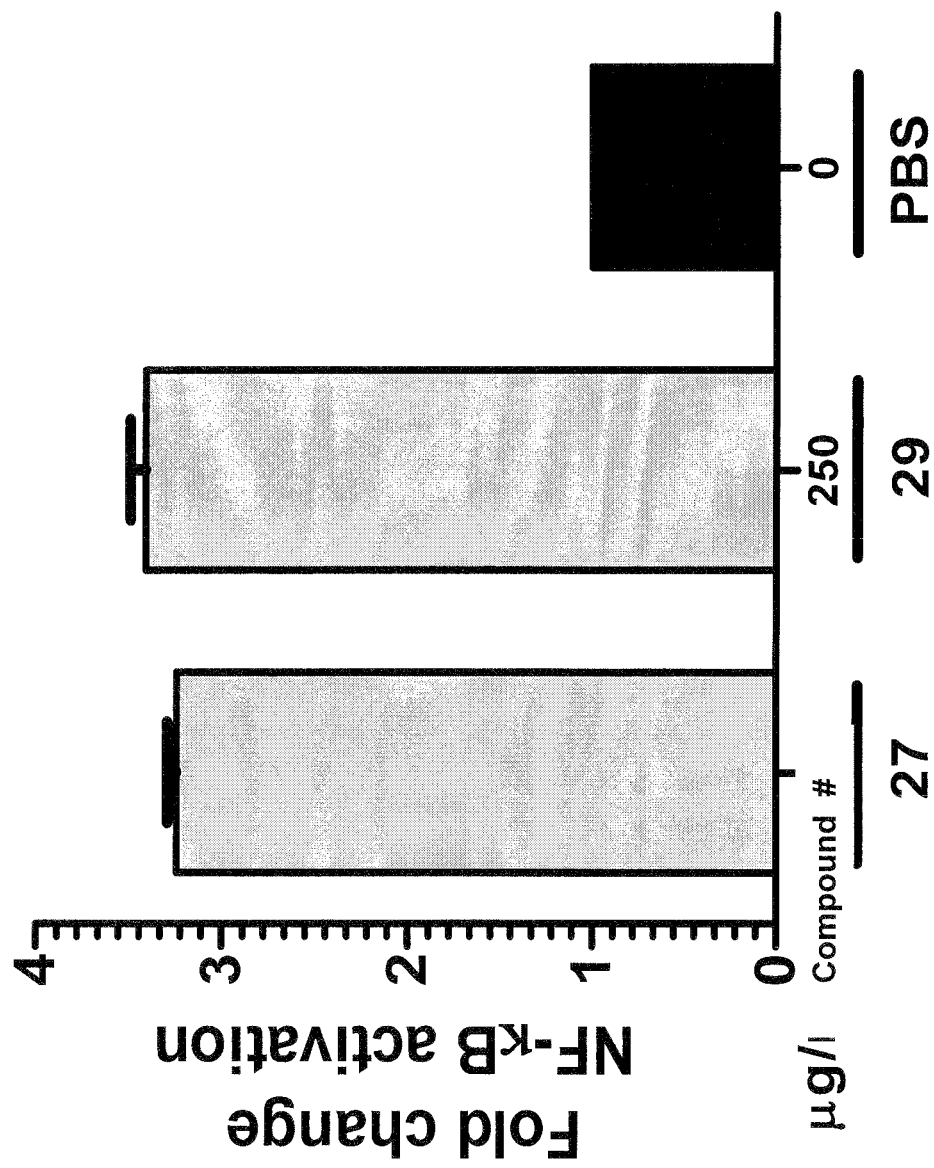
FIGS. 2A and 2B and Table 6 depict the immune stimulatory activity of exemplary TLR3 agonists according to the invention in HEK293 cells expressing human TLR3. Briefly, the HEK293 cells were treated with TLR3 agonists of the invention for 18 hr, and the levels of NF-κB subsequently produced were determined using SEAP (secreted form of human embryonic alkaline phosphatase) assay. The data demonstrate the ability of exemplary TLR3 agonists according to the invention to stimulate TLR3 activity in a dose dependent fashion in HEK293 cells that were cultured and treated according to Example 2. More generally these data demonstrate that TLR3 agonists of the invention can activate TLR3 and generate an immune response.
Figure 2B:
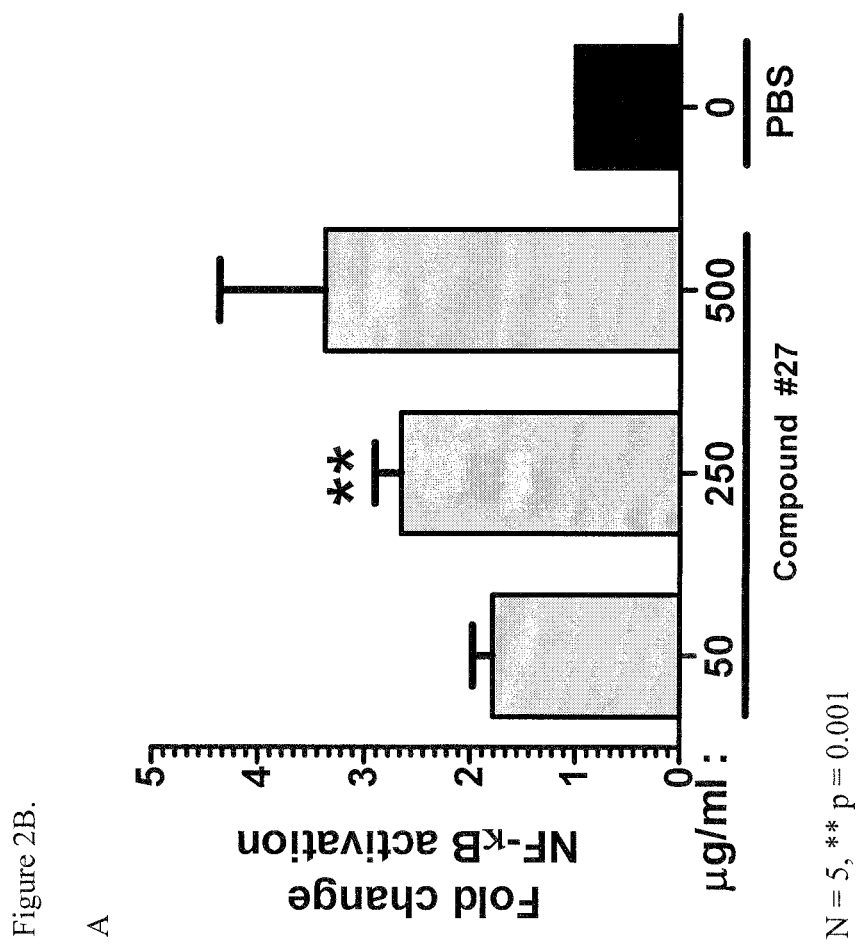
Figure 3:
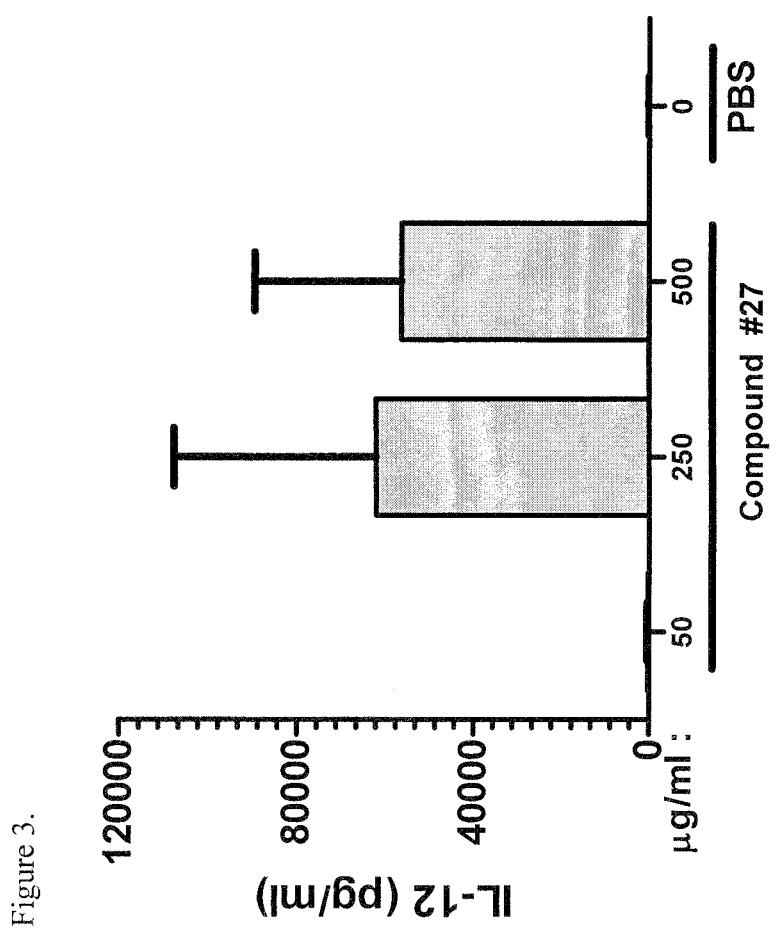
FIG. 3 and Tables 7, 8, 9, 10, and 11 depict the immune stimulatory activity of an exemplary TLR3 agonist according to the invention in J774 macrophage cells, which naturally contain TLR3. Briefly, the J774 cells were treated with a TLR3 agonist of the invention for 18 hr, and the levels of IL-12 subsequently produced were determined using ELISA. The data demonstrate the ability of exemplary TLR3 agonists according to the invention to stimulate TLR3 activity in a dose dependent fashion in J774 cells that were cultured and treated according to Example 2. More generally these data demonstrate that TLR3 agonists of the invention can activate TLR3 and generate an immune response in immune cells.
Figure 4:
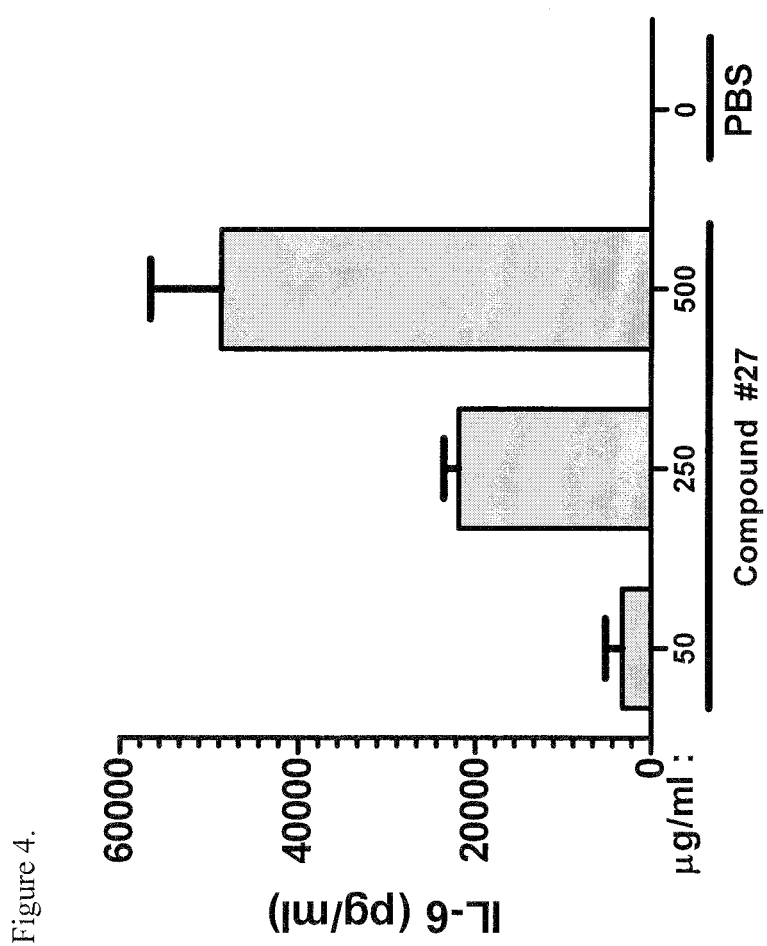
FIG. 4 is a graphical representation of the immune stimulatory activity of an exemplary TLR3 agonist according to the invention in J774 macrophage cells, which naturally contain TLR3. Briefly, the J774 cells were treated with a TLR3 agonist of the invention for 18 hr, and the levels of IL-6 subsequently produced were determined using ELISA. The data demonstrate the ability of exemplary TLR3 agonists according to the invention to stimulate TLR3 activity in a dose dependent fashion in J774 cells that were cultured and treated according to Example 2. More generally these data demonstrate that TLR3 agonists of the invention can activate TLR3 and generate an immune response in immune cells.
Figure 5:
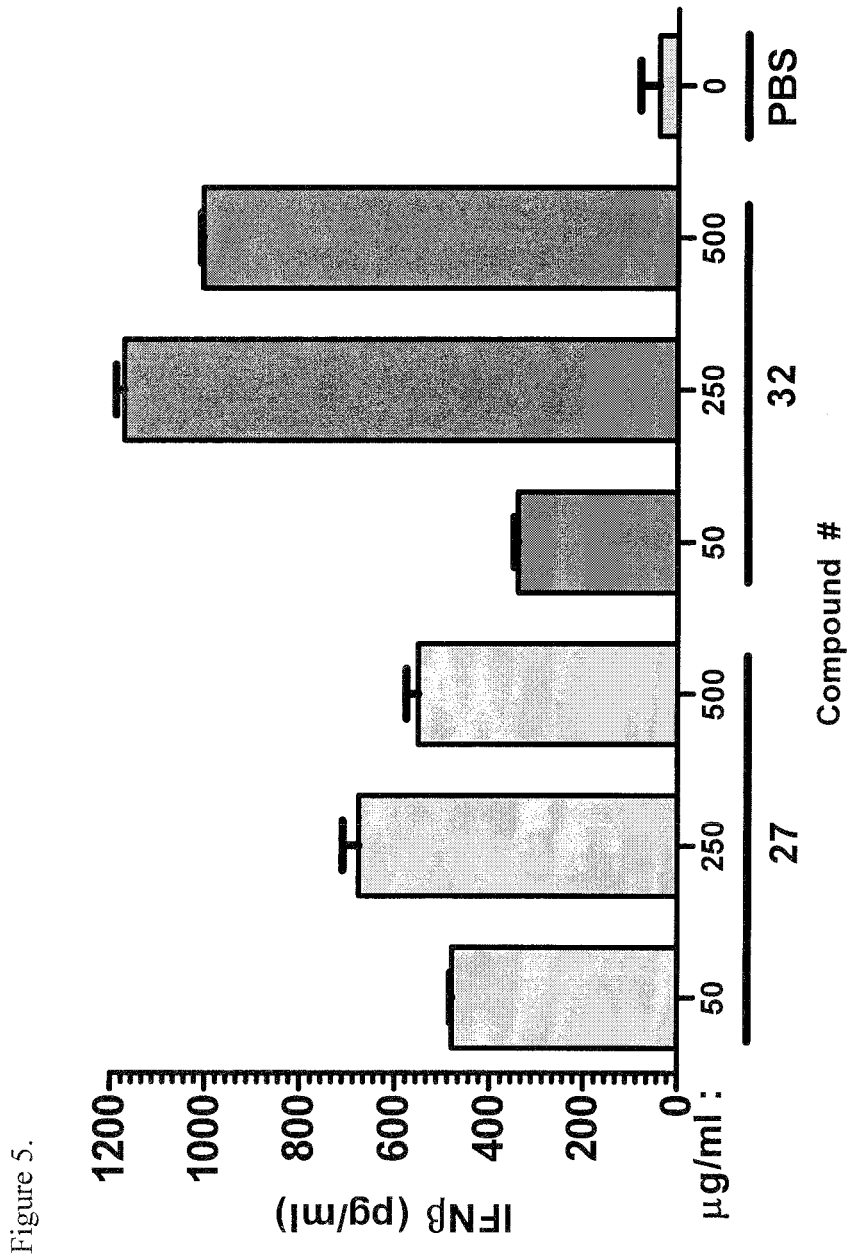
FIG. 5 is a graphical representation of the immune stimulatory activity of exemplary TLR3 agonists according to the invention in J774 macrophage cells, which naturally contain TLR3. Briefly, the J774 cells were treated with selected TLR3 agonists of the invention for 18 hr, and the levels of IFNβ subsequently produced were determined using ELISA. The data demonstrate the ability of exemplary TLR3 agonists according to the invention to stimulate TLR3 activity in a dose dependent fashion in J774 cells that were cultured and treated according to Example 2. More generally these data demonstrate that TLR3 agonists of the invention can activate TLR3 and generate an immune response in immune cells.
Figure 6:
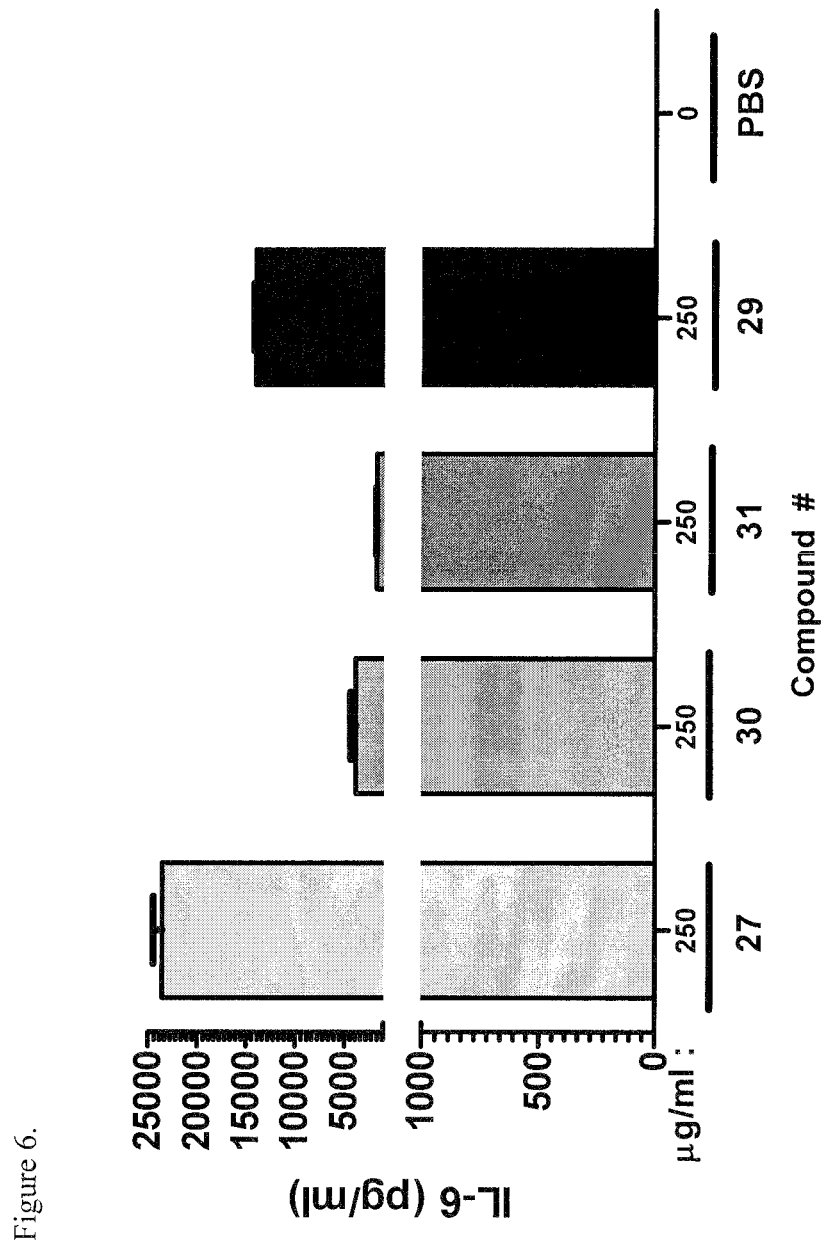
FIG. 6 is a graphical representation of the immune stimulatory activity of exemplary TLR3 agonist according to the invention in J774 macrophage cells, which naturally contain TLR3. Briefly, the J774 cells were treated with TLR3 agonists of the invention for 18 hr, and the levels of IL-6 subsequently produced were determined using ELISA. The data demonstrate the ability of exemplary TLR3 agonists according to the invention to stimulate TLR3 activity in a dose dependent fashion in J774 cells that were cultured and treated according to Example 2. More generally these data demonstrate that TLR3 agonists of the invention can activate TLR3 and generate an immune response in immune cells.
Figure 7:
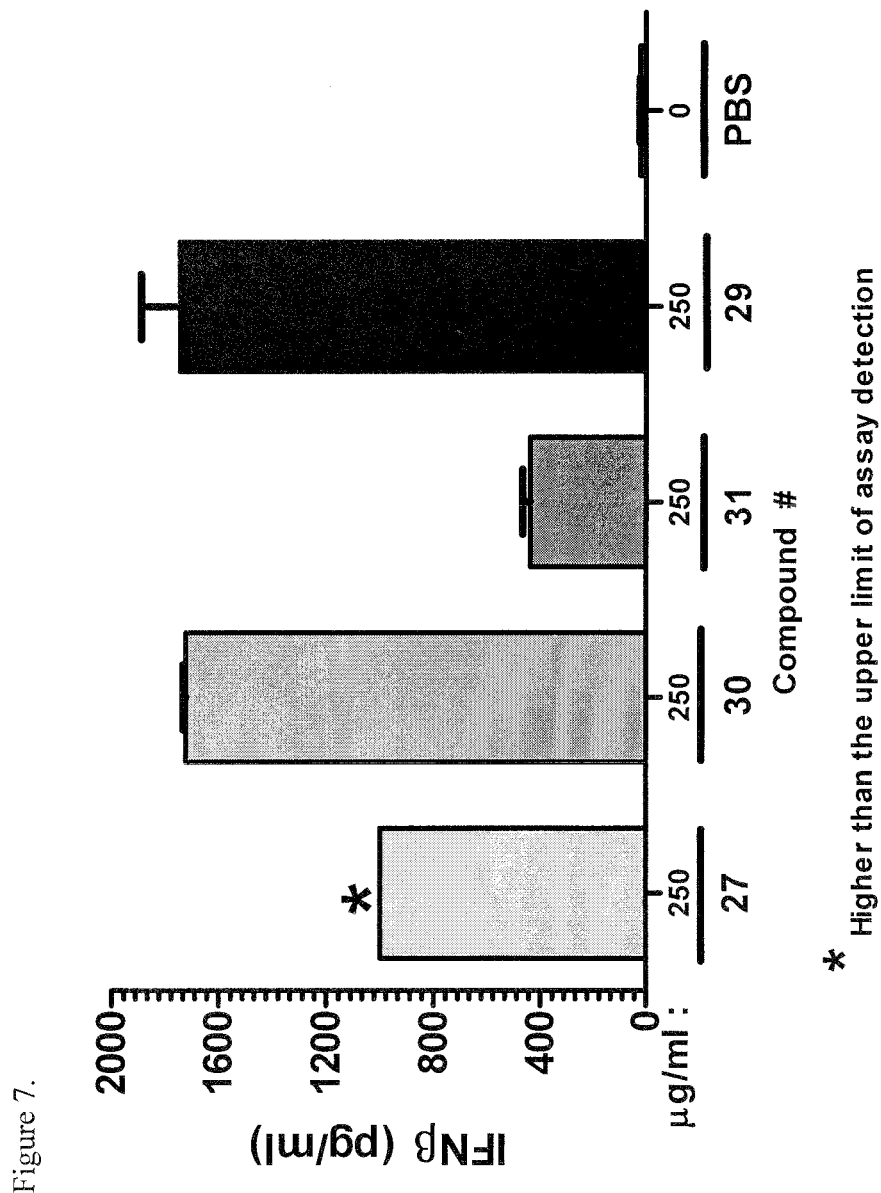
FIG. 7 is a graphical representation of the immune stimulatory activity of exemplary TLR3 agonist according to the invention in J774 macrophage cells, which naturally contain TLR3. Briefly, the J774 cells were treated with TLR3 agonists of the invention for 18 hr, and the levels of IFNβ subsequently produced were determined using ELISA. The data demonstrate the ability of exemplary TLR3 agonists according to the invention to stimulate TLR3 activity in a dose dependent fashion in J774 cells that were cultured and treated according to Example 2. More generally these data demonstrate that TLR3 agonists of the invention can activate TLR3 and generate an immune response in immune cells.

Table 3 and Table 12 depict cytokine and chemokine concentrations from human PBMCs that were treated and analyzed according to example 2. Briefly, the PBMCs were isolated from freshly obtained healthy human volunteer's blood and cultured with 250 μg/ml of exemplary TLR3 agonists of the invention for 24 hr, and supernatants were collected and analyzed by Luminex multiplex assay cytokine and chemokine levels. The data demonstrate that administration of a TLR3 agonist of the invention generates a distinct, TLR3-mediated cytokine and chemokine profile in human immune cells.

Table 4 depicts cytokine and chemokine concentrations from human plasmacytoid dendritic cells (pDCs) that were isolated, treated, and analyzed according to example 2. Briefly, the pDCs were isolated from freshly obtained healthy human volunteer's blood PBMCs and cultured with 250 μg/ml dose of TLR3 agonists of the invention for 24 hr, and supernatants were collected and analyzed by Luminex multiplex assay for cytokine and chemokine levels. The data demonstrate that administration of a TLR3 agonist of the invention generates a distinct, TLR3-mediated cytokine and chemokine profile in human immune cells.

Tables 5A, 5B, 5C, and 5D depict the immune stimulatory activity of TLR3 agonists that do not have the preferred structure of the TLR3 agonists of the invention and that were isolated, treated, and analyzed according to example 2. Briefly, the HEK293 cells were treated with TLR3 agonists lacking the preferred structure of the TLR3 agonists of the invention for 18 hr, and the levels of NF-κB subsequently produced were determined using SEAP (secreted form of human embryonic alkaline phosphatase) assay. The data demonstrate the compounds lacking the preferred structure of the TLR3 agonists of the invention do not induce a tTLR3-mediated immune response.

Table 13 depicts cytokine and chemokine concentrations from human myeloid dendritic cells (mDCs) that were isolated, treated, and analyzed according to Example 2. Briefly, the pDCs were isolated from freshly obtained healthy human volunteer's blood PBMCs and cultured with 300 μg/ml dose of TLR3 agonists of the invention for 18 hr, and supernatants were collected and analyzed by Luminex multiplex assay for cytokine and chemokine levels. The data demonstrate that administration of a TLR3 agonist of the invention generates a distinct, TLR3-mediated cytokine and chemokine profile in human immune cells.

Table 15 depicts serum cytokine induction in C57BL/6 mice (n=3) 2 hours after they were treated and analyzed according to Example 4. Briefly, the C57BL/6 mice were injected subcutaneously with 0 mg/kg or 10 mg/kg dose of TLR3 agonists, and 2 hours after administration of the agonist, serum was analyzed for immune stimulatory cytokine levels, and IL-12 levels are presented. The data demonstrate that in vivo administration of a TLR3 agonist of the invention generates a distinct TLR-mediated in vivo cytokine profile.

DETAILED DESCRIPTION OF THE PREFERRED EMBODIMENTS

The invention relates to TLR3 agonist compounds, compositions comprising such compounds, and their use for stimulating a TLR3-mediated immune response. The TLR3 agonists according to the invention are stable, specific, and capable of activating an innate immune response, thereby overcoming the problems of certain previously attempted approaches to create TLR3 agonists. Pharmaceutical and other compositions comprising the compounds according to the invention are also provided. Further provided are methods of stimulating a TLR3-mediated immune response in cells or tissues comprising contacting said cells or tissues with one or more of the TLR3 agonist compounds or compositions thereof alone or in combination with other prophylactic or therapeutic compounds or compositions.

The invention provides TLR3 agonist compounds that are designed to specifically and potently stimulate TLR3. These TLR3 agonists have unique structures that are preferentially hound by TLR3, resulting in optimal stimulation of a TLR3-mediated immune response.

The TLR3 agonists according to the invention stimulate an immune response in various in vitro and in vivo experimental models. As such, the TLR3 agonists or compositions thereof according to the invention are useful as tools to study the immune system, as well as to compare the immune systems of various animal species, such as humans and mice.

Further provided are methods of treating an animal, particularly a human, having, suspected of having, or being prone to develop a disease or condition that would benefit from TLR3-mediated immune stimulation by administering a therapeutically or prophylactically effective amount of one or more of the TLR3 agonist compounds or compositions of the invention. These can be used for immunotherapy applications such as, but not limited to, treatment of cancer, asthma, allergy, airway inflammation, inflammatory disorders, autoimmune disorders, skin disorders, diseases caused by a pathogen, and infectious diseases and as vaccine adjuvants in adult and pediatric human and veterinary applications.

In addition, TLR3 agonist oligonucleotides of the invention are useful in the prevention and/or treatment of various diseases, either alone, in combination with or co-administered with other drugs or prophylactic or therapeutic compositions, for example, DNA vaccines, antigens, antibodies, and allergens, TLR antagonist, such as TLR7 and or TLR8 antagonist, and/or other TLR agonists; and in combination with chemotherapeutic agents such as both traditional chemotherapy and modern targeted therapies for prevention and treatment of diseases.

The patents and publications cited herein reflect the level of knowledge in the art and are hereby incorporated by reference in their entirety. Any conflict between the teachings of these patents and publications and this specification shall be resolved in favor of the latter.

The foregoing and other objects of the present invention, the various features thereof, as well as the invention itself may be more fully understood from the following description, when read together with the accompanying drawings in which:

The term "2'-O-substituted" means substitution of the 2' position of the pentose moiety with an —O— lower alkyl group containing 1-6 saturated or unsaturated carbon atoms (for example, but not limited to, 2'-O-methyl), or with an —O-aryl or allyl group having 2-6 carbon atoms, wherein such alkyl, aryl or allyl group may be unsubstituted or may be substituted, (for example, with 2'-O-ethoxy-methyl, halo, hydroxy, trifluoromethyl, cyano, nitro, acyl, acyloxy, alkoxy, carboxyl, carbalkoxyl, or amino groups); or with a hydroxy, an amino or a halo group, but not with a 2'-H group. In some embodiments the oligonucleotides of the invention include four or five ribonucleotides 2'-O-alkylated at their 5' terminus (i.e., 5' 2-O-alkylated ribonucleotides), and/or four or five ribonucleotides 2'-O-alkylated at their 3' terminus (i.e., 3' 2—O-alkylated ribonucleotides). In exemplar embodiments, the nucleotides of the synthetic oligonucleotides are linked by at least one phosphorothioate internucleotide linkage. The phosphorothioate linkages may be mixed Rp and Sp enantiomers, or they may be stereoregular or substantially stereoregular in either Rp or Sp form (see Iyer et al. (1995) Tetrahedron Asymmetry 6:1051-1054).

The term "3'", when used directionally, generally refers to a region or position in a polynucleotide or oligonucleotide 3' (toward the 3' end of the nucleotide) from another region or position in the same polynucleotide or oligonucleotide.

The term "5'", when used directionally, generally refers to a region or position in a polynucleotide or oligonucleotide 5' (toward the 5' end of the nucleotide) from another region or position in the same polynucleotide or oligonucleotide.

The term "about" generally means that the exact number is not critical. Thus, oligonucleotides having one or two fewer nucleoside residues, or from one to several additional nucleoside residues are contemplated as equivalents of each of the embodiments described above.

The term "agonist" generally refers to a substance that binds to a receptor of a cell and induces a response. An agonist often mimics the action of a naturally occurring substance such as a ligand.

The term "airway inflammation" generally includes, without limitation, inflammation in the respiratory tract caused by allergens, including asthma.

The term "allergen" generally refers to an antigen or antigenic portion of a molecule, usually a protein, which elicits an allergic response upon exposure to a subject. Typically the subject is allergic to the allergen as indicated, for instance, by the wheal and flare test or any method known in the art. A molecule is said to be an allergen even if only a small subset of subjects exhibit an allergic IgE) immune response upon exposure to the molecule.

The term "allergy" generally includes, without limitation, food allergies, respiratory allergies and skin allergies.

The term "antigen" generally refers to a substance that is recognized and selectively bound by an antibody or by a T cell antigen receptor. Antigens may include but are not limited to peptides, proteins, nucleosides, nucleotides and combinations thereof. Antigens may be natural or synthetic and generally induce an immune response that is specific for that antigen.

The term "antagonist" generally refers to a substance that attenuates the effects of an agonist.

The term "cancer" generally refers to, without limitation, any malignant growth or tumor caused by abnormal or uncontrolled cell proliferation and/or division. Cancers may occur in humans and/or mammals and may arise in any and all tissues. Treating a patient having cancer may include administration of a compound, pharmaceutical formulation or vaccine according to the invention such that the abnormal or uncontrolled cell proliferation and/or division, or metastasis is affected.

The term "carrier" generally encompasses any excipient, diluent, filler, salt, buffer, stabilizer, solubilizer, oil, lipid, lipid containing vesicle, microspheres, liposomal encapsulation, or other material well known in the art for use in pharmaceutical formulations. It will be understood that the characteristics of the carrier, excipient, or diluent will depend on the route of administration for a particular application. The preparation of pharmaceutically acceptable formulations containing these materials is described in, for example, *Remington's Pharmaceutical Sciences*, 18th Edition, ed. A. Gennaro, Mack Publishing Co., Easton, Pa., 1990.

The term "co-administration" or "co-administered" generally refers to the administration of at least two different substances sufficiently close in time to modulate an immune response. Co-administration refers to simultaneous administration, as well as temporally spaced order of up to several days apart, of at least two different substances in any order, either in a single dose or separate doses.

The term "in combination with" generally means administering a TLR3 agonist or composition thereof according to the invention and another agent useful for treating the disease or condition that does not abolish the activity of the TLR3 agonist or composition thereof in the course of treating a patient. Such administration may be done in any order, including simultaneous administration, as well as temporally spaced order from a few seconds up to several days apart. Such combination treatment may also include more than a single administration of the TLR3 agonist or composition thereof according to the invention and/or independently the other agent. The administration of the TLR3 agonist or composition thereof according to the invention and the other agent may be by the same or different routes.

The term "individual" or "subject" or "vertebrate" generally refers to a mammal, such as a human.

The term "linear synthesis" generally refers to a synthesis that starts at one end of an oligonucleotide and progresses linearly to the other end. Linear synthesis permits incorporation of either identical or non-identical (in terms of length, base composition and/or chemical modifications incorporated) monomeric units into an oligonucleotide.

The term "mammal" is expressly intended to include warm blooded, vertebrate animals, including, without limitation, humans, non-human primates, rats, mice, cats, dogs, horses, cattle, cows, pigs, sheep and rabbits.

The term "nucleoside" generally refers to compounds consisting of a sugar, usually ribose or deoxyribose, and a purine or pyrimidine base.

The term "nucleotide" generally refers to a nucleoside comprising a phosphorous-containing group attached to the sugar.

The term "modified nucleoside" generally is a nucleoside that includes a modified heterocyclic base, a modified sugar moiety, or any combination thereof. In some embodiments, the modified nucleoside is a non-natural pyrimidine or purine nucleoside, as herein described. For purposes of the invention, a modified nucleoside, a pyrimidine or purine analog or non-naturally occurring pyrimidine or purine can be used interchangeably and refers to a nucleoside that includes a non-naturally occurring base and/or non-naturally occurring sugar moiety. For purposes of the invention, a base is considered to be non-natural if it is not guanine, cytosine, adenine, thymine or uracil and a sugar is considered to be non-natural if it is not β-ribo-furanoside or 2'-deoxyribo-furanoside. For purposes of the invention, a "modified nucleotide" is a modified nucleoside comprising a phosphorous-containing group attached to the sugar.

The term "modified oligonucleotide" as used herein describes an oligonucleotide in which at least two of its nucleotides are covalently linked via a synthetic linkage, i.e., a linkage other than a phosphodiester linkage between the 5' end of one nucleotide and the 3' end of another nucleotide or the 5' end of a nucleotide and the 2' end of another nucleotide in which the 5' nucleotide phosphate has been replaced with any number of chemical groups. The term "modified oligonucleotide" also encompasses oligonucleotides having at least one modified nucleotide.

The term "nucleic acid" encompasses a genomic region or an RNA molecule transcribed therefrom. In some embodiments, the nucleic acid is mRNA.

The term "nucleotidic linkage" generally refers to a chemical linkage to join two nucleosides through their sugars (e.g. 3'-3',2'-3',2'-5',3'-5') consisting of a phosphorous atom and a charged, or neutral group (e.g., phosphodiester, phosphorothioate, phosphorodithioate or methylphosphonate) between adjacent nucleosides.

For purposes of the invention, a "non-nucleotidic linker" is any moiety that can be linked to the oligonucleotides by way of covalent or non-covalent linkages. Preferably such linker is from about 2 angstroms to about 200 angstroms in length. Several examples of preferred linkers are set forth below. Non-covalent linkages include, but are not limited to, electrostatic interaction, hydrophobic interactions, π-stacking interactions, and hydrogen bonding. The term "non-nucleotidic linker" is not meant to refer to an internucleoside linkage, as described above, e.g., a phosphodiester, phosphorothioate, or phosphorodithioate functional group, that directly connects the 3'-hydroxyl groups of two nucleosides.

The term "oligonucleotide" refers to a polynucleoside formed from a plurality of linked nucleoside units. The nucleoside units may be part of viruses, bacteria, cell debris or oligonucleotide-based compositions (for example, siRNA and microRNA). Such oligonucleotides can also be obtained from existing nucleic acid sources, including genomic or cDNA, but are preferably produced by synthetic methods. In certain embodiments each nucleoside unit includes a heterocyclic base and a pentofuranosyl, trehalose, arabinose, 2'-deoxy-2'-substituted nucleoside, 2'-deoxy-2'-O-substituted arabinose, 2'-O-substituted arabinose or hexose sugar group. The nucleoside residues can be coupled to each other by any of the numerous known internucleoside linkages. Such internucleoside linkages include, without limitation, phosphodiester, phosphorothioate, phosphorodithioate, methylphosphonate, alkylphosphonate, alkylphosphonothioate, phosphotriester, phosphoramidate, siloxane, carbonate, carboalkoxy, acetamidate, carbamate, morpholino, borano, thioether, bridged phosphoramidate, bridged methylene phosphonate, bridged phosphorothioate, and sulfone internucleoside linkages. The term "oligonucleotide-based compound" also encompasses polynucleosides having one or more stereospecific internucleoside linkage (e.g., $(R_P)$- or $(S_P)$-phosphorothioate, alkylphosphonate, or phosphotriester linkages). As used herein, the terms "oligonucleotide" and "dinucleotide" are expressly intended to include polynucleosides and dinucleosides having any such internucleoside linkage, whether or not the linkage comprises a phosphate group. In certain exemplar embodiments, these internucleoside linkages may be phosphodiester, phosphorothioate or phosphorodithioate linkages, or combinations thereof.

The term "peptide" generally refers to polypeptides that are of sufficient length and composition to affect a biological response, for example, antibody production or cytokine activity whether or not the peptide is a hapten. The term "peptide" may include modified amino acids (whether or not naturally or non-naturally occurring), where such modifications include, but are not limited to, phosphorylation, glycosylation, pegylation, lipidization and methylation.

The term "pharmaceutically acceptable" means a nontoxic material that does not interfere with the effectiveness of a compound according to the invention or the biological activity of a compound according to the invention.

The term "physiologically acceptable" refers to a nontoxic material that is compatible with a biological system such as a cell, cell culture, tissue, or organism. Preferably, the biological system is a living organism, such as a mammal, particularly a human.

The term "prophylactically effective amount" generally refers to an amount sufficient to prevent or reduce the development of an undesired biological effect.

The term "therapeutically effective amount" or "pharmaceutically effective amount" generally refers to an amount sufficient to affect a desired biological effect, such as a beneficial result, including, without limitation, prevention, diminution, amelioration or elimination of signs or symptoms of a disease or disorder. Thus, the total amount of each active component of the pharmaceutical composition or method is sufficient to show a meaningful patient benefit. Thus, a "pharmaceutically effective amount" will depend upon the context in which it is being administered. A pharmaceutically effective amount may be administered in one or more prophylactic or therapeutic administrations. When applied to an individual active ingredient, administered alone, the term refers to that ingredient alone. When applied to a combination, the term refers to combined amounts of the active ingredients that result in the therapeutic effect, whether administered in combination, serially or simultaneously.

The term "treatment" generally refers to an approach intended to obtain a beneficial or desired result, which may include alleviation of symptoms, or delaying or ameliorating a disease progression.

In a first aspect, the invention provides a synthetic TLR3 agonist comprising a first oligoribonucleotide having the structure: 5'-Domain A-Domain B-3' and a second oligoribonucleotide having the structure: 5'-Domain C-Domain D-3', wherein Domain A is a first complementary domain, Domain B is a polyriboininosine domain, Domain C is a second complementary domain and Domain D is a polyribocytidine domain, wherein Domain A and Domain C are complementary to each other. The first oligoribonucleotide and the second oligoribonucleotide bind to each other through intermolecular hydrogen bonding between either the complementary domains leaving a free polyriboininosine domain and a free polyriboincytidine domain or between the polyriboininosine and polyribocytidine domains leaving a free first complementary domain and a free second complementary domain. Additional first and/or second oligoribonucleotides can bind to the free complementary and/or free polyriboinosine or polyribocytidine domains, thereby creating a chain of oligoribonucleotides.

The invention further provides a synthetic TLR3 agonist comprising a first oligoribonucleotide having the structure: 5'-Domain B-Domain A-3' and a second oligoribonucleotide having the structure: 5'-Domain D-Domain C-3', wherein Domain A is a first complementary domain, Domain B is a polyriboininosine domain, Domain C is a second complementary domain and Domain D is a polyribocytidine domain, wherein Domain A and Domain C are complementary to each other. The first oligoribonucleotide and the second oligoribonucleotide bind to each other through intermolecular hydrogen bonding between either the complementary domains leaving a free polyriboininosine domain and a free polyriboincytidine domain or between the polyriboininosine and polyribocytidine domains leaving a free first complementary domain and a free second complementary domain. Additional first and/or second oligoribonucleotides can bind to the free complementary and/or polyriboinosine or polyribocytidine domains, thereby creating a chain of oligoribonucleotides.

The invention further provides a synthetic TLR3 agonist comprising a first oligoribonucleotide having the structure: 5'-Domain A-3'-3'-Domain B-5' and a second oligoribonucleotide having the structure: 5'-Domain C-3'-3'-Domain D-5', wherein Domains A and B and Domains C and D are covalently linked via a direct nucleotide to nucleotide linkage at their 3' ends through the 3' positions of the sugars or through a modified sugar or modified nucleobase, wherein Domain A is a first complementary domain, Domain B is a polyriboininosine domain, Domain C is a second complementary domain and Domain D is a polyribocytidine domain, wherein Domain A and Domain C are complementary to each other. The first oligoribonucleotide and the second oligoribonucleotide bind to each other through intermolecular hydrogen bonding between either the complementary domains leaving a free polyriboininosine domain and a free polyriboincytidine domain or between the polyriboininosine and polyribocytidine domains leaving a free first complementary domain and a free second complementary domain. Additional first and/or second oligoribonucleotides can bind to the free complementary and/or polyriboinosine or polyribocytidine domains, thereby creating a chain of oligoribonucleotides.

In some embodiments, the TLR3 agonist comprises at least two first oligoribonucleotides having the structure: 5'-Domain A-Domain B-3' covalently linked via a direct nucleotide to nucleotide linkage at their 3' ends through the 3' positions of the sugars or through a modified sugar or modified nucleobase or via a non-nucleotide linker at their 3' ends through the 3' positions of the sugars or through a modified sugar or modified nucleobase and a second oligoribonucleotide having the structure: 5'-Domain C-Domain D-3', wherein Domain A is a first complementary domain, Domain B is a polyriboininosine domain, Domain C is a second complementary domain and Domain D is a polyribocytidine domain, wherein Domain A and Domain C are complementary to each other. In a further embodiment, the at least two first oligoribonucleotides can have the structure 5'-Domain B-Domain A-3' and the second oligoribonucleotide can have the structure 5'-Domain D-Domain C-3'.

In some embodiments, the TLR3 agonist comprises a first oligoribonucleotide having the structure: 5'-Domain A-Domain B-3' and at least two second oligoribonucleotides having the structure: 5'-Domain C-Domain D-3' covalently linked via a direct nucleotide to nucleotide linkage at their 3' ends through the 3' positions of the sugars or through a modified sugar or modified nucleobase or via a non-nucleotide linker at their 3' ends through the 3' positions of the sugars or through a modified sugar or modified nucleobase, wherein Domain A is a first complementary domain, Domain B is a polyriboininosine domain, Domain C is a second complementary domain and Domain D is a polyribocytidine domain, wherein Domain A and Domain C are complementary to each other. In a further embodiment, the first oligoribonucleotide can have the structure 5'-Domain B-Domain A-3' and the at least two second oligoribonucleotides can have the structure 5'-Domain D-Domain C-3'.

As a non-limiting example, the linker may be attached to the 3'-hydroxyl. In such embodiments, the linker comprises a functional group, which is attached to the 3'-hydroxyl by means of a phosphate-based linkage like, for example, phosphodiester, phosphorothioate, phosphorodithioate, methylphosphonate, or by non-phosphate-based linkages. Possible sites of conjugation for the ribonucleotide are indicated in Structure A, below, wherein B represents a heterocyclic base and wherein the arrow pointing to P indicates any attachment to phosphorous.

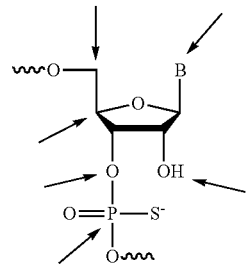

Structure A

In some embodiments, the non-nucleotide linker is a small molecule, macromolecule or biomolecule, including, without limitation, polypeptides, antibodies, lipids, antigens, allergens, and oligosaccharides. In some other embodiments, the non-nucleotidic linker is a small molecule. For purposes of the invention, a small molecule is an organic moiety having a molecular weight of less than 1,000 Da. In some embodiments, the small molecule has a molecular weight of less than 750 Da.

In some embodiments, the small molecule is an aliphatic or aromatic hydrocarbon, either of which optionally can include, either in the linear chain connecting the oligoribonucleotides or appended to it, one or more functional groups including, but not limited to, hydroxy, amino, thiol, thioether, ether, amide, thioamide, ester, urea, or thiourea. The small molecule can be cyclic or acyclic. Examples of small molecule linkers include, but are not limited to, amino acids, carbohydrates, cyclodextrins, adamantane, cholesterol, haptens and antibiotics. However, for purposes of describing the non-nucleotidic linker, the term "small molecule" is not intended to include a nucleoside.

In some embodiments, the non-nucleotidic linker is an alkyl linker or amino linker. The alkyl linker may be branched or unbranched, cyclic or acyclic, substituted or unsubstituted, saturated or unsaturated, chiral, achiral or racemic mixture. The alkyl linkers can have from about 2 to about 18 carbon atoms. In some embodiments such alkyl linkers have from about 3 to about 9 carbon atoms. Some alkyl linkers include one or more functional groups including, but not limited to, hydroxy, amino, thiol, thioether, ether, amide, thioamide, ester, urea, and thioether. Such alkyl linkers can include, but are not limited to, 1,2 propanediol, 1,2,3 propanetriol, 1,3 propanediol, triethylene glycol hexaethylene glycol, polyethylene glycollinkers (e.g. [—O—$CH_2$—$CH_2$—]$_n$ (n=1-9)), methyl linkers, ethyl linkers, propyl linkers, butyl linkers, or hexyl linkers. In some embodiments, such alkyl linkers may include peptides or amino acids.

In some embodiments, the non-nucleotide linker may include, but is not limited to, the following:

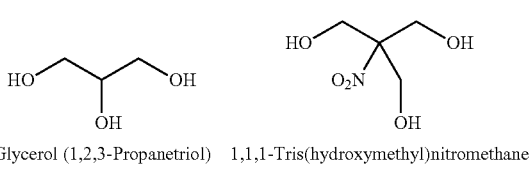

Glycerol (1,2,3-Propanetriol)  1,1,1-Tris(hydroxymethyl)nitromethane

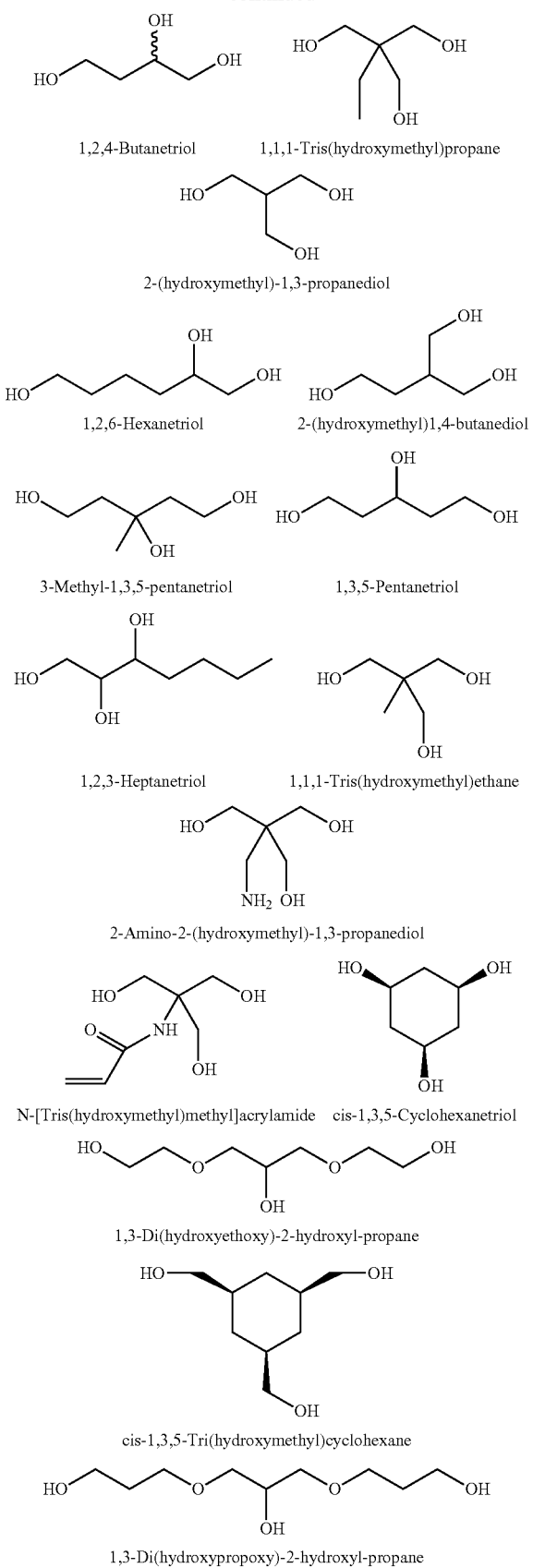
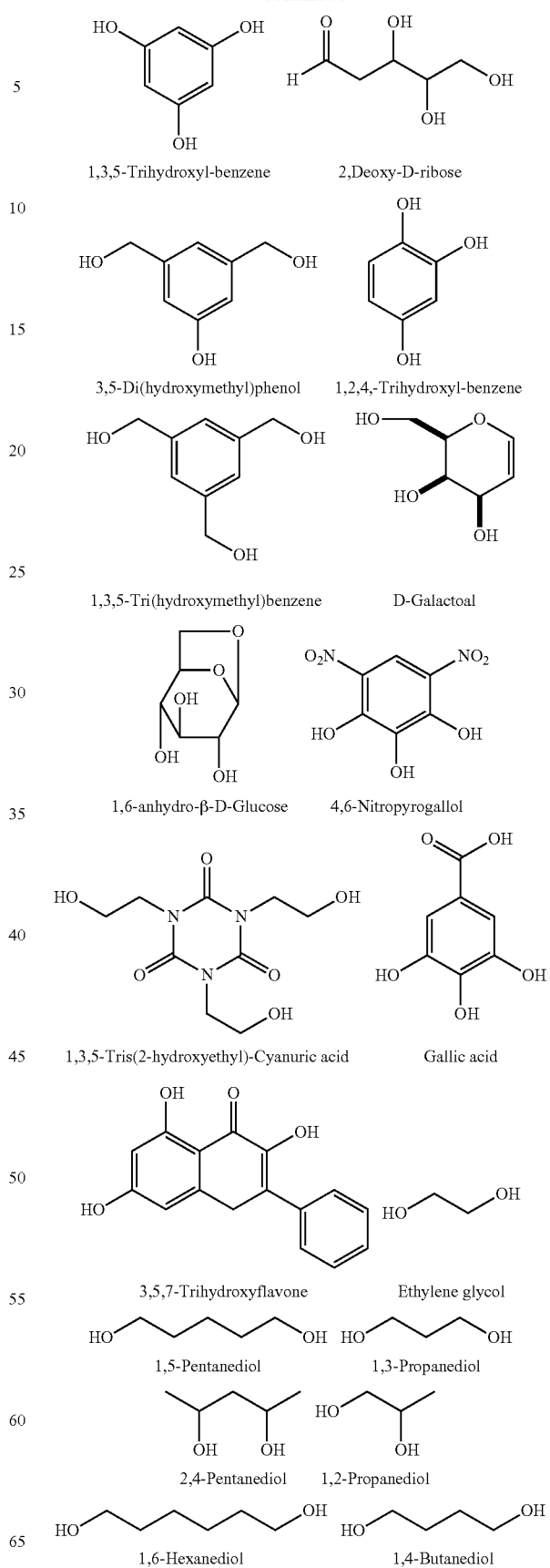

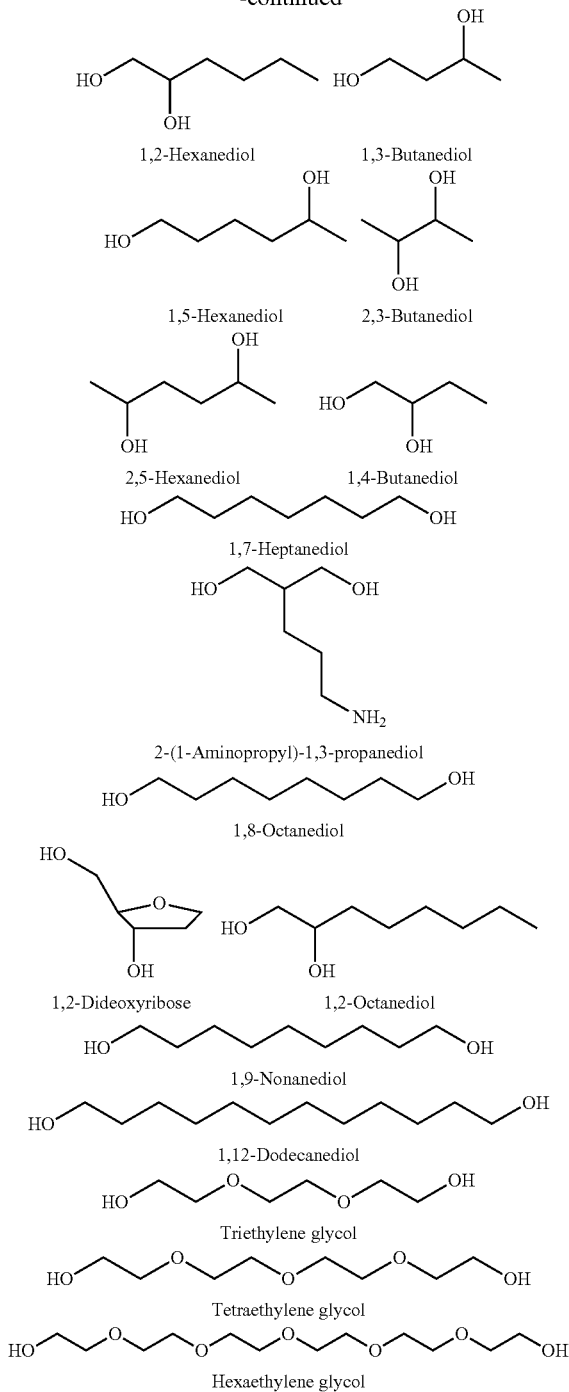

In some embodiments, the small molecule linker is glycerol or a glycerol homolog of the formula HO—$(CH_2)_o$—CH(OH)—$(CH_2)_p$—OH, wherein o and p independently are integers from 1 to about 6, from 1 to about 4, or from 1 to about 3. In some other embodiments, the small molecule linker is a derivative of 1,3-diamino-2-hydroxypropane. Some such derivatives have the formula HO—$(CH_2)_m$—C(O)NH—$CH_2$—CH(OH)—$CH_2$—NHC(O)—$(CH_2)_m$—OH, wherein m is an integer from 0 to about 10, from 0 to about 6, from 2 to about 6, or from 2 to about 4.

Some non-nucleotide linkers according to the invention permit attachment of more than two oligoribonucleotides. For example, the small molecule linker glycerol has three hydroxyl groups to which oligoribonucleotides may be covalently attached. Some TLR3 agonist according to the invention, therefore, comprise two or more oligoribonucleotides linked to a nucleotide or a non-nucleotide linker. Such TLR3 agonist are referred to as being "branched".

Without wishing to be bound to any particular theory, the formation of a chain of first and second oligoribonucleotides of the invention results in a hybrid poly(I:C) that is a specific agonist of TLR3. Specifically, the hybrid poly(I:C) TLR3 agonist of the invention can exists as long strands of nucleic acid but that have reduced ability to form undesirable helix-with-loop structures and that do not have toxic properties or the lack of efficacy when administered in vivo.

As used herein, the term "complementary" means having the ability to hybridize to a nucleic acid. Such hybridization is ordinarily the result of hydrogen bonding between complementary strands, preferably to form Watson-Crick or Hoogsteen base pairs. Intermolecular hydrogen bonding results in the formation of a double-stranded nucleic acid molecule.

In embodiments of this aspect of the invention, the first complementary domain, as used herein, refers to a domain having a base sequence which, upon suitable alignment with the second complementary domain, may form intermolecular basepairing between G-C, A-T, A-U and/or G-U wobble pairs. Thus, where a plurality of first and second oligoribonucleotides are used together, the complementary domains of the plurality of first oligoribonucleotides and the complementary domains of the plurality of second oligoribonucleotides are capable of hybridizing together through intermolecular hydrogen bonding under high stringency conditions. For example, in some embodiments, the degree of complementarity is at least 93 percent, at least 95 percent, at least 98 percent, or even 100 percent. In preferred embodiments, the degree of complementarity is 100%. Additionally, where a plurality of first and second oligoribonucleotides are used together, the polyriboinosine domains of the plurality of first oligoribonucleotides and the polyribocytidine domains of the plurality of second oligoribonucleotides are capable of hybridizing together.

"Stringency conditions" for hybridizations is a term of art referring to the conditions (e.g., temperature and buffer concentration) that permit hybridization of a particular nucleic acid to another nucleic acid in which the first nucleic acid may be perfectly complementary to the second, or the first and second may share some degree of complementarity that is less than perfect. "High stringency conditions" and "moderate stringency conditions" for nucleic acid hybridizations are explained on pages 2.10.1-2.10.16 (see particularly 2.10.8-11) and pages 6.3.1-6 in Current Protocols in Molecular Biology (Ausubel, F. M. et al., eds., Vol. 1, containing supplements up through Supplement 29, 1995), the teachings of which are hereby incorporated by reference. Hybridization requires that the two nucleic acids contain substantially complementary sequences; depending on the stringency of hybridization, however, mismatches may be tolerated. The appropriate stringency for hybridizing nucleic acids depends on the length of the nucleic acids and the degree of complementarily, variables well known in the art.

In some embodiments, although the first and second oligoribonucleotides are the same number of nucleotides in length, the complementary domains do not necessarily have the same number of nucleotides as the polyriboinosine and polyribocytidine domains. The only requirement is that the first complementary domain and the second complementary domain are the same length and that the polyriboinosine and polyribocytidine domains are the same length. For example, the first and second complementary domains are from about 10 to about 20 nucleotides in length and the polyriboinosine and polyribocytidine domains are from about 30 to about 40 nucleotides in length. In certain embodiments the first and second complementary domains are from about 15 to about 20 nucleotides in length and the polyriboinosine and polyribocytidine domains are from about 30 to about 35 nucleotides in length. In some embodiments, the first and second complementary domains are 10, 11, 12, 13, 14, 15, 16, 17, 18, 19 or 20 nucleotides in length and the polyriboinosine and polyribocytidine domains are 30, 31, 32, 33, 34, 35, 36, 37, 38, 39 or 40 nucleotides in length. In some embodiments, the first and second complementary domains are 20 nucleotides in length and the polyriboinosine and polyribocytidine domains are 30 nucleotides in length. In some embodiments, the first and second complementary domains are 15 nucleotides in length and the polyriboinosine and polyribocytidine domains are 35 nucleotides in length. One skilled in the art would understand that the different Domains of the first and second oligoribonucleotides may be shorter or longer as long as the compound retains it TLR3 stimulatory activity without introducing the undesired helix-with-loop structures and toxic properties.

In embodiments of this aspect of the invention, the first and second oligoribonucleotides can have the following exemplary structures:

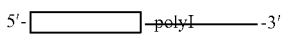

Formula I

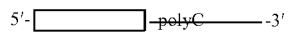

Formula II

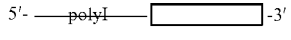

Formula III

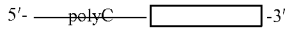

Formula IV

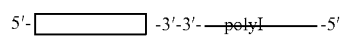

Formula V

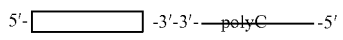

Formula VI

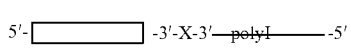

Formula VII

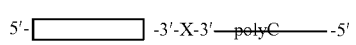

Formula VIII wherein the ☐ represents the complementary domains.

As would be recognized by one skilled in the art, the complementary sequences of the first and second complementary domains and/or the complementary nature of the polyriboinosine and polyribocytidine domains allows for intermolecular hydrogen bonding between the first and second oligoribonucleotides which can have the following exemplary double stranded structures:

Formula IX (e.g., Formulas I and II)

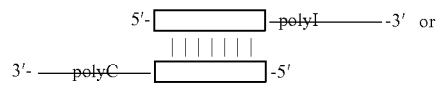

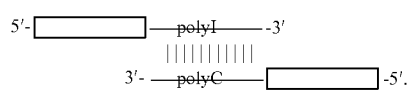

Additional first and second oligoribonucleotides can bind together thereby creating a chain of oligoribonucleotides according to the invention which can have the following exemplary structure:

Formula X (e.g., chain of Formulas I and II)

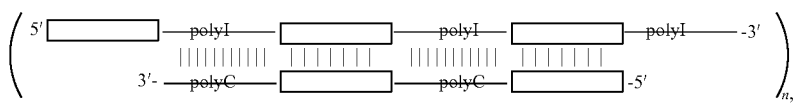

wherein n is any number.

As would be recognized by one skilled in the art, double strand structures and/or chains of first and second oligoribonucleotides can also be prepared with Formulas III and IV, Formulas V and VI and Formulas VII and VIII.

In some embodiments, the TLR3 agonist according, to the invention can comprise one or more force binding sites. A force binding site is achieved by the substitution of one or more guanosine(s) for inosine in the polyriboiniosine domain. Such a force binding site can improve the alignment of the polyriboiniosine and polyribocytidine domains and/or increase the strength of the bond between the polyriboiniosine and polyribocytidine domains.

In some embodiments of this aspect of the invention, certain hydrogen atoms in the first and/or second oligoribonucleotide are replaced by a deuterium atom through hydrogen deuterium exchange (also called H-D or H/D exchange). By replacing a hydrogen atom with a deuterium atom, the stability of the TLR3 agonist is improved. Additionally, such an exchange increases the TLR3 agonists resistance to oxidation and/or degradation.

In other embodiments, the TLR3 agonist can comprise a 5' and/or 3' cap, wherein the 5' and/or 3' end of the TLR3 agonist is attached to another molecule (e.g. a non-nucleotidic linker) or to itself such that the 5' and/or 3' end is not accessible exonuclease degradation or for hybridization to another TLR3 agonist of the invention. Such capping acts to further stabilize the TLR3 agonist and/or to regulate the number of first and second oligoribonucleotides that can bind together and, thereby, allows for a TLR3 agonist having a particular size or length.

In further embodiments, the TLR3 agonist according to the first aspect of the invention can comprise one or more deuterium atom exchanges. Such deuterium exchanges would be recognized to provide increased resistance to nuclease degradation and/or to increase the stability of hybridization between the first and second oligoribonucleotides and/or to enhance the stability of binding by TLR3. Additionally, such deuterated molecules may comprise a 5' and/or 3' cap.

In further embodiments, the invention provides a composition comprising one or more of the TLR3 agonists according to the invention and any other therapeutic or prophylactic agent including, but not limited to, one or more vaccines, antigens, antibodies, cytotoxic agents, allergens, antibiotics, antisense oligonucleotides, TLR agonist, TLR antagonist, siRNA, miRNA, peptides, proteins, gene therapy vectors, DNA vaccines, adjuvants or kinase inhibitors to enhance the specificity or magnitude of the immune response, or co-stimulatory molecules such as cytokines, chemokines, protein ligands, trans-activating factors, peptides and peptides comprising modified amino acids.

In a second aspect, the invention provides a composition comprising a TLR3 agonist according to the first aspect of the invention and a physiologically acceptable carrier.

In certain embodiments, the TLR3 agonist is included in the pharmaceutically acceptable carrier in an amount sufficient to deliver to a mammal a pharmaceutically effective amount without causing serious toxic effects. The effective dosage range of the pharmaceutically acceptable derivatives can be calculated based on the weight of the parent compound to be delivered, or by other means known to those skilled in the art.

In further embodiments, the composition comprising one or more of the TLR3 agonists according to the invention and a physiologically acceptable carrier, further comprises any other therapeutic or prophylactic agent including, but not limited to, one or more vaccines, antigens, antibodies, cytotoxic agents, allergens, antibiotics, antisense oligonucleotides, TLR agonist, TLR antagonist, for example TLR7 and/or TLR8 antagonist, siRNA, miRNA, peptides, proteins, gene therapy vectors, DNA vaccines, adjuvants or kinase inhibitors to enhance the specificity or magnitude of the immune response, or co-stimulatory molecules such as cytokines, chemokines, protein ligands, trans-activating factors, peptides and peptides comprising modified amino acids. In a preferred embodiment, the composition comprising one or more of the TLR3 agonists according to the invention and a physiologically acceptable carrier, further comprises one or more antigens.

In a third aspect, the invention provides a method for generating a TLR3-mediated immune response in mammals. In this method, a TLR3 agonist according to the first or second aspect of the invention is contacted with or bound by TLR3 in vitro, in vivo, ex vivo or in a cell. For purposes of this invention, the term "mammal" is expressly intended to include humans and animals. In preferred embodiments, the compound, composition or vaccine is administered to a vertebrate in need of immune stimulation.

In a further embodiment, the invention provides a vaccine. Vaccines according to this aspect comprise a composition according to the invention, and further comprise an antigen. An antigen is a molecule that elicits a specific immune response. Such antigens include, without limitation, proteins, peptides, nucleic acids, carbohydrates and complexes or combinations of any of the same. Antigens may be natural or synthetic and generally induce an immune response that is specific for that antigen. Any such antigen may optionally be linked to an immunogenic protein, such as keyhole limpet hemocyanin (KLH), cholera toxin B subunit, or any other immunogenic carrier protein.

Vaccines according to the invention may further include any of the plethora of known adjuvants, including, without limitation, Freund's complete adjuvant, KLH, monophosphoryl lipid A (MPL), alum, Merck alum adjuvant (MAA) and saponins, including QS-21, imiquimod, R848, or combinations thereof.

In a fourth aspect, the invention provides a method for stimulating TLR3 activity in a mammal such method comprising administering to the mammal a TLR3 agonist according to the first or second aspect of the invention. In some embodiments the mammal is a human. In preferred embodiments, the TLR3 agonist according to the first or second aspect of the invention is administered to a mammal in need of immune stimulation.

In a fifth aspect, the invention provides a method for stimulating TLR3-mediated immune response in a mammal, such method comprising administering to the mammal a TLR3 agonist according to the first or second aspect of the invention. In some embodiments the mammal is a human. In preferred embodiments, the TLR3 agonist according to the first or second aspect of the invention is administered to a mammal in need of immune stimulation.

In a sixth aspect, the invention provides a method for treating a mammal having a disease or disorder treatable by TLR3 activation or TLR3-mediated immune stimulation, such method comprising administering to the mammal a TLR3 agonist according to the first or second aspect of the invention in a pharmaceutically effective amount. In some embodiments the mammal is a human. The invention also relates to the TLR3 agonist and compositions thereof, which are disclosed herein in methods of treating diseases and illnesses, for use in treating diseases and illnesses and for use as vaccine adjuvants.

In a seventh aspect, the invention provides methods for preventing a disease or disorder or for use as vaccine adjuvants in a mammal, particularly a human, at risk of contracting or developing a disease or disorder preventable by TLR3 activation or TLR3-mediated stimulation of an immune response. The method according to this aspect comprises administering to the mammal a prophylactically effective amount of a TLR3 agonist according to the first or second aspect of the invention.

In an eighth aspect, the TLR3 agonists and compositions thereof according to the invention are also useful for examining the function of the TLR3 gene in a cell or in a control mammal or in a mammal afflicted with a disease associated with TLR3 or immune stimulation through TLR3. In embodiments of this aspect, the cell or mammal is administered the TLR3 agonist according to the first or second aspects of the invention, and the activity of TLR3 is examined.

A non-limiting list of TLR3 agonists according to the invention are shown in Table 2 below. In Table 2, the oligonucleotide-based TLR3 agonist compounds have all phosphodiester (PO) linkages, except where indicated as a phosphorothioate (PS) linkage. Those skilled in the art will recognize, however, that a mixture of PS and PO linkages can be used. A list of inactive, control oligonucleotides are shown as compounds nos. 8, 20-24, 64-67, 119-121, 124 and 125 in Table 2 below. In Table 2, the inactive, control oligonucleotides have all phosphodiester (PO) linkages, except where indicated as a phosphorothioate (PS) linkage.

TABLE 2

| SEQ ID NO. | Compound No. | | Sequence | Length |
|---|---|---|---|---|
| 1 | 25 | a | 5'-GCAGUUGACACCCCCCCCCCCCCCCCCCCCCCCCCCCC-3' | 40 |
| 2 | | b | 3'-IIIIIIIIIIIIIIIIIIIIIIIIIIIIIICGUCAACUGU-5' | 40 |
| 3 | 27 | a | 5'-CACUGGCAGUUGACACCCCCCCCCCCCCCCCCCCCCCCCCCCCCCCCCC-3' | 50 |
| 4 | | b | 3'-IIIIIIIIIIIIIIIIIIIIIIIIIIIIIIIIIIIIIIIIGUGACCGUCAACUGU-5' | 50 |
| 5 | 28 | a | 5'-CACUGGCAGUUGACACAGGUCCCCCCCCCCCCCCCCCCCCCCCCCCCC-3' | 50 |
| 6 | | b | 3'-IIIIIIIIIIIIIIIIIIIIIIIIIIIIIIIIIIIGUGACCGUCAACUGUGUCCA-5' | 50 |
| 7 | 29 | a | 5'-CACUGGCAGUUGACACCCCCCCCCCCCCCCCCCCCCCCCCCCCCCCCCC-3' | 50 |
| 8 | | b | 5'-UGUCAACUGCCAGUGIIIIIIIIIGIIIIIIIIIIGIIIIIIIIIIGIIII-3' | 50 |
| 9 | 30 | a | 5'-CACUGGCAGUUGACACCCCCCCCCCCCCCCCCCCCCCCCCCCCCCCCCC-3' | 50 |
| 10 | | b | 3'-IIIIIIIIIIIIIIIIIIIIIIIIIIIIIIIIIIIIIIIIGUGACCGUCAACUGU-5' | 50 |
| 11 | 31 | a | 5'-<u>CACUGGCAGUUGACA</u>CCCCCCCCCCCCCCCCCCCCCCCCCCCCCCCCCC-3' | 50 |
| 12 | | b | 3'-IIIIIIIIIIIIIIIIIIIIIIIIIIIIIIIIIIIIIIIIGUGACCGUCAACUGU-5' | 50 |
| 13 | 32 | a | 5'-CACUGGCAGUUGACACCCCCCCCCCCCCCCCCCCCCCCCCCCCCCCCCC-X-CCCCCCCCCCCCCCCCCCCCCCCCCCCCCCCCCCCACAGUUGACGGUCAC-5' | 100 |
| 14 | | b | 3'-IIIIIIIIIIIIIIIIIIIIIIIIIIIIIIIIIIIIIIIIGUGACCGUCAACUGU-5' | 50 |
| 15 | 33 | a | 5'-CCCCCCCCCCCCCCCCCCCCCCCCCCCCCCCCCCCCCACUGGCAGUUGACA-X-ACAGUUGACGGUCACCCCCCCCCCCCCCCCCCCCCCCCCCCCCCCCCCC-5' | 100 |
| 16 | | b | 3'-IIIIIIIIIIIIIIIIIIIIIIIIIIIIIIIIIIIIIIIIGUGACCGUCAACUGU-5' | 50 |
| 17 | 34 | a | 5'-CACUGGCAGUUGACACCCCCCCCCCCCCCCCCCCCCCCCCCCCCCCCCC-3' | 50 |
| 18 | | b | 5'-UGUCAACUGCCAGUGIIIGIIIIGIIIIGIIIIGIIIIGIIIIGIIII-3' | 50 |
| 19 | 35 | a | 5'-CACUGGCAGUUGACACCCCCCCCCCCCCCCCCCCCCCCCCCCCCCCCCC-3' | 50 |
| 20 | | b | 5'-UGUCAACUGCCAGUGIIGIIGIIIIGIIGIIGIIIGIIGIIGIIIGIIII-3' | 50 |
| 21 | 1 | a | 5'-CCUCCAGCCUUACAGCCAAGUAUGAGAGCU-3' | 30 |
| 22 | | b | 3'-GGAGGUCGGAAUGUCGGUUCAUACUCUCGA-5' | 30 |
| 23 | 2 | a | 5'-GGGAGACAGGCCUGUUCCAUGGCCAACACGUUUGUCUCCC-3' | 40 |
| 24 | | b | 3'-CCCUCUGUCCGGACAAGGUACCGGUUGUGCAAACAGAGGG-5' | 40 |
| 25 | 3 | a | 5'-CUGAACAUCUGCGGACGGACCUAGAUACGGAACCUUUGUU-3' | 40 |
| 26 | | b | 3'-GACUUGUAGACGCCUGCCUGGAUCUAUGCCUUGGAAACAA-5' | 40 |
| 27 | 4 | a | 5'-ACAUCUGCGGACGGACCUAGAUACGGAACCUUUGUUGUUG-3' | 40 |
| 28 | | b | 3'-UGUAGACGCCUGCCUGGAUCUAUGCCUUGGAAACAACAAC-5' | 40 |
| 29 | 5 | a | 5'-XCCCCCCCCCCCCCCCCCCCCCCX-3' | 24 |
| 30 | | b | 3'-XIIIIIIIIIIIIIIIIIIIIIIX-5' | 24 |
| 31 | 6 | a | 5'-CCCCCCCCCCCCCCCCCCCCCCCCCCCCCC-3' | 30 |
| 32 | | b | 3'-IIIIIIIIIIIIIIIIIIIIIIIIIIIIII-5' | 30 |
| 33 | 7 | a | 5'-CCCCCCCCCCCCCCCCCCCCCCCCCCCCCC-3' | 30 |
| 34 | | b | 3'-IIIIIIIIIIIIIIIIIIIIIIIIIIIIII-5' | 30 |
| 35 | 8 | a | 5'-CCCCCCCCCCCCCCCCCCCCCCCCCCCCCCCCCCCCCCCCCCCCC-3' | 45 |
| 36 | | b | 3'-IIIIIIIIIIIIIIIIIIIIIIIIIIIIIIIIIIIIIIIIIIIII-5' | 45 |
| 37 | 9 | a | 5'-CCUCCAGCCUUACAGCCAAGUAUGAYYYYYCCUCCAGCCUUACAGCCAAGUAUGA-3' | 55 |
| 38 | | b | 3'-GGAGGUCGGAAUGUCGGUUCAUACU-5' | 25 |
| 39 | 10 | a | 5'-CCUCCAGCCUUACAGCCAAGUAUGAYYYYYYYYYYCCUCCAGCCUUACAGCCAAGUAUGA-3' | 60 |
| 40 | | b | 3'-GGAGGUCGGAAUGUCGGUUCAUACU-5' | 25 |
| 41 | 11 | a | 5'-CCUCCAGCCUUACAGCCAAGUAUGAYYYYYYYYYYYYYYYCCUCCAGCCUUACAGCCAAGUAUGA-3' | 65 |
| 42 | | b | 3'-GGAGGUCGGAAUGUCGGUUCAUACU-5' | 25 |
| 43 | 12 | a | 5'-GGGAGACAAACGUGUUGGCCAUGGAACAGGCCUGUCUCCC-X-CCCUCUGUCCGGACAAGGUACCGGUUGUGCAAACAGAGGG-5' | 81 |
| 44 | | b | 3'-CCCUCUGUUUGCACAACCGGUACCUUGUCCGGACAGAGGG-5' | 40 |
| 45 | 13 | a | 3'-CCCUCUGUCCGGACAAGGUACCGGUUGUGCAAACAGAGGG-X-GGGAGACAAACGUGUUGGCCAUGGAACAGGCCUGUCUCCC-3' | 81 |
| 46 | | b | 5'-GGGAGACAGGCCUGUUCCAUGGCCAACACGUUUGUCUCCC-3' | 40 |
| 47 | 14 | | 5'-CCCIIICCCII-X-IICCCIIICCC-5' | 23 |

TABLE 2-continued

| SEQ ID NO. | Compound No. | | Sequence | Length |
|---|---|---|---|---|
| 48 | 15 | | 5'-CCIICCIICCC-X-CCCIICCIICC-5' | 23 |
| 49 | 16 | | 5'-CCIICCIICCLCCIICCIICC-3' | 23 |
| 50 | 17 | a | 5'-XCCCCCCCCCCC-X-CCCCCCCCCCCX-3' | 25 |
| 51 | | b | 5'-XIIIIIIIIIIIIIIIIIIIIIIX-3' | 24 |
| 52 | 18 | | 5'-IIIIIIIIIIIII-X-CCCCCCCCCCCCC-5' | 27 |
| 53 | 19 | | 5'-ICICICICICICICI-X-ICICICICICICICI-5' | 31 |
| 54 | 20 | a | 5'-CCCACACCC-3' | 9 |
| 55 | | b | 3'-IIIIIIUGU-5' | 9 |
| 56 | 21 | a | 5'-CCCCCCACACCCCCC-3' | 15 |
| 57 | | b | 3'-IIIIIIIIIIIIUGU-5' | 15 |
| 58 | 22 | a | 5'-IIIIIIIIIIIIIIIC$_3$GUGC-3' | 20 |
| 59 | | b | 3'-GC$_3$AC$_3$GCCCCCCCCCCCCCCC-5' | 20 |
| 60 | 23 | a | 5'-CCCCCCCCCACACCCCCCCCC-3' | 23 |
| 61 | | b | 3'-IIIIIIIIIIIIIIIIIIIIUGU-5' | 23 |
| 62 | 24 | a | 5'-GACACCCCCCCCCCCCCCCCCCCCCCCCCCCC-3' | 34 |
| 63 | | b | 3'-IIIIIIIIIIIIIIIIIIIIIIIIIIIIIICUGU-5' | 34 |
| 64 | 26 | a | 5'-CACUGGCAGUUGACACAGGUUCCUCACUUCACAAAUCGUUCCCCCCCCCC-3' | 50 |
| 65 | | b | 3'-IIIIIIIIIIGUGACCGUCAACUGUGUCCAAGGAGUGAAGUGUUUAGCAA-5' | 50 |
| 66 | 36 | a | 5'-CACUGGCAGUUGACACAGGUUCCUCACUUCACAAAUCGUUCAUCGCCCCC-3' | 50 |
| 67 | | b | 3'-IIIIIGUGACCGUCAACUGUGUCCAAGGAGUGAAGUGUUUAGCAAGUAGC-5' | 50 |
| 68 | 37 | a | 5'-CACUGGCAGUUGACACAGGUUCCUCACUUCCCCCCCCCCCCCCCCCCCCC-3' | 50 |
| 69 | | b | 3'-IIIIIIIIIIIIIIIIIIIIIGUGACCGUCAACUGUGUCCAAGGAGUGAAG-5' | 50 |
| 70 | 38 | a | 5'-CACUGCUCAUUCACACCCCCCCCCCCCCCCCCCCCCCCCCCCCCCCCCCC-3' | 50 |
| 71 | | b | 3'-IIIIIIIIIIIIIIIIIIIIIIIIIIIIIIIIIIGUGACGAGUAAGUGU-5' | 50 |
| 72 | 39 | a | 5'-GUCACAGUCAAGUUCCCCCCCCCCCCCCCCCCCCCCCCCCCCCCCCCCCC-3' | 50 |
| 73 | | b | 3'-IIIIIIIIIIIIIIIIIIIIIIIIIIIIIIIIIIIICAGUCAGUUCAAG-5' | 50 |
| 74 | 40 | a | 5'-CGUGAACUGACACUGCCCCCCCCCCCCCCCCCCCCCCCCCCCCCCCCCCC-3' | 50 |
| 75 | | b | 3'-IIIIIIIIIIIIIIIIIIIIIIIIIIIIIIIIIIIIGCACUUGACUGUGAC-5' | 50 |
| 76 | 41 | a | 5'-CACUGGCAGUUGACACAGGUCCCCCCCCCCCCCCCCCCCCCCCCCCCCCCCCCCCCCCCC-3' | 60 |
| 77 | | b | 3'-IIIIIIIIIIIIIIIIIIIIIIIIIIIIIIIIIIIIIIIIGUGACCGUCAACUGUGUCCA-5' | 60 |
| 78 | 42 | a | 5'-CACUGGCAGUUGACACCCCCCCCCCCCCCCCCCCCCCCCCCCCCCCCCCCCCCCCCCCCC-3' | 60 |
| 79 | | b | 3'-IIIIIIIIIIIIIIIIIIIIIIIIIIIIIIIIIIIIIIIIIIIIIIGUGACCGUCAACUGU-5' | 60 |
| 80 | 43 | a | 5'-CACUGGCAGUUGACACCCCCCCCCCCCCCCCCCCCCCCCCCCCCCCCCCC-3' | 50 |
| 81 | | b | 3'-IIIIGIIIIGIIIIGIIIIGIIIIGIIIIGIIIIIGUGACCGUCAACUGU-5' | 50 |
| 82 | 44 | a | 5'-CACUGGCAGUUGACACCCCCCCCCCCCCCCCCCCCCCCCCCCCCCCCCCC-3' | 50 |
| 83 | | b | 3'-IIGIIGIIGIIGIIGIIGIIGIIGIIGIIGIIGIIGIIGUGACCGUCAACUGU-5' | 50 |
| 84 | 45 | a | 5'-CACUGGCAGUUGACACCCCUCCCCCCCCCUCCCCCCCCCUCCCCCCCCCC-3' | 50 |
| 85 | | b | 3'-IIIIAIIIIIIIIAIIIIIIIIIAIIIIIIIIIIGUGACCGUCAACUGU-5' | 50 |
| 86 | 46 | a | 5'-CACUGGCAGUUGACACCCCCCCCCCCCCCCCCCCCCCCCCCCCCCCCCCC-3' | 50 |
| 87 | | b | 3'-IIIIG$_1$IIIIIIIIG$_1$IIIIIIIIG$_1$IIIIIIIIIGUGACCGUCAACUGU-5' | 50 |
| 88 | 47 | a | 5'-CACUGGCAGUUGACACCCCC$_1$CCCCCCCCCC$_1$CCCCCCCCCC$_1$CCCCCCCCCC-3' | 50 |
| 89 | | b | 3'-IIIIGIIIIIIIIGIIIIIIIIGIIIIIIIIIIGUGACCGUCAACUGU-5' | 50 |
| 90 | 48 | a | 5'-CACUGGCAGUUGACACCCCCCCCCCCCCCCCCCCCCCCCCCCCCCCCCCC-3' | 50 |
| 91 | | b | 3'-IIIIG$_2$IIIIIIIIG$_2$IIIIIIIIG$_2$IIIIIIIIIGUGACCGUCAACUGU-5' | 50 |
| 92 | 49 | a | 5'-CACUGGCAGUUGACACCCCCC$_1$CCCCCCCCCC$_1$CCCCCCCCCC$_1$CCCCCCCCCC-3' | 50 |
| 93 | | b | 3'-IIIIG$_2$IIIIIIIIG$_2$IIIIIIIIG$_2$IIIIIIIIIGUGACCGUCAACUGU-5 | 50 |
| 94 | 50 | a | 5'-CACUGGCAGUUGACACCCCC$_2$CCCCCCCCCC$_2$CCCCCCCCCC$_2$CCCCCCCCCC-3' | 50 |
| 95 | | b | 3'-IIIIIIIIIIIIIIIIIIIIIIIIIIIIIIIIIIIIGUGACCGUCAACUGU-5' | 50 |
| 96 | 51 | a | 5'-<u>CACUGGCAGUUGACA</u>CCCCCCCCCCCCCCCCCCCCCCCCCCCCCCCCCC-3' | 50 |
| 97 | | b | 3'-IIIIIIIIIIIIIIIIIIIIIIIIIIIIIIIIIIIIGUGACCGUCAACUGU-5' | 50 |

TABLE 2-continued

| SEQ ID NO. | Compound No. | | Sequence | Length |
|---|---|---|---|---|
| 98 | 52 | a | 5'-<u>CACUGGCAGUUGACA</u>CCCCCCCCCCCCCCCCCCCCCCCCCCCCCCCCC-3' | 50 |
| 99 | | b | 3'-IIIIIIIIIIIIIIIIIIIIIIIIIIIIIIIIIIIGUGACCGUCAACUGU-5' | 50 |
| 100 | 53 | a | 5'-CACUGGCAGUUGACA<u>CCCCCCCCCCCCCCCCCCCCCCCCCCCCCCCCC</u>-3' | 50 |
| 101 | | b | 3'-IIIIIIIIIIIIIIIIIIIIIIIIIIIIIIIIIIIGUGACCGUCAACUGU-5' | 50 |
| 102 | 54 | a | 5'-CACUGGCAGUUGACA<u>CCCCCCCCCCCCCCCCCCCC</u>CCCCCCCCCCCCCC-3' | 50 |
| 103 | | b | 3'-IIIIIIIIIIIIIIIIIIIIIIIIIIIIIIIIIIIGUGACCGUCAACUGU-5' | 50 |
| 104 | 55 | a | 5'-CACUGGCAGUUGACA<u>CCCCCCCCCCCCCCCCCCCCCCCCCCCCCCCCC</u>-3' | 50 |
| 105 | | b | 3'-IIIIIIIIIIIIIIIIIIIIIIIIIIIIIIIIIIIGUGACCGUCAACUGU-5' | 50 |
| 106 | 56 | a | 5'-CACUGGCAGUUGACACCCCCCCCCCCCCCCCCCCCCCCCCCCCCCCCCCC-3' | 50 |
| 107 | | b | 3'-IIIIIIIIIIIIIIIIIIIIIIIIIIIIIIIIIII<u>GUGACCGUCAACUGU</u>-5' | 50 |
| 108 | 57 | a | 5'-<u>CACUGGCAGUUGACA</u>CCCCCCCCCCCCCCCCCCCCCCCCCCCCCCCCC-3' | 50 |
| 109 | | b | 3'-IIIIIIIIIIIIIIIIIIIIIIIIIIIIIIIIIII<u>GUGACCGUCAACUGU</u>-5' | 50 |
| 110 | 58 | a | 5'-CACUGGCAGUUGACACCCCCCCCCCCCCCCCCCCCCCCCCCCCCCCCC-3' | 50 |
| 111 | | b | 3'-IIIIIIIIIIIIIIIIIIIIIIIIIIIIIIIIIIIGUGACCGUCAACUGU-5' | 50 |
| 112 | 59 | a | 5'-CACUGGCAGUUGACACCCCCUCCCCCCCCCUCCCCCCCCCUCCCCCCCCC-3' | 50 |
| 113 | | b | 3'-IIIIIIIIIIIIIIIIIIIIIIIIIIIIIIIIIIIGUGACCGUCAACUGU-5' | 50 |
| 114 | 60 | a | 5'-CACUGGCAGUUGACACCCCCCCCCCCCCCCCCCCCCCCCCCCCCCCCCCC-3' | 50 |
| 115 | | b | 3'-IIIIAIIIIIIIIIAIIIIIIIIAIIIIIIIIIIIGUGACCGUCAACUGU-5' | 50 |
| 116 | 61 | a | 5'-CACUGGCAGUUGACA-3'-3'-CCCCCCCCCCCCCCCCCCCCCCCCCCCCCCCCC-5' | 50 |
| 117 | | b | 5'-UGUCAACUGCCAGUG-3'-3'-IIIIIIIIIIIIIIIIIIIIIIIIIIIIIIIIIII-5' | 50 |
| 118 | 62 | a | 5'-CACUGGCAGUUGACA-3'-3'-CCCCCCCCCCCCCCCCCCCCCCCCCCCCCCCCC-5' | 50 |
| 119 | | b | 3'-IIIIIIIIIIIIIIIIIIIIIIIIIIIIIIIIIIIGUGACCGUCAACUGU-5' | 50 |
| 120 | 63 | a | 5'-CACUGGCAGUUGACACCCCCCCCCCCCCCCCCCCCCCCCCCCCCCCCCCC-3' | 50 |
| 121 | | b | 5'-UGUCAACUGCCAGUG-3'-3'-IIIIIIIIIIIIIIIIIIIIIIIIIIIIIIIIIII-5' | 50 |
| 122 | 64 | a | 5'-CACUGGCAGUUGACA-3' | 15 |
| 123 | | b | 3'-GUGACCGUCAACUGU-5' | 15 |
| 124 | 65 | a | 5'-CACUGGCAGUUGACACACUGGCAGUUGACACACUGGCAGUUGACA-3' | 45 |
| 125 | | b | 3'-GUGACCGUCAACUGUGUGACCGUCAACUGUGUGACCGUCAACUGU-5' | 45 |
| 126 | 66 | a | 5'-CCCCCCCCCCCCCCCCCCCCCCCCCCCCCCCCCCCACUGGCAGUUGACA-3' | 50 |
| 127 | | b | 3'-IIIIIIIIIIIIIIIIIIIIIIIIIIIIIIIIIIIGUGACCGUCAACUGU-5' | 50 |
| 128 | 67 | a | 5'-UGUCAACUGCCAGUGCCCCCCCCCCCCCCCCCCCCCCCCCCCCCCCCCCC-3' | 50 |
| 129 | | b | 3'-CCCCCCCCCCCCCCCCCCCCCCCCCCCCCCCCCCCACAGUUGACGGUCAC-5' | 50 |
| 130 | 68 | a | 5'-CACUGGCAGUUGACAIIIIIIIIIIIIIIIIIIIIIIIIIIIIIIIIIII-3' | 50 |
| 131 | | b | 3'-IIIIIIIIIIIIIIIIIIIIIIIIIIIIIIIIIIIGUGACCGUCAACUGU-5' | 50 |
| 132 | 69 | a | 5'-CAAGGCAAGCAUUCGCCCCCCCCCCCCCCCCCCCCCCCCCCCCCCCCCCC-3' | 50 |
| 133 | | b | 3'-IIIIIIIIIIIIIIIIIIIIIIIIIIIIIIIIIII GUUCCGUUCGUAAGC-5' | 50 |
| 134 | 70 | a | 5'-GCUACUGUUCGUCGUCCCCCCCCCCCCCCCCCCCCCCCCCCCCCCCCCCC-3' | 50 |
| 135 | | b | 5'-IIIIIIIIIIIIIIIIIIIIIIIIIIIIIIIIIIICGAUGACAAGCAGCA-3' | 50 |
| 136 | 71 | a | 5'-GAAGUCAGUAGUCUCCCCCCCCCCCCCCCCCCCCCCCCCCCCCCCCCCCC-3' | 50 |
| 137 | | b | 3'-IIIIIIIIIIIIIIIIIIIIIIIIIIIIIIIIIIICUUCAGUCAUCAGAG-5' | 50 |
| 138 | 72 | a | 5'-CACUGAGACUGAUGCCCCCCCCCCCCCCCCCCCCCCCCCCCCCCCCCCCC-3' | 50 |
| 139 | | b | 3'-IIIIIIIIIIIIIIIIIIIIIIIIIIIIIIIIIIIGUGACUCUGACUACG-5' | 50 |
| 140 | 73 | a | 5'-UACAGCAGUCAGUCUCCCCCCCCCCCCCCCCCCCCCCCCCCCCCCCCCCC-3' | 50 |
| 141 | | b | 3'-IIIIIIIIIIIIIIIIIIIIIIIIIIIIIIIIIIIAUGUCGUCAGUCAGA-5' | 50 |
| 142 | 74 | a | 5'-CGAUGACUGACUACGCCCCCCCCCCCCCCCCCCCCCCCCCCCCCCCCCCC-3' | 50 |
| 143 | | b | 5'-IIIIIIIIIIIIIIIIIIIIIIIIIIIIIIIIIIIGCUACUGACUGAUGC-3' | 50 |
| 144 | 75 | a | 5'-CCCCGGCCGCCGCCCCCCCCCCCCCCCCCCCCCCCCCCCCCCCCCCCCCC-3' | 50 |
| 145 | | b | 5'-IGICIICIGCCIGIGIIIIIIIIIIIIIIIIIIIIIIIIIIIIIIIIIII-3' | 50 |
| 146 | 76 | a | 5'-GCCCCGCCCCGCCCCCCCCCCCCCCCCCCCCCCCCCCCCCCCCCCCCCCC-3' | 50 |
| 147 | | b | 5'-IIGICGIGICGIGICIIIIIIIIIIIIIIIIIIIIIIIIIIIIIIIIIII-3' | 50 |

TABLE 2-continued

| SEQ ID NO. | Compound No. | | Sequence | Length |
|---|---|---|---|---|
| 148 | 77 | a | 5'-CACUGCUCAUUCACACCCCCCCCCCCCCCCCCCCCCCCCCCCCCCCC-3' | 50 |
| 149 | | b | 3'-IIIIIIIIIG₁IIIIIIIIIG₁IIIIIIIIIG₁IIIIIGUGACGAGUAAGUGU-5' | 50 |
| 150 | 78 | a. | 5'-UACAGCAGUCAGUCUCCCCCCCCCCCCCCCCCGCCCCCCCCCCCCCCC-3' | 50 |
| 151 | | b. | 5'-IIIIIG₁IIIIIIIIIG₁IIIIIIIIIG₁IIIIIIIIIAUGUCAGUCAGA-3' | 50 |
| 152 | 79 | a. | 5'-CGAUGACUGACUACGCCCCCCCCCCCCCCCCCCCCCCCCCCCCCCCC-3' | 50 |
| 153 | | b. | 5'-IIIIIIIIG₁IIIIIIIIIG₁IIIIIIIIIG₁IIIIIIIGCUACUGACUGAUGC-3' | 50 |
| 154 | 80 | a. | 5'-CACUGAGACUGAUGCCCCCCCCCCCCCCCCCCCCCCCCCCCCCCCCC-3' | 50 |
| 155 | | b. | 5'-IIIIIG₁IIIIIIIIIG₁IIIIIIIIIG₁IIIIIIIIGUGACUCUGACUACG-3' | 50 |
| 156 | 81 | a. | 5'-CAAGGCAAGCAUUCGCCCCCCCCCCCCCCCCCCCCCCCCCCCCCCCC-3' | 50 |
| 157 | | b. | 5'-IIIIIIIIG₁IIIIIIIIG₁IIIIIIIIG₁IIIIIIIIGUUCCGUUCGUAAGC-3' | 50 |
| 158 | 82 | a | 5'-CACUGCUCAUUCACACCCCCCCCCC₃CCCCCCCCCC₃CCCCCCCCCC₃CCCCC-3' | 50 |
| 159 | | b | 3'-IIIIIIIIIGIIIIIIIIIGIIIIIIIIIGIIIIIGUGACGAGUAAGUGU-5' | 50 |
| 160 | 83 | a | 5'-UACAGCAGUCAGUCUCCCCCC₃CCCCCCCCCC₃CCCCCCCCCC₃CCCCCCCCC-3' | 50 |
| 161 | | b | 3'-IIIIIIIIIIIIIIIIIIIIIIIIIIIIIIIIIIIIIAUGUCGUCAGUCAGA-5' | 50 |
| 162 | 84 | a | 5'-CGAUGACUGACUACGCCCCCCCCC₃CCCCCCCCC₃CCCCCCCCC₃CCCCCCCC-3' | 50 |
| 163 | | b | 5'-IIIIIIIIIIIIIIIIIIIIIIIIIIIIIIIIIIIIIIIGCUACUGACUGAUGC-3' | 50 |
| 164 | 85 | a | 5'-CACUGAGACUGAUGCCCCCCC₃CCCCCCCCCC₃CCCCCCCCCC₃CCCCCCCC-3' | 50 |
| 165 | | b | 3'-IIIIIIIIIIIIIIIIIIIIIIIIIIIIIIIIIIIIIIGUGACUCUGACUACG-5' | 50 |
| 166 | 86 | a | 5'-CAAGGCAAGCAUUCGCCCCCCCCC₃CCCCCCCCC₃CCCCCCCCC₃CCCCCCCC-3' | 50 |
| 167 | | b | 3'-IIIIIIIIIIIIIIIIIIIIIIIIIIIIIIIIIIIIIIGUUCCGUUCGUAAGC-5' | 50 |
| 168 | 87 | a | 5-CACUGGCAGUUGACACCCCCC₃CCCCCC₃CCCCC₃CCCCCC₃CCCCC₃CCCCC-3' | 50 |
| 169 | | b | 3'-IIIIIIIIIIIIIIIIIIIIIIIIIIIIIIIIIIIIII GUGACCGUCAACUGU-5' | 50 |
| 170 | 88 | a | 5'-CACUGGCAGUUGACACCCCCCCCCCCCCCCCCCCCCCCCCCCCCCCCCCC-3' | 50 |
| 171 | | b | 3'-IIIIIIIIIIIIIIIIIIIIIIIIIIIIIIIIIIIII GUGACCGUCAACUGU-5' | 50 |
| 172 | 89 | a | 5'-CACUGGCAGUUGACACCCCCCCCCCCCCCCCCCCCCCCCCCCCCCCCCC-3' | 50 |
| 173 | | b | 3'-IIIIIIIIIIIIIIIIIIIIIIIIIIIIIIIIIIIIII GUGACCGUCAACUGU-5' | 50 |
| 174 | 90 | a | 5'-GUCCUCAGCGAUAGCCCCCCCCCCCCCCCCCCCCCCCCCCCCCCCCC-3' | 50 |
| 175 | | b | 3'-IIIIIIIIIIIIIIIIIIIIIIIIIIIIIIIIIIIII CAGGAGUCGCUAUCG-5' | 50 |
| 176 | 91 | a | 5'-CAUCGCUCCUCUCCACCCCCCCCCCCCCCCCCCCCCCCCCCCCCCCC-3' | 50 |
| 177 | | b | 5'-IIIIIIIIIIIIIIIIIIIIIIIIIIIIIIIIIIIII GUAGCGAGGAGAGGU-3' | 50 |
| 178 | 92 | a | 5'-CUCUACCGUUCGCUCCCCCCCCCCCCCCCCCCCCCCCCCCCCCCCCC-3' | 50 |
| 179 | | b | 5'-IIIIIIIIIIIIIIIIIIIIIIIIIIIIIIIIIIIIIGAGAUGGCAAGCGAG-3' | 50 |
| 180 | 93 | a | 5'-CACUGGCAGUUGACA-HEG-CCCCCCCCCCCCCCCCCCCCCCCCCCCC-3' | 50 |
| 181 | | b | 5'-IIIIIIIIIIIIIIIIIIIIIIIIIIIIIIIIIII-HEG-GUGACCGUCAACUGU-3' | 50 |
| 182 | 94 | a | 5'-CACUGGCAGUUGACA-HEG-CCCCCCCCCC-HEG-CCCCCCCCCC-HEG-CCCCCCCCCCCCC-3' | 50 |
| 183 | | b | 5'-IIIIIIIIII-HEG-IIIIIIIIII-HEG-IIIIIIIIIIIIIIGUGACCGUCAACUGU-3' | 50 |
| 184 | 95 | a | 5'-CACUGGCAGUUGACACCCCCCCCCCCCCCCCCCCCCCCCCCCCCCCCC-3' | 50 |
| 185 | | b | 3'-IIIIIIIIIIIIIIIIIIIIIIIIIIIIIIIIIIIIIIGUGACCGUCAACUGU-5' | 50 |
| 186 | 96 | a | 5'-CACUGGCAGUUGACACCCCCCCCCCCCCCCCCCCCCCCCCCCCCCCCC-3' | 50 |
| 187 | | b | 3'-IIIIIIIIIIIIIIIIIIIIIIIIIIIIIIIIIIIIIIGUGACCGUCAACUGU-5' | 50 |
| 188 | 97 | a | 5'-CACUGGCAGUUGACACCCCCCCCCCCCCCCCCCCCCCCCCCCCCCCCC-3' | 50 |
| 189 | | b | 3'-IIIIIIIIIIIIIIIIIIIIIIIIIIIIIIIIIIIIIIGUGACCGUCAACUGU-5' | 50 |
| 190 | 98 | a | 5'-CACUGGCAGUUGACACCCCCCCCCCCCCCCCCCCCCCCCCCCCCCCCC-3' | 50 |
| 191 | | b | 3'-IIIIIIIIIIIIIIIIIIIIIIIIIIIIIIIIIIIIIIGUGACCGUCAACUGU-5' | 50 |
| 192 | 99 | a | 5'-CACUGGCAGUUGACACCCCCCCCCCCCCCCCCCCCCCCCCCCCCCCCC-3' | 50 |
| 193 | | b | 3'-IIIIIIIIIIIIIIIIIIIIIIIIIIIIIIIIIIIIIIGUGACCGUCAACUGU-5' | 50 |
| 194 | 100 | a | 5'-CACUGGCAGUUGACACCCCCCCCCCCCCCCCCCCCCCCCCCCCCCCCC-3' | 50 |
| 195 | | b | 3'-IIIIIIIIIIIIIIIIIIIIIIIIIIIIIIIIIIIIIIGUGACCGUCAACUGU-5' | 50 |
| 196 | 101 | a | 5'-CACUGGCAGUUGACACCCCCCCCCCCCCCCCCCCCCCCCCCCCCCCCC-3' | 50 |
| 197 | | b | 3'-IIIIIIIIIIIIIIIIIIIIIIIIIIIIIIIIIIIIIIGUGACCGUCAACUGU-5' | 50 |

TABLE 2-continued

| SEQ ID NO. | Compound No. | | Sequence | Length |
|---|---|---|---|---|
| 198 | 102 | a | 5'-CACUGGCAGUUGACACCCCCCCCCCCCCCCCCCCCCCCCCCCCCCCCCC-3' | 50 |
| 199 | | b | 3'-IIIIIIIIIIIIIIIIIIIIIIIIIIIIIIIIIIIIIIGUGACCGUCAACUGU-5' | 50 |
| 200 | 103 | a | 5'-CACUGGCAGUUGACACCCCCCCCCCCCCCCCCCCCCCCCCCCCCCCCCC-3' | 50 |
| 201 | | b | 3'-IIIIIIIIIIIIIIIIIIIIIIIIIIIIIIIIIIIIIIGUGACCGUCAACUGU-5' | 50 |
| 202 | 104 | a | 5'-CACUGGCAGUUGACACCCCCCCCCCCCCCCCCCCCCCCCCCCCCCCCCC-3' | 50 |
| 203 | | b | 3'-IIIIIIIIIIIIIIIIIIIIIIIIIIIIIIIIIIIIIIGUGACCGUCAACUGU-5' | 50 |
| 204 | 105 | a | 5'-CACUGGCAGUUGACACCCCCCCCCCCCCCCCCCCCCCCCCCCCCCCCCC-3' | 50 |
| 205 | | b | 3'-IIIIIIIIIIIIIIIIIIIIIIIIIIIIIIIIIIIIIIGUGACCGUCAACUGU-5' | 50 |
| 206 | 106 | a | 5'-CACUGGCAGUUGACACCCCCCCCCCCCCCCCCCCCCCCCCCCCCCCCCC-3' | 50 |
| 207 | | b | 3'-IIIIIIIIIIIIIIIIIIIIIIIIIIIIIIIIIIIIIIIIGUGACCGUCAACUGU-5' | 50 |
| 208 | 107 | a | 5'-CACUGGCAGUUGACACCCCCCCCCCCCCCCCCCCCCCCCCCCCCCCCCC-3' | 50 |
| 209 | | b | 3'-IIIIIIIIIIIIIIIIIIIIIIIIIIIIIIIIIIIIIIGUGACCGUCAACUGU-5' | 50 |
| 210 | 108 | a | 5'-CACUGGCAGUUGACACCCCCCCCCCCCCCCCCCCCCCCCCCCCCCCCCC-3' | 50 |
| 211 | | b | 3'-IIIIIIIIIIIIIIIIIIIIIIIIIIIIIIIIIIIIIIIIGUGACCGUCAACUGU-5' | 50 |
| 212 | 109 | a | 5'-CACUGGCAGUUGACACCCCCCCCCCCCCCCCCCCCCCCCCCCCCCCCCCC-3' | 50 |
| 213 | | b | 3'-IIIIIIIIIIIIIIIIIIIIIIIIIIIIIIIIIIIIIIIIGUGACCGUCAACUGU-5' | 50 |
| 214 | 110 | a | 5'-CACUGGCAGUUGACACCCCCCCCCCCCCCCCCCCCCCCCCCCCCCCCCC-3' | 50 |
| 215 | | b | 3'-IIIIIIIIIIIIIIIIIIIIIIIIIIIIIIIIIIIIIIGUGACCGUCAACUGU-5' | 50 |
| 216 | 111 | a | 5'-CACUGGCAGUUGACACCCCCCCCCCCCCCCCCCCCCCCCCCCCCCCCCC-3' | 50 |
| 217 | | b | 3'-IIIIIIIIIIIIIIIIIIIIIIIIIIIIIIIIIIIIIIIIGUGACCGUCAACUGU-5' | 50 |
| 218 | 112 | a | 5'-CACUGGCAGUUGACACCCCCCCCCCCCCCCCCCCCCCCCCCCCCCCCCCC-3' | 50 |
| 219 | | b | 3'-IIIIIIIIIIIIIIIIIIIIIIIIIIIIIIIIIIIIIIIIIGUGACCGUCAACUGU-5' | 50 |
| 220 | 113 | a | 5'-CACUGGCAGUUGACACCCCCCCCCCCCCCCCCCCCCCCCCCCCCCCCCCC-3' | 50 |
| 221 | | b | 3'-IIIIIIIIIIIIIIIIIIIIIIIIIIIIIIIIIIIIIIGUGACCGUCAACUGU-5' | 50 |
| 222 | 114 | a | 5'-CACUGGCAGUUGACACCCCCCCCCCCCCCCCCCCCCCCCCCCCCCCCCC-3' | 50 |
| 223 | | b | 3'-IIIIIIIIIIIIIIIIIIIIIIIIIIIIIIIIIIIIIIIIIIGUGACCGUCAACUGU-5' | 50 |
| 224 | 115 | a | 5'-CCCCCCCCCCCCCCCCCCCCCCCCCCCCCCCCCCCCCCACUGGCAGUUGACA-3' | 50 |
| 225 | | b | 5'-IIIIIIIIIIIIIIIIIIIIIIIIIIIIIIIIIIIIIIUGUCAACUGCCAGUG-3' | 50 |
| 226 | 116 | a | 3'-CCCCCCCCCCCCCCCCCACAGUUGACGGUCACCCCCCCCCCCCCCCCCCC-5' | 50 |
| 227 | | b | 3'-IIIIIIIIIIIIIIITIIIIIIIIIIIIIIIIIIIIIIGUGACCGUCAACUGU-5' | 50 |
| 228 | 117 | a | 5'-CACUGGCAGUUGACAUUUUUUUUUUUUUUUUUUUUUUUUUUUUUUUUUU-3' | 50 |
| 229 | | b | 3'-IIIIIIIIIIIIIIIIIIIIIIIIIIIIIIIIIIIIIIGUGACCGUCAACUGU-5' | 50 |
| 230 | 118 | a | 5'-CACUGGCAGUUGACAAAAAAAAAAAAAAAAAAAAAAAAAAAAAAAAAAA-3' | 50 |
| 231 | | b | 3'-IIIIIIIIIIIIIIIIIIIIIIIIIIIIIIIIIIIIIIGUGACCGUCAACUGU-5' | 50 |
| 232 | 119 | a | 5'-ACACCCCCC-3' | 10 |
| 233 | | b | 3'-IIIIIIIUGU-5' | 10 |
| 234 | 120 | a | 5'-ACACCCCCCCCCCCCCCCC-3' | 20 |
| 235 | | b | 3-IIIIIIIIIIIIIIIIIUGU-5' | 20 |
| 236 | 121 | a | 5'-CCCCCCCCCCCCCCCCCCCCCCCCCCCCCCCCCCCCCCCCCCCCCCCCCC-3' | 50 |
| 237 | | b | 3'-IIIIIIIIIIIIIIIIIIIIIIIIIIIIIIIIIIIIIIIIIIIIIIIIII-5 | 50 |
| 238 | 122 | a | 5'-CACUGCCCCCCCCCCCCCCCCCCCCCCCCCCCCCCCCCCCCCCCCCCCC-3' | 50 |
| 239 | | b | 3'-IIIIIIIIIIIIIIIIIIIIIIIIIIIIIIIIIIIIIIIIIIIIIGUGAC-5' | 50 |
| 240 | 123 | a | 5'-CACUGGCAGUCCCCCCCCCCCCCCCCCCCCCCCCCCCCCCCCCCCCCCCC-3' | 50 |
| 241 | | b | 3'-IIIIIIIIIIIIIIIIIIIIIIIIIIIIIIIIIIIIIIIIIGUGACCGUCA-5' | 50 |
| 242 | 124 | a | 5'-CACUGGCAGUUGACACAGGUUCCUCACUUCACAAAUCGUUCAUCGUUCAC-3' | 50 |
| 243 | | b | 3'-GUGACCGUCAACUGUGUCCAAGGAGUGAAGUGUUUAGCAAGUAGCAAGUG-5' | 50 |

TABLE 2-continued

| SEQ ID NO. | Compound No. | | Sequence | Length |
|---|---|---|---|---|
| 244 | 125 | a | 5'-CAAUGGCACUUAACACCCCCCCCCCCCCCCCCCCCCCCCCCCCCCCC-3' | 50 |
| 245 | | b | 3'-IIIIIIIIIIIIIIIIIIIIIIIIIIIIIIIIIIIIGUGACCGUCAACUGU-5' | 50 |

I = inosine;
X = glycerol;
Y = 1,3-propanediol;
$C_1$ = ara-C;
$C_2$ = 5-Me-C;
$C_3$ = 5-methyl-cytidine;
$G_1$ = 7-deaza-G;
$G_2$ = ara-G;
bold = phosphorothioate linkage;
underscore = 2'-methoxy-nucleoside;
HEG = hexaethylene glycol.

Additional structures that may be formed by the TLR3 agonists of the invention include Formulas XI, XII and XIII.

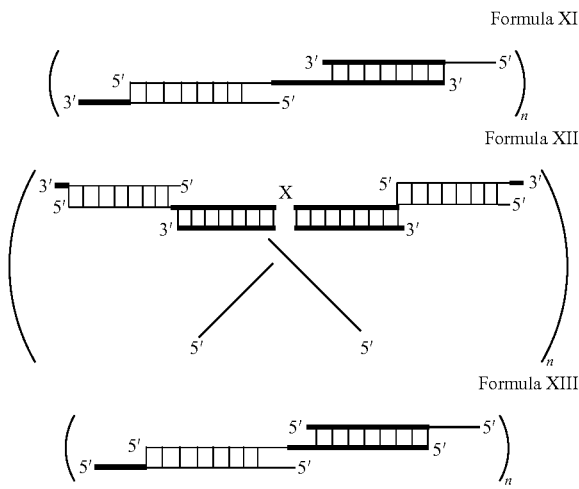

In any of the methods according to the invention, a therapeutically or prophylactically effective amount of a TLR3 agonist of the invention and effective in stimulating TLR3 activity is administered to a cell. This cell may be part of a cell culture, a neovascularized tissue culture, or may be part or the whole body of a mammal such as a human or other mammal. Administration of the therapeutic compositions of TLR3 agonist can be carried out using known procedures at dosages and for periods of time effective to reduce symptoms or surrogate markers of the disease, depending on the condition and response, as determined by those with skill in the art. It may be desirable to administer simultaneously, or sequentially a therapeutically effective amount of one or more of the therapeutic TLR3 agonists of the invention to an individual as a single treatment episode. In some exemplary embodiments of the methods of the invention described above, the TLR3 agonist is administered locally and/or systemically. The term "administered locally" refers to delivery to a defined area or region of the body, while the term "systemic administration" is meant to encompass delivery to the whole organism.

In any of the methods according to the invention, one or more of the TLR3 agonists or composition thereof can be administered alone or in combination with any other agent useful for treating the disease or condition that does not diminish the immunostimulatory effect of the TLR3 agonists. In any of the methods according to the invention, the agent useful for treating the disease or condition includes, but is not limited to, one or more vaccines, antigens, antibodies, cytotoxic agents, allergens, antibiotics, antisense oligonucleotides, TLR agonist, TLR antagonist, siRNA, miRNA, peptides, proteins, gene therapy vectors, DNA vaccines, adjuvants or kinase inhibitors to enhance the specificity or magnitude of the immune response, or co-stimulatory molecules such as cytokines, chemokines, protein ligands, trans-activating factors, peptides and peptides comprising modified amino acids. For example, in the treatment of cancer, it is contemplated that the TLR3 agonist or composition thereof according to the invention may be administered in combination with one or more targeted therapeutic agents and/or monoclonal antibodies. Alternatively, the agent can include DNA vectors encoding for antigen or allergen. In these embodiments, the TLR3 agonist of the invention can produce direct immunostimulatory effects. When co-administered with one or more other therapies, the TLR3 agonist of the invention may be administered either simultaneously with the other treatment(s), or sequentially.

In the various methods according to the invention the route of administration may be by any suitable route including, without limitation, parenteral, mucosal delivery, oral, sublingual, transdermal, topical, inhalation, intranasal, aerosol, intraocular, intratracheal, intrarectal, vaginal, by gene gun, dermal patch or in eye drop or mouthwash form.

When a therapeutically effective amount of TLR3 agonist of the invention is administered orally, the TLR3 agonist will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% synthetic oligonucleotide and preferably from about 25 to 90% synthetic oligonucleotide. When administered in liquid form, a liquid carrier such as water, petroleum, oils of animal or plant origin such as peanut oil, mineral oil, soybean oil, sesame oil, or synthetic oils may be added. The liquid form of the pharmaceutical composition may further contain physiological saline solution, dextrose or other saccharide solution or glycols such as ethylene glycol, propylene glycol or polyethylene glycol. When administered in liquid form, the pharmaceutical composition contains from about 0.5 to 90% by weight of the synthetic oligonucleotide or from about 1 to 50% synthetic oligonucleotide.

When a therapeutically effective amount of TLR3 agonist of the invention is administered by parenteral, mucosal delivery, oral, sublingual, transdermal, topical, inhalation, intranasal, aerosol, intraocular, intratracheal, intrarectal, vaginal, by gene gun, dermal patch or in eye drop or mouthwash form, the TLR3 agonist will be in the form of a pyrogen-free, parenterally acceptable aqueous solution. The preparation of such parenterally acceptable solutions, having due regard to pH, isotonicity, stability, and the like, is within the skill in the art. A pharmaceutical composition for parenteral, mucosal delivery, oral, sublingual, transdermal, topical, inhalation, intranasal, aerosol, intraocular, intratracheal, intrarectal, vaginal, by gene gun, dermal patch or in eye drop or mouthwash form should contain, in addition to the TLR3 agonist, an isotonic vehicle such as Sodium Chloride Injection, Ringer's Injection, Dextrose Injection, Dextrose and Sodium Chloride Injection, Lactated Ringer's Injection or other vehicle as known in the art. The pharmaceutical composition of the present invention may also contain stabilizers, preservatives, buffers, antioxidants or other additives known to those of skill in the art.

When administered parenteral, mucosal delivery, oral, sublingual, transdermal, topical, inhalation, intranasal, aerosol, intraocular, intratracheal, intrarectal, vaginal, by gene gun, dermal patch or in eye drop or mouthwash form, doses ranging from 0.01% to 10% (weight/volume) may be used. When administered in liquid form, a liquid carrier such as water, petroleum, oils of animal or plant origin such as peanut oil, mineral oil, soybean oil, sesame oil or synthetic oils may be added. Topical administration may be by liposome or transdermal time-release patch.

The amount of TLR3 agonist in the pharmaceutical composition of the present invention will depend upon the nature and severity of the condition being treated, and on the nature of prior treatments that the patent has undergone. It is contemplated that the various pharmaceutical compositions used to practice the method of the present invention should contain about 10 micrograms to about 20 mg of synthetic oligonucleotide per kg body or organ weight.

The duration of intravenous therapy using the pharmaceutical composition of the present invention will vary, depending on the severity of the disease being treated and the condition and potential idiosyncratic response of each individual patient.

Some diseases lend themselves to acute treatment while others require longer-term therapy. Both acute and long-term intervention in diseases are worthy goals. Injections of TLR3 agonists can be an effective means of inhibiting certain diseases in an acute situation. However for long-term therapy over a period of weeks, months or years, systemic delivery (intraperitoneal, intramuscular, subcutaneous, intravenous) either with carriers such as saline, slow release polymers or liposomes are likely to be considered.

In some chronic diseases, systemic administration of TLR3 agonists of the invention may be preferable. The frequency of injections is from continuous infusion to once a month, several times per month or less frequently will be determined based on the disease process and the biological half-life of the TLR3 agonist.

The TLR3 agonists and methods of the invention are also useful for examining the function of TLR3 in a cell or in a control mammal or in a mammal afflicted with a disease associated with TLR3 or immune stimulation through TLR3. In such use, the cell or mammal is administered the TLR3 agonists, and the activity of TLR3 is examined.

Without being limited to any theory or mechanism, it is generally believed that the activity of TLR3 agonists according to the invention depends on the binding of the TLR3 agonist to TLR3, thus stimulating the activity of TLR3. Such stimulation under physiological conditions is measured as a practical matter by observing the down-stream activity of TLR3. Thus, an exemplary TLR3 agonist used in accordance with the invention is capable of forming a stable bond with TLR3; activating TLR3 and initiating a cascade of activity through various signaling molecules.

The following examples illustrate the exemplary modes of making and practicing the present invention, but are not meant to limit the scope of the invention since alternative methods may be utilized to obtain similar results.

Example 1

Synthesis of TLR3-Agonists

The immune modulatory oligoribonucleotides were chemically synthesized using phosphoramidite chemistry on automated DNA/RNA synthesizer. TAC protected (Except U) 2'-O-TBDMS RNA monomers, A, G, C and U, were purchased from Sigma-Aldrich. 7-deaza-G, inosine, and loxoribine monomers were purchased from ChemGenes Corporation. 0.25M 5-ethylthio-1H-tetrazole, PAC-anhydride Cap A and Cap B were purchased from Glen Research. 3% trichloroacetic acid (TCA) in dichloromethane (DCM) and 5% 3H-1,2-Benzodithiole-3-one-1,1-dioxide (Beaucage reagent) were made in house.

Immune modulatory oligoribonucleotides were synthesized at 1-2 μM scale using a standard RNA synthesis protocol.

Cleavage and Base Deprotection

Immune modulatory oligoribonucleotides were cleaved from solid support and the solution was further heated at 65° C. to removing protecting groups of exo cyclic-amines. The resulting solution was dried completely in a SpeedVac.

IE HPLC Purification

Immune modulatory oligoribonucleotides were purified by ion exchange HPLC.
Column: Dionex DNAPac 100 column (22×250)
Column Heater ChromTech TL-105 HPLC column heater, temperature is set to 80° C.
Buffer A: 20 mM Tris-HCl, pH 7.0, 20% acetinitrile
Buffer B: 3.0 M NaCl, 20 mM Tris-HCl, pH 7.0, 20% acetonitrile
Flow rate: 10 ml/min
Gradient:
   0-2 min: 0% B
   2-11 min: 0% B to 35% B
   11-41 min: 35% B to 90% B
   41-45 min: 100% B Crude immune modulatory oligoribonucleotide solution was injected into HPLC. Above gradient is performed and the fractions were collected. All fractions containing more than 90% desired product were mixed, and then the solution was concentrated to almost dry by RotoVap. RNAse-free water was added to make final volume of 10 ml.

C-18 Reversed Phase Desalting

CC-18 Sep-Pak cartridge purchased from Waters was first conditioned with 10 ml of acetonitrile followed by 10 ml of 0.5 M sodium acetate. 10 ml of immune modulatory oligoribonucleotide solution was loaded. 15 ml of water was then used to wash out the salt. The immune modulatory oligoribonucleotide was finally eluted out by 1 ml of 50% acetonitrile in water.

The solution is placed in SpeedVac for 30 minutes. The remaining solution was filter through a 0.2 micro filter and then was lyophilized to dryness. The solid was then re-dissolved in water to make the desired concentration. The final solution was stored below 0° C.
Capillary Electrophoresis
Instrument: Beckman 5010
Capillary: 62 cm ssDNA capillary
Sample preparation: 0.2 OD of SIMRA compound was dissolved in 200 ul of RNAse-free water.
Injection: electro-kinetic injection at 5 KV for 5 seconds.
Running condition: 14 KV for 50 minutes at 30° C.
Ion Exchange HPLC Analysis
Column: Dionex DNAPac guard column (22×250)
Column Heater ChromTech TL-105 HPLC column heater, temperature is set to 80° C.
Buffer A: 100 mM Tris-HCl, pH 8.0, 20% acetinitrile
Buffer B: 2.0 M LiCl, 100 mM Tris-HCl, pH 8.0, 20% acetonitrile
Flow rate: 2 ml/min
Gradient:
0-2 min: 0% B
2-10 min: 0% B to 100% B
10-15 min: 100% B
PAGE Analysis
0.3 OD of immune modulatory oligoribonucleotide was loaded on 20% polyacrylamide gel and was running at constant power of 4 watts for approximately 5 hours. The gel was viewed under short wavelength UV light.

Example 2

HEK293 Cell Cultures

HEK293 cells stably expressing human TLR3 and pNifty-2 plasmid containing the SEAP reporter gene were purchased from Invivogen. Cells were maintained in Dulbecco's modified Eagle's medium with 10% fetal bovine serum (FBS) and 10 µg/ml blasticidin and 100 U/ml penicillin and streptomycin.

For transient transfection assay, cells were trypsinized and plated overnight in DMEM with FBS (no antibiotics) in 48 well plates. Next day, aliquots of 25 µl of the plasmid DNA/lipofectamine2000 mixture containing 100 ng of plasmid DNA and 1 µl of lipofectamine were added to each well of the cell culture plate. TLR3 agonist compounds were added to the cultures, and the cultures were continued for 18 h. At the end of the treatment, 20 µl of culture supernatant was taken from each treatment and used for SEAP assay following manufacturer's protocol (Invivogen).
SEAP Assay:

SEAP activity was quantified using the Quanti Blue Detection substrate (Invivogen) according to the manufacturer's instructions. To 20 µl of culture supernatant in a 96 well plate, 150 µl of SEAP Detection substrate was added. The samples were assayed in duplicate. The plates were incubated at 37° C. for 30-40 minutes and read at 620-655 nm. The results are expressed as % maximal (agonist) NF-κB activity.
J774 Cell Assay:

Murine J774 macrophage cells (BIM-67, ATCC) were maintained in Dulbecco's modified Eagle's medium supplemented with 10% (v/v) FBS and antibiotics (100 U/ml of penicillin and streptomycin). For the experiments, cells were plated at a density of $7 \times 10^5$ cells/ml in 48-well plates and allowed to attach overnight. Next day the cells were treated with agonist for 18 h and then supernatants were collected for measurement of cytokine production by ELISA (IL-6, IL-12, IFNβ), according to manufacturer's instructions (BD Biosciences, PBL respectively).
Human PBMC and Myeloid DC Cultures:

Peripheral blood mononuclear cells (PBMCs) from freshly drawn healthy volunteer blood (Research Blood Components, Brighton, Mass.) were isolated by Ficoll density gradient centrifugation method (Ficoll-Paque PLUS, GE Health Care).

Human CD1c (BDCA-1)$^+$ myeloid dendritic cells were isolated from PBMCs by two magnetic separation steps involving depletion of CD19$^+$ B cells and positive selection of CD1c (BDCA-1)$^+$ cells (Miltenyi Biotec, Auburn, Calif.) according to the manufacturer's instructions.

The culture medium used for the assay consisted of RPMI 1640 medium supplemented with 1.5 mM glutamine, 1 mM sodium pyruvate, 0.1 mM non-essential amino acids, 50 µM 2-mercaptoethanol, 100 IU/ml penicillin-streptomycin mix and 10% heat-inactivated fetal bovine serum (Hyclone).
Cytokine Measurements:

PBMCs ($5 \times 10^6$ cells/ml) and mDCS ($1 \times 10^6$ cells/ml) were cultured in 96 well flat bottom plates then stimulated with agonist for a period of 24 h. Unstimulated cells served as controls.

At the end of the incubation period supernatants were harvested and stored frozen until the time of assay by Luminex multiplex technology. A 25-plex human cytokine bead kit (Invitrogen) was used according to the manufacturer's instructions. Results from cells treated according to Example 2 are shown in FIG. 2A, 2B, 4, 5, 6, 7, 10 or 11, and Tables 3, 4, 5A, 5B, 5C, 5D, 6, 7, 8, 9, 10, 11, 12 or 13.

TABLE 3

| Com- | Cytokine/Chemokine, pg/ml (+/−SD) | | | | |
|---|---|---|---|---|---|
| pound # | IL-1Ra | IL-8 | MIP-1β | IP-10 | MCP-1 |
| 27 | 667 (220) | 1034 (31) | 20 (4) | 595 (133) | 200 (4) |
| 29 | 269 (46) | 113 (7) | 5 (6) | 466 (81) | 39 (7) |
| 30 | 617 (14) | 106 (2) | 15 (2) | 713 (126) | 83 (6) |
| 31 | 131 (40) | 265 (17) | 17 (2) | 39 (7) | 17 (1) |
| PBS | 40 (16) | 127 (24) | 6 (4) | 11 (4) | 50 (65) |

At 250 µg/ml concentration of compounds.

TABLE 4

| Com- | Cytokine/Chemokine, pg/ml (+/−SD) | | | | | | |
|---|---|---|---|---|---|---|---|
| pound # | IL-1Ra | IL-6 | IL-8 | MIP-1α | MIP-1β | IP-10 | MCP-1 |
| 27 | 1057 (38) | 257 (6) | 21907 (526) | 299 (8) | 955 (7) | 2936 (79) | 7929 (698) |
| 29 | 1249 (40) | 113 (1) | 9618 (35) | 129 (4) | 521 (0) | 4568 (80) | 6548 (138) |
| 30 | 1058 (113) | 157 (12) | 12007 (388) | 123 (9) | 489 (14) | 2438 (185) | 3538 (210) |
| 31 | 544 (45) | 115 (5) | 17607 (575) | 48 (3) | 224 (5) | 326 (15) | 1189 (38) |
| PBS | 288 (0) | 42 (1) | 2875 (52) | 0 (0) | 79 (2) | 41 (0) | 68 (0) |

At 250 µg/ml concentration of compounds.

TABLE 5A

| Compound | Fold increase in NF-κB activity |
|---|---|
| Medium | 1.0 |
| 1 | 0.8 |
| 3 | 1.3 |
| 4 | 1.0 |
| 5 | 0.9 |
| 6 | 1.0 |
| 12 | 1.7 |
| 13 | 1.0 |
| 24 | 1.0 |

Concentration of compounds was 250 µg/mL. Data shown are representative of two independent experiments.

TABLE 5B

| Compound | Fold increase in NF-κB activity |
|---|---|
| Medium | 1.0 |
| 8 | 1.0 |
| 14 | 1.2 |
| 18 | 1.2 |
| 20 | 1.2 |
| 21 | 1.2 |
| 22 | 1.1 |
| 23 | 1.2 |

Concentration of compounds was 50 µg/mL. Data shown are representative of two independent experiments.

TABLE 5C

| Compound | Fold increase in NF-κB activity |
|---|---|
| Medium | 1.0 |
| 9 | 1.6 |
| 10 | 1.5 |
| 11 | 1.8 |

Concentration of compounds was 100 µg/mL. Data shown are representative of two independent experiments.

TABLE 5D

| Compound | Fold increase in NF-κB activity |
|---|---|
| M | 1.0 |
| 16 | 0.6 |

Concentration of compounds was 150 µg/mL. Data shown are representative of two independent experiments.

TABLE 6

| Compound # | Fold increase in NF-κB activity |
|---|---|
| Medium | 1.0 |
| 36 | 0.93 |
| 37 | 1.33 |
| 38 | 5.50 |
| 41 | 3.64 |
| 42 | 5.20 |

Concentration of compounds was 250 µg/mL. Data shown are representative of two independent experiments.

TABLE 7

| Compound # | IL-6 (pg/ml) | IL-12 (pg/ml) | IP-10 (pg/ml) | IFN-β (pg/ml) |
|---|---|---|---|---|
| Medium | 0 | 51.3 | 0 | 1.2 |
| 36 | 0 | 97.3 | 0 | 0 |
| 37 | 1004.7 | 313.1 | 16583 | 76.8 |
| 38 | 1114.1 | 223.5 | 20361 | 94.3 |
| 41 | 1271.3 | 352.9 | 17900 | 101.2 |
| 42 | 1359.5 | 315.4 | 19493 | 121.5 |

Concentration of compounds was 250 µg/mL. Data shown are representative of two independent experiments.

TABLE 8

| Compound # | IL-6 (pg/ml) | IL-12 (pg/ml) | IP-10 (pg/ml) | IFN-β (pg/ml) |
|---|---|---|---|---|
| Medium | 0 | 85.1 | 0 | 0 |
| 43 | 175.8 | 287.2 | 18724 | 36.5 |
| 44 | 137.0 | 145.8 | 13923 | 0 |
| 45 | 3313.4 | 3236.6 | 19175 | 1416.2 |
| 46 | 5672.4 | 8599.6 | 18398 | 446.5 |
| 47 | 9.44 | 114.2 | 9281.5 | 0 |
| 48 | 2 | 110.5 | 8187.5 | 0 |
| 49 | 11.9 | 118.8 | 157.3 | 0 |
| 50 | 135.4 | 153.9 | 14871 | 68.8 |

Concentration of compounds was 250 µg/mL. Data shown are representative of two independent experiments.

TABLE 9

| Compound# | IL-6 (pg/ml) | IL-12 (pg/ml) | IP-10 (pg/ml) | IFN-β (pg/ml) |
|---|---|---|---|---|
| Medium | 11.2 | 117.2 | 54.7 | 0 |
| 51 | 2432.7 | 1319.4 | 32923 | 533.5 |
| 52 | 1296.6 | 113.3 | 676833 | 7.9 |
| 53 | 32.0 | 133.8 | 12764 | 0 |
| 54 | 11.9 | 114.3 | 563.4 | 0 |
| 55 | 11.9 | 99.0 | 206.0 | 0 |
| 56 | 4177.5 | 1838.0 | 80034 | 1037.3 |
| 57 | 27.4 | 129.0 | 5424.3 | 0 |

Concentration of compounds was 250 µg/mL. Data shown are representative of two independent experiments.

TABLE 10

| Compound# | IL-6 (pg/ml) | IL-12 (pg/ml) | IP-10 (pg/ml) | IFN-β (pg/ml) |
|---|---|---|---|---|
| Medium | 22.3 | 149.2 | 109.4 | 0 |
| 61 | 22.3 | 137.8 | 249.1 | 3.59 |
| 62 | 966.2 | 294.4 | 21736 | 3.08 |
| 63 | 61.1 | 141.2 | 6239.7 | 0 |

Concentration of compounds was 250 µg/mL. Data shown are representative of two independent experiments.

TABLE 11

| Compound# | IL-6 (pg/ml) | IL-12 (pg/ml) | IP-10 (pg/ml) | IFN-β (pg/ml) |
|---|---|---|---|---|
| Medium | 22.3 | 149.2 | 109.4 | 0 |
| 64 | 18.9 | 119.1 | 179.8 | 0 |
| 65 | 32.1 | 14.5 | 0 | — |
| 66 | 233.7 | 168.2 | 14256.8 | 0 |
| 67 | 18.9 | 128.8 | 244.3 | 0 |
| 68 | 1379.4 | 171.4 | 33076.8 | 1.43 |

Concentration of compounds was 250 µg/mL. Data shown are representative of two independent experiments.

TABLE 12

| Compound# | IL-1Ra (pg/ml) | IL-12 (pg/ml) | IP-10 (pg/ml) | MCP-1 (pg/ml) |
|---|---|---|---|---|
| Medium | 8.0 | 0.6 | 3.8 | 3.2 |
| 36 | 79.6 | 26.8 | 16.9 | 19.8 |
| 37 | 343.0 | 32.7 | 51.8 | 1955.2 |
| 38 | 151.9 | 34.9 | 102.4 | 44.3 |
| 41 | 1440.3 | 45.1 | 1526.0 | 895.0 |
| 42 | 2482.8 | 125.2 | 150.6 | 34655 |

Concentration of compounds was 300 µg/mL. Data shown are representative of two independent experiments.

TABLE 13

| Compound# | IL-1Ra (pg/ml) | IL-6 (pg/ml) | IP-10 (pg/ml) | MCP-1 (pg/ml) |
|---|---|---|---|---|
| Medium | 91.5 | 10.6 | 0 | 0 |
| 36 | 58.8 | 17.3 | 23.7 | 27.0 |
| 37 | 344.2 | 18.7 | 458.7 | 321.6 |
| 38 | 1390.7 | 538.2 | 1291.6 | 7251.5 |
| 41 | 962.0 | 326.1 | 1001.2 | 8959.4 |
| 42 | 1237.1 | 367.3 | 2257.4 | 7263.4 |

Concentration of compounds was 300 µg/mL. Data shown are representative of two independent experiments.

Example 3

In Vivo Cytokine Secretion in Mouse Model Treated with TLR3 Agonist Compounds

Figure 8:
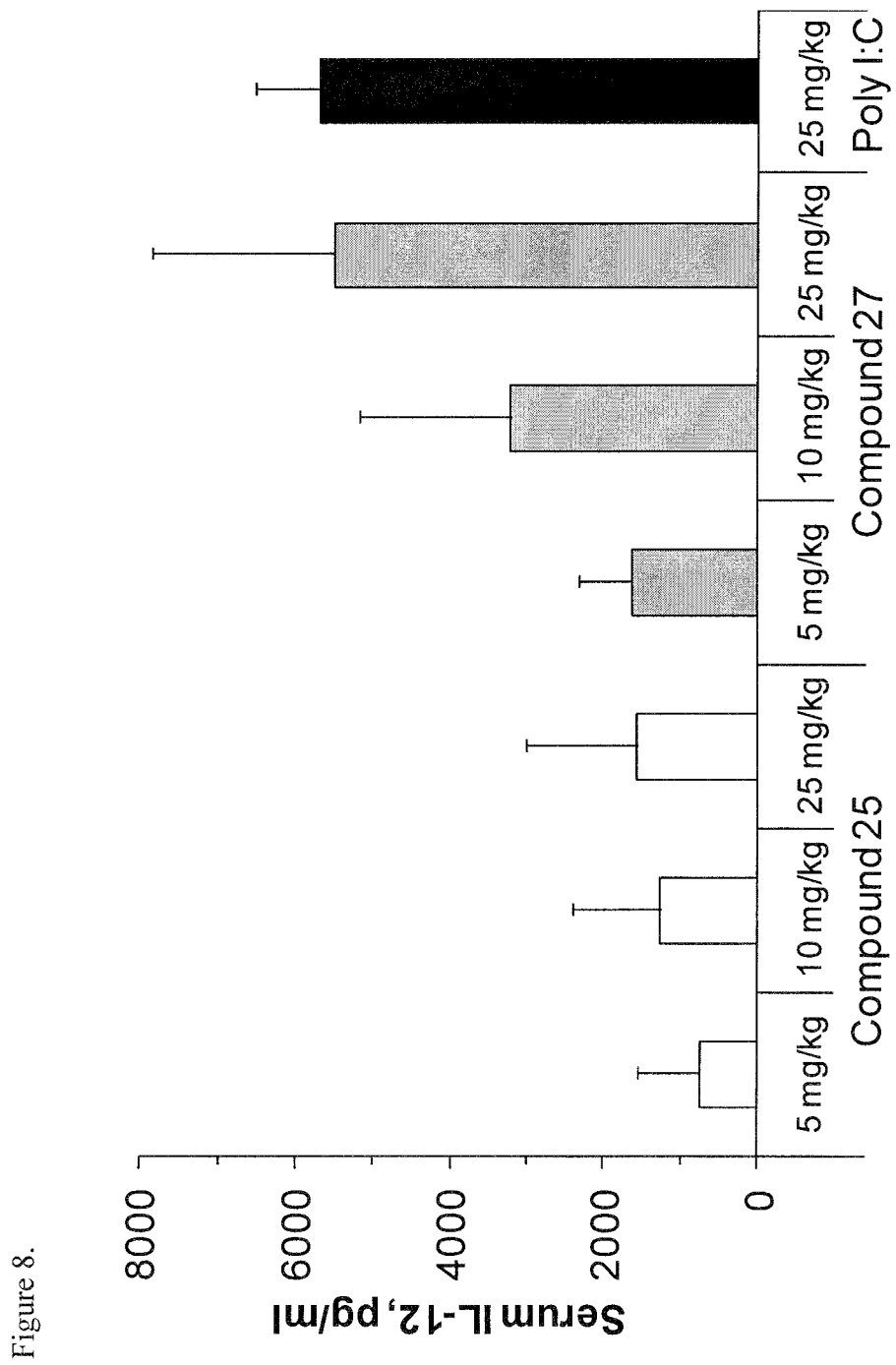
FIG. 8 and Table 14 depict serum cytokine induction in C57BL/6 mice (n=3) 2 hours after they were treated and analyzed according to Example 3. Briefly, the C57BL/6 mice were injected subcutaneously with 0 mg/kg or 25 mg/kg dose of TLR3 agonists, and 2 hours after administration of the agonist, serum was analyzed for immune stimulatory cytokine levels, and IL-12 levels are presented. The data demonstrate that in vivo administration of a TLR3 agonist of the invention generates a distinct TLR-mediated in vivo cytokine profile.
Figure 9:
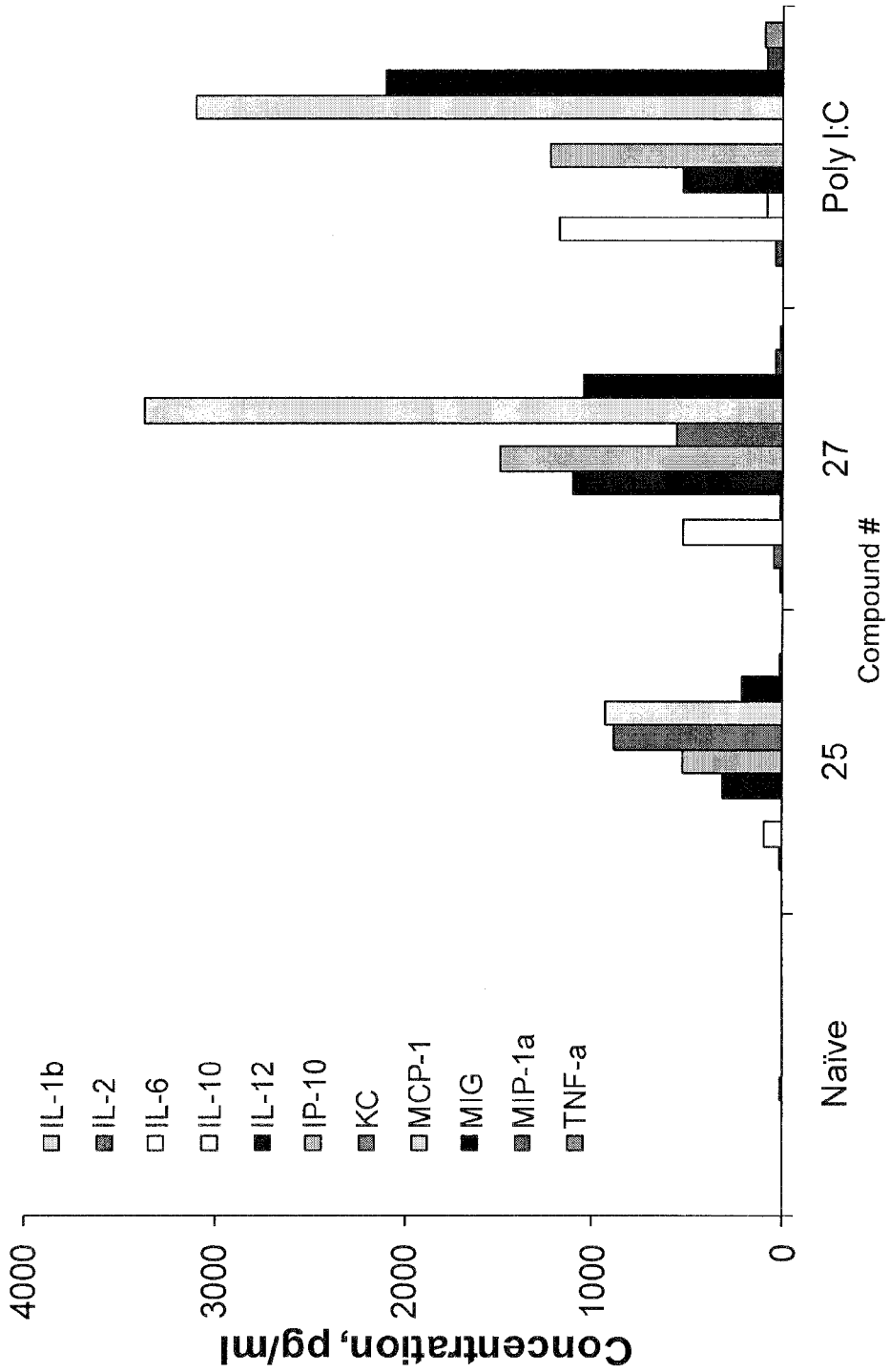
FIG. 9 is a graphical representation of serum cytokine induction in C57BL/6 mice (n=3) 2 hours after they were treated and analyzed according to Example 3. Briefly, the C57BL/6 mice were injected subcutaneously with 0 mg/kg or 25 mg/kg dose of TLR3 agonists, and 2 hours after administration of the agonist, serum was analyzed for cytokine and chemokine levels, and IL-1b, IL-2, IL-6, IL-10, IL-12, IP-10, KC, MCP-1, MIG, MIP-1α, TNFα levels are presented. The data demonstrate that in vivo administration of a TLR3 agonist of the invention generates a distinct TLR-mediated in vivo cytokine and chemokine profile.
Figure 10:
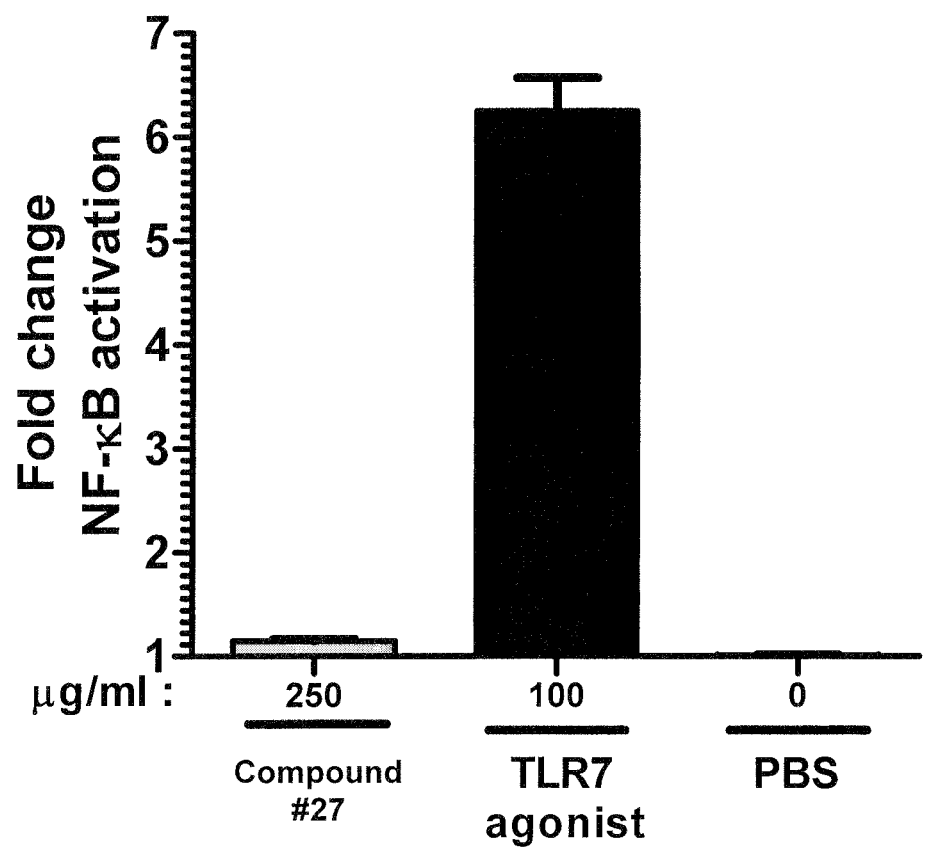
FIG. 10 is a graphical representation of immune stimulatory activity of exemplary TLR3 agonists according to the invention in HEK293 cells expressing human TLR7 that were treated and analyzed according to example 2. Briefly, the HEK293 cells were treated with TLR3 agonists of the invention for 18 hr, and the levels of NF-κB subsequently produced were determined using SEAP (secreted form of human embryonic alkaline phosphatase) assay. The data demonstrate the specificity of exemplary TLR3 agonists according to the invention as such compounds did not stimulate TLR7-mediated NF-κB, which is known to be a TLR that responds to single stranded RNA molecules. More generally these data demonstrate that TLR3 agonists of the invention induce a TLR3 specific immune response.
Figure 11:
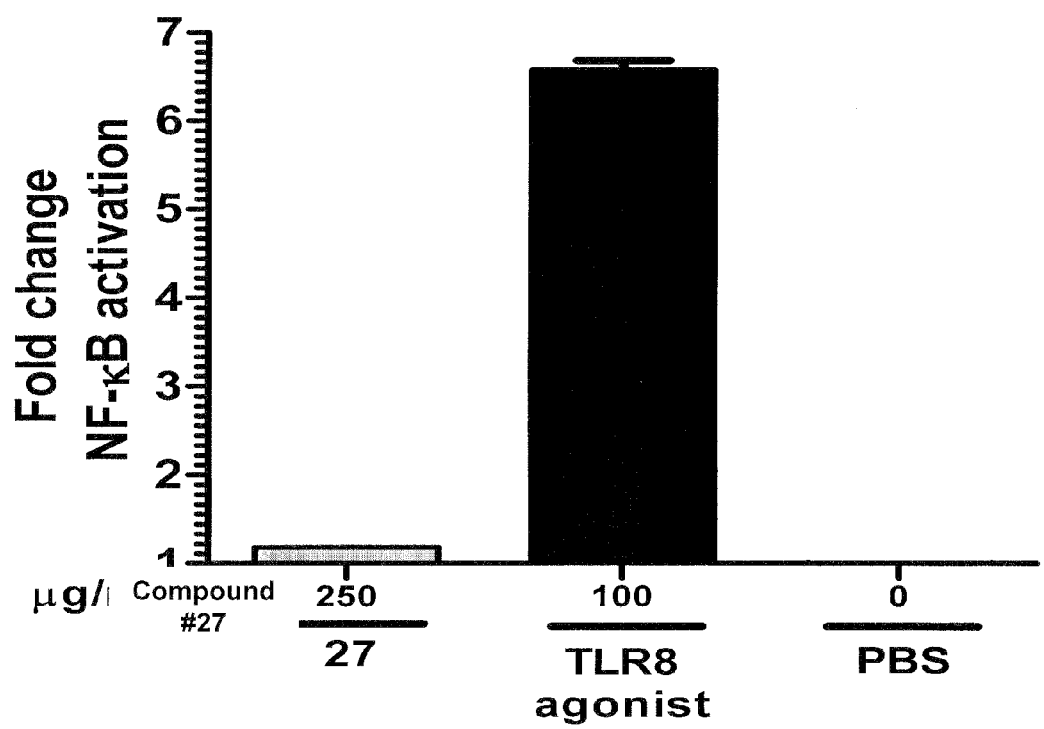
FIG. 11 is a graphical representation of the immune stimulatory activity of exemplary TLR3 agonists according to the invention in HEK293 cells expressing human TLR8 that were treated and analyzed according to example 2. Briefly, the HEK293 cells were treated with TLR3 agonists of the invention for 18 hr, and the levels of NF-κB subsequently produced were determined using SEAP (secreted form of human embryonic alkaline phosphatase) assay. The data demonstrate the specificity of exemplary TLR3 agonists according to the invention as such compounds did not stimulate TLR8-mediated NF-κB, which is known to be a TLR that responds to single stranded RNA molecules. More generally these data demonstrate that TLR3 agonists of the invention induce a TLR3 specific immune response.

C57BL/6 mice, 5-6 weeks old, were obtained from Taconic Farms, Germantown, N.Y. and maintained in accordance with Idera Pharmaceutical's IACUC approved animal protocols. Mice (n=2 or 3) were injected subcutaneously (s.c) with individual TLR3 agonists of the invention at 5 mg/kg, 10 mg/kg or 25 mg/kg (single dose). Naïve animals were not treated with a TLR3 agonist. Control animals were treated with 25 mg/kg poly(I:C). Serum was collected by retro-orbital bleeding 2 hr after TLR3 agonist administration and cytokine and chemokine levels were determined by ELISA or Luminex multiplex assays. The results are shown in Table 14 and FIGS. 8 and 9 and demonstrate that in vivo administration of TLR3 agonists of the invention generates unique cytokine and chemokine profiles in vivo. All reagents, including cytokine and chemokine antibodies and standards were purchased from PharMingen. (San Diego, Calif.).

TABLE 14

| Compound# | IL-12 (pg/ml) |
|---|---|
| Naive | 67.1 |
| 36 | 1142.6 |
| 37 | 5093.1 |
| 38 | 4925.0 |
| 41 | 3638.4 |
| 42 | 11902 |

Mice were dosed with 25 mg/kg of the TLR3 agonist compound. Naïve mice were treated with saline.

Example 4

In Vivo Cytokine Secretion in Mouse Model Treated with TLR3 Agonist Compounds

C57BL/6 mice, 5-6 weeks old, were obtained from Taconic Farms, Germantown, N.Y. and maintained in accordance with Idera Pharmaceutical's IACUC approved animal protocols. Mice (n=3) were injected subcutaneously (s.c) with individual TLR3 agonists of the invention at 5 mg/kg, 10 mg/kg (single dose). Naïve animals were not treated with a TLR3 agonist. Control animals were treated with 25 mg/kg poly(I:C). Serum was collected by retro-orbital bleeding 2 hr after TLR3 agonist administration and cytokine levels were determined by ELISA assay. The results are shown in Table 15 and demonstrate that in vivo administration of TLR3 agonists of the invention generates unique TLR3 stimulation, resulting in induced IL-12 concentrations in vivo. All reagents, including cytokine and chemokine antibodies and standards were purchased from PharMingen. (San Diego, Calif.).

TABLE 15

| Compound# | IL-12 (pg/ml) |
|---|---|
| Naive | 621.5 |
| 39 | 10078 |
| 40 | 32388 |
| 43 | 35655 |
| 44 | 51066 |
| 45 | 33699 |
| 46 | 24979 |
| 47 | 535.2 |
| 48 | 1311.9 |
| 49 | 181.2 |
| 50 | 41085 |
| 51 | 8470 |
| 52 | 2091 |
| 53 | 416.7 |
| 54 | 329.7 |
| 55 | 331.6 |
| 56 | 10874 |
| 57 | 2948 |
| 58 | 845.9 |
| 59 | 1704 |
| 60 | 928.8 |
| 61 | 535.2 |
| 62 | 41.1 |
| 63 | 221.1 |

Mice were dosed with 10 mg/kg of the TLR3 agonist compound. Naïve mice were treated with saline.

Example 5

In Vivo Cytokine Secretion in Mouse Model Treated with TLR3 Agonist Compounds

Figure 12:
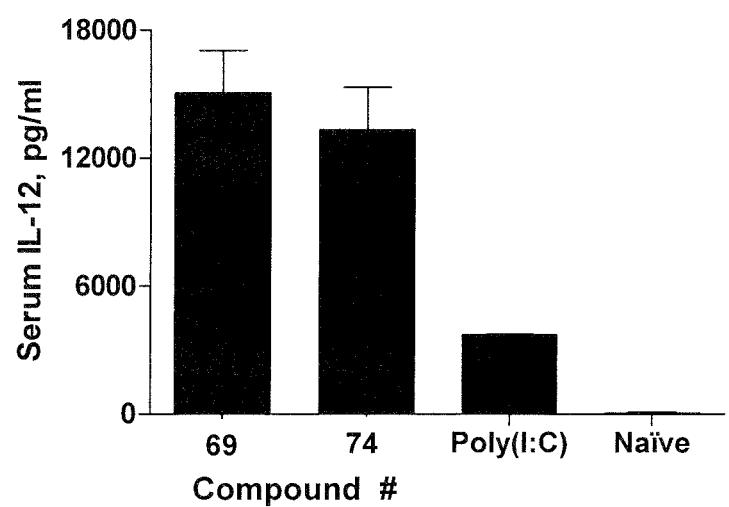
FIGS. 12 and 13 depict serum cytokine induction in C57BL/6 mice (n=2) 2 hours after they were treated and analyzed according to Example 5. Briefly, the C57BL/6 mice were injected subcutaneously with 10 mg/kg dose of TLR3 agonists, and 2 hours after administration of the agonist, serum was analyzed for immune stimulatory cytokine levels, and IL-12 levels are presented. The data demonstrate that in vivo administration of a TLR3 agonist of the invention generates a distinct TLR-mediated in vivo cytokine profile.
Figure 13:
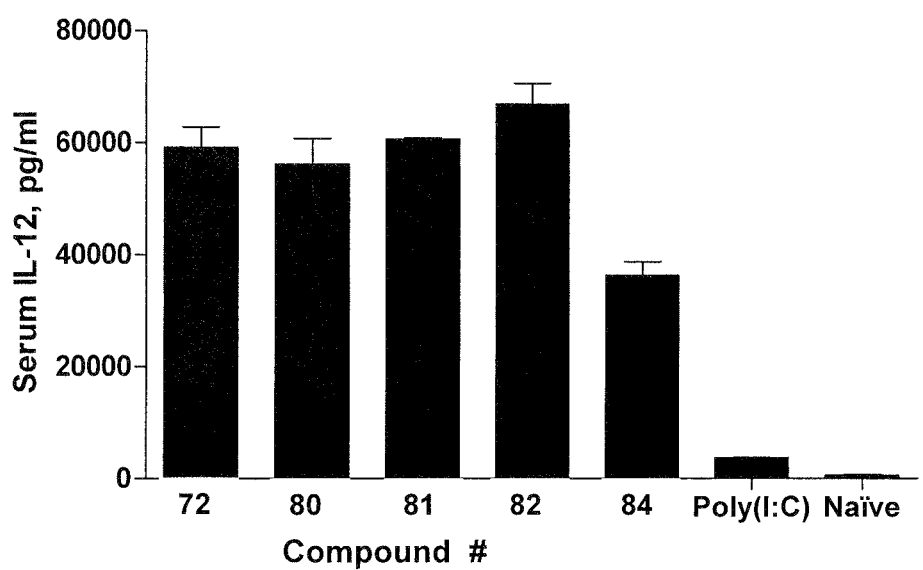

C57BL/6 mice, 5-6 weeks old, were obtained from Taconic Farms, Germantown, N.Y. and maintained in accordance with Idera Pharmaceutical's IACUC approved animal protocols. Mice (n=2) were injected subcutaneously (s.c) with individual TLR3 agonists of the invention at 10 mg/kg (single dose). Naïve animals were not treated with a TLR3 agonist. Control animals were treated with 25 mg/kg poly(I:C). Serum was collected by retro-orbital bleeding 2 hr after TLR3 agonist administration and cytokine levels were determined by ELISA assay. The results are shown in FIGS. 12 and 13 and demonstrate that in vivo administration of TLR3 agonists of the invention generates unique TLR3 stimulation, resulting in induced IL-12 concentrations in vivo. All reagents, including cytokine and chemokine antibodies and standards were purchased from PharMingen. (San Diego, Calif.).

EQUIVALENTS

Those skilled in the art will recognize, or be able to ascertain, using no more than routine experimentation, numerous equivalents to the specific substances and procedures described herein. For example, antisense oligonucleotides that overlap with the oligonucleotides may be used. Such equivalents are considered to be within the scope of this invention, and are covered by the following claims.

What is claimed is:

1. A synthetic TLR3 agonist comprising
   i) a first oligoribonucleotide having the structure: 5'-Domain A-Domain B-3'; and
   ii) a second oligoribonucleotide having the structure: 5'-Domain C-Domain D-3',
   wherein Domain A is a first complementary domain, Domain B is a polyriboinosine domain, Domain C is a second complementary domain and Domain D is a polyribocytidine domain, wherein Domain A and Domain C are complementary to each other, are from about 10 to about 20 nucleotides in length, and comprise G, C, A, T and/or U, wherein the first oligoribonucleotide and the second oligoribonucleotide bind to each other through intermolecular hydrogen bonding between (i) the complementary domains leaving a free polyriboinosine domain and a free polyribocytidine domain or (ii) between the polyriboinosine and polyribocytidine domains leaving a free first complementary domain and a free second complementary domain, and wherein additional first and/or second oligoribonucleotides can bind to the free complementary and/or polyriboinosine or polyribocytidine domains, thereby creating a chain of oligoribonucleotides.

2. A synthetic TLR3 agonist comprising
   i) a first oligoribonucleotide having the structure: 5'-Domain B-Domain A-3'; and
   ii) a second oligoribonucleotide having the structure: 5'-Domain D-Domain C-3',
   wherein Domain A is a first complementary domain, Domain B is a polyriboinosine domain, Domain C is a second complementary domain and Domain D is a polyribocytidine domain, wherein Domain A and Domain C are complementary to each other, are from about 10 to about 20 nucleotides in length, and comprise G, C, A, T and/or U, wherein the first oligoribonucleotide and the second oligoribonucleotide bind to each other through intermolecular hydrogen bonding between (i) the complementary domains leaving a free polyriboinosine domain and a free polyribocytidine domain or (ii) between the polyriboinosine and polyribocytidine domains leaving a free first complementary domain and a free second complementary domain, and wherein additional first and/or second oligoribonucleotides can bind to the free complementary and/or polyriboinosine or polyribocytidine domains, thereby creating a chain of oligoribonucleotides.

3. A composition comprising a TLR3 agonist according to claim 1 or 2 and a physiologically acceptable carrier.

4. A method for stimulating TLR3 activity comprising contacting TLR3 with a TLR3 agonist according to claim 1 or 2 or a composition according to claim 3.

5. A method for stimulating TLR3 activity in a mammal comprising administering to the mammal a TLR3 agonist according to claim 1 or 2 or a composition according to claim 3.

6. A method for stimulating TLR3-mediated immune response in a mammal comprising administering to the mammal a TLR3 agonist according to claim 1 or 2 or a composition according to claim 3.

7. A method for treating a mammal having a disease or disorder whose treatment is capable of being mediated by TLR3 comprising administering to the mammal a TLR3 agonist according to claim 1 or 2 or a composition according to claim 3.

8. A method of preventing a disease or disorder, whose prevention is capable of being mediated by TLR3, in a mammal at risk of contracting/developing such disease or disorder comprising administering to the mammal a TLR3 agonist according to claim 1 or 2 or a composition according to claim 3.

9. A vaccine comprising a composition according to claim 3, and further comprising an antigen.

10. The TLR3 agonist according to claim 1 or 2, wherein the polyriboinosine and polyribocytidine domains are from about 30 to about 40 nucleotides in length.

11. The TLR3 agonist according to claim 10, wherein the first and second complementary domains are 15 nucleotides in length and the polyriboinosine and polyribocytidine domains are 35 nucleotides in length.

12. The TLR3 agonist according to claim 1 or 2, wherein the polyriboinosine domain comprises one or more force binding sites.

13. The TLR3 agonist according to claim 1 or 2, wherein one or more hydrogen atoms in the first and/or second oligoribonucleotide are replaced by a deuterium atom through hydrogen deuterium exchange.

14. The TLR3 agonist according to claim 1 or 2 or a composition according to claim 3, further comprising one or more one or more vaccines, antigens, antibodies, cytotoxic agents, allergens, antibiotics, antisense oligonucleotides, TLR agonist, TLR antagonist, siRNA, miRNA, peptides, proteins, gene therapy vectors, DNA vaccines, adjuvants, kinase inhibitors, co-stimulatory molecules.

* * * * *